(12) United States Patent
Connor

(10) Patent No.: US 12,310,749 B2
(45) Date of Patent: May 27, 2025

(54) EYEWEAR (EYEGLASSES) WITH ELECTRODES (EEG SENSORS) FOR PREDICTION AND/OR DETECTION OF HEALTH EVENTS OR USE AS A BRAIN-TO-COMPUTER INTERFACE (BCI)

(71) Applicant: Robert A. Connor, St. Paul, MN (US)

(72) Inventor: Robert A. Connor, St. Paul, MN (US)

(73) Assignee: Medibotios MC, Ham Lake, MN (US)

( * ) Notice: Subject to any disclaimer, the term of this patent is extended or adjusted under 35 U.S.C. 154(b) by 0 days.

(21) Appl. No.: 18/411,540

(22) Filed: Jan. 12, 2024

(65) Prior Publication Data
US 2024/0148324 A1 May 9, 2024

Related U.S. Application Data

(63) Continuation-in-part of application No. 18/219,684, filed on Jul. 9, 2023, which is a continuation-in-part of application No. 17/714,988, filed on Apr. 6, 2022, now Pat. No. 11,850,052, which is a continuation-in-part of application No. 17/665,086, filed on Feb. 4, 2022, now Pat. No. 11,662,819, and a continuation-in-part of application No. 17/136,117,
(Continued)

(51) Int. Cl.
*A61B 5/00* (2006.01)
*A61B 5/291* (2021.01)
*A61B 5/296* (2021.01)

(52) U.S. Cl.
CPC ............ *A61B 5/6803* (2013.01); *A61B 5/291* (2021.01); *A61B 5/296* (2021.01); *A61B 2560/0468* (2013.01)

(58) Field of Classification Search
CPC ....... A61B 5/6803; A61B 5/291; A61B 5/296; A61B 2560/0468; A61B 5/0006; A61B 5/4094; A61B 5/7267; A61B 2562/0209; A61B 5/268; A61B 5/256; G02C 2200/26; G02C 3/003; G02C 5/14; G02C 5/143; G02C 11/10; G06F 3/016; G06F 3/015
See application file for complete search history.

(56) References Cited

U.S. PATENT DOCUMENTS 9,204,796 B2   12/2015  Tran
9,449,446 B1 *  9/2016  Mullin ................... G06F 3/012
(Continued)

OTHER PUBLICATIONS (Acar, 2019), "Wearable and Flexible Textile Electrodes for Biopotential Signal Monitoring: A Review," Electronics, 2019, 8(5), 479.
(Continued)

*Primary Examiner* — Jacqueline Cheng
*Assistant Examiner* — Tho Q Tran

(57) ABSTRACT

This invention is eyewear (e.g. eyeglasses) with electrodes (e.g. EEG sensors) which collect brain activity data (e.g. electroencephalographic data) which can be used to predict and/or detect health events (e.g. epileptic seizure, stroke, or heart attack) or function as a BCI (Brain-to-Computer Interface) for communication. There can be anterior and posterior electrodes on the eyewear temple and the temple can have an upward and/or inward curving wave or arm. A posterior electrode can have multiple electroconductive protrusions to help penetrate between strands of hair.

1 Claim, 16 Drawing Sheets

Related U.S. Application Data filed on Dec. 29, 2020, now abandoned, said application No. 17/665,086 is a continuation-in-part of application No. 17/136,117, filed on Dec. 29, 2020, now abandoned, which is a continuation-in-part of application No. 16/838,541, filed on Apr. 2, 2020, now abandoned, said application No. 18/219,684 is a continuation-in-part of application No. 16/838,541, filed on Apr. 2, 2020, now abandoned, said application No. 17/136,117 is a continuation-in-part of application No. 16/737,052, filed on Jan. 8, 2020, now Pat. No. 11,754,542, which is a continuation-in-part of application No. 16/568,580, filed on Sep. 12, 2019, now Pat. No. 11,478,158, said application No. 17/136,117 is a continuation-in-part of application No. 16/568,580, filed on Sep. 12, 2019, now Pat. No. 11,478,158, said application No. 17/665,086 is a continuation-in-part of application No. 16/554,029, filed on Aug. 28, 2019, now abandoned, said application No. 17/714,988 is a continuation-in-part of application No. 16/554,029, filed on Aug. 28, 2019, now abandoned, said application No. 16/838,541 is a continuation-in-part of application No. 16/554,029, filed on Aug. 28, 2019, now abandoned, said application No. 17/136,117 is a continuation-in-part of application No. 16/554,029, filed on Aug. 28, 2019, now abandoned, which is a continuation-in-part of application No. 16/022,987, filed on Jun. 29, 2018, now Pat. No. 11,172,859, said application No. 16/737,052 is a continuation-in-part of application No. 15/963,061, filed on Apr. 25, 2018, now Pat. No. 10,772,559, said application No. 16/568,580 is a continuation-in-part of application No. 15/963,061, filed on Apr. 25, 2018, now Pat. No. 10,772,559, which is a continuation-in-part of application No. 15/464,349, filed on Mar. 21, 2017, now Pat. No. 9,968,297, said application No. 16/838,541 is a continuation-in-part of application No. 15/236,401, filed on Aug. 13, 2016, now abandoned, said application No. 15/464,349 is a continuation-in-part of application No. 15/136,948, filed on Apr. 24, 2016, now Pat. No. 10,234,942, said application No. 16/022,987 is a continuation-in-part of application No. 15/136,948, filed on Apr. 24, 2016, now Pat. No. 10,234,942, said application No. 15/236,401 is a continuation-in-part of application No. 15/136,948, filed on Apr. 24, 2016, now Pat. No. 10,234,942, which is a continuation-in-part of application No. 14/599,522, filed on Jan. 18, 2015, now Pat. No. 9,814,426, said application No. 15/236,401 is a continuation-in-part of application No. 14/599,522, filed on Jan. 18, 2015, now Pat. No. 9,814,426, said application No. 15/464,349 is a continuation-in-part of application No. 14/562,719, filed on Dec. 7, 2014, now Pat. No. 10,130,277, said application No. 14/599,522 is a continuation-in-part of application No. 14/562,719, filed on Dec. 7, 2014, now Pat. No. 10,130,277, said application No. 15/464,349 is a continuation-in-part of application No. 14/330,649, filed on Jul. 14, 2014, now abandoned, which is a continuation-in-part of application No. 13/797,955, filed on Mar. 12, 2013, now Pat. No. 9,456,916, and a continuation-in-part of application No. 13/523,739, filed on Jun. 14, 2012, now Pat. No. 9,042,596.

(60) Provisional application No. 62/972,692, filed on Feb. 11, 2020, provisional application No. 62/851,904, filed on May 23, 2019, provisional application No. 62/796,901, filed on Jan. 25, 2019, provisional application No. 62/791,838, filed on Jan. 13, 2019, provisional application No. 62/430,667, filed on Dec. 6, 2016, provisional application No. 62/322,594, filed on Apr. 14, 2016, provisional application No. 62/303,126, filed on Mar. 3, 2016, provisional application No. 62/169,661, filed on Jun. 2, 2015, provisional application No. 62/160,172, filed on May 12, 2015, provisional application No. 62/089,696, filed on Dec. 9, 2014, provisional application No. 62/017,615, filed on Jun. 26, 2014, provisional application No. 61/939,244, filed on Feb. 12, 2014, provisional application No. 61/932,517, filed on Jan. 28, 2014, provisional application No. 61/729,494, filed on Nov. 23, 2012.

(56) References Cited

U.S. PATENT DOCUMENTS

| | | |
|---|---|---|
| 10,512,770 B2 | 12/2019 | Wingeier et al. |
| 10,564,717 B1 | 2/2020 | Shahmohammadi et al. |
| 10,656,710 B1 | 5/2020 | Shahmohammadi et al. |
| 10,809,796 B2 | 10/2020 | Armstrong-Muntner et al. |
| 10,962,789 B1 | 3/2021 | Lewis |
| 11,209,654 B1 | 12/2021 | Lewis |
| 11,850,055 B2 | 12/2023 | Hiratsuka |
| 2006/0252978 A1 | 11/2006 | Vesely et al. |
| 2006/0252979 A1 | 11/2006 | Vesely et al. |
| 2007/0019279 A1 | 1/2007 | Goodall et al. |
| 2007/0106172 A1 | 5/2007 | Abreu |
| 2009/0259137 A1* | 10/2009 | Delic .................. A61B 5/6843 600/545 |
| 2011/0298706 A1 | 12/2011 | Mann |
| 2012/0029336 A1* | 2/2012 | Terada ................ A61B 5/6843 600/383 |
| 2013/0274583 A1 | 10/2013 | Heck |
| 2014/0023999 A1 | 1/2014 | Greder |
| 2014/0081117 A1* | 3/2014 | Kato ..................... A61B 3/113 600/383 |
| 2014/0347265 A1 | 11/2014 | Aimone et al. |
| 2015/0379896 A1 | 12/2015 | Yang |
| 2016/0070122 A1 | 3/2016 | Sales |
| 2016/0143554 A1 | 5/2016 | Lim et al. |
| 2016/0256086 A1 | 9/2016 | Byrd et al. |
| 2016/0287173 A1 | 10/2016 | Abreu |
| 2017/0071495 A1* | 3/2017 | Denison ................ A61B 5/291 |
| 2017/0258410 A1 | 9/2017 | Gras |
| 2018/0103894 A1 | 4/2018 | Tzvieli |
| 2018/0221620 A1 | 8/2018 | Metzger |
| 2019/0101977 A1 | 4/2019 | Armstrong-Muntner |
| 2019/0200925 A1 | 7/2019 | Aimone et al. |
| 2019/0239807 A1 | 8/2019 | Watson et al. |
| 2019/0336765 A1 | 11/2019 | Charlesworth et al. |
| 2020/0019243 A1 | 1/2020 | Aimone et al. |
| 2020/0081247 A1 | 3/2020 | Khaderi et al. |
| 2020/0133393 A1 | 4/2020 | Forsland et al. |
| 2020/0237249 A1 | 7/2020 | Gunasekar et al. |
| 2020/0264454 A1 | 8/2020 | Mackenzie et al. |
| 2020/0268296 A1 | 8/2020 | Alcaide et al. |
| 2020/0337653 A1 | 10/2020 | Alcaide et al. |
| 2020/0375524 A1 | 12/2020 | Aminifar et al. |
| 2021/0121115 A1 | 4/2021 | Chiang |
| 2021/0200313 A1 | 7/2021 | Aimone et al. |
| 2021/0223864 A1 | 7/2021 | Forsland et al. |
| 2023/0018247 A1 | 1/2023 | Elias |
| 2023/0172468 A1 | 6/2023 | Kaplan et al. |
| 2023/0320669 A1 | 10/2023 | Desai et al. |

OTHER PUBLICATIONS (Casson, 2019), "Wearable EEG and Beyond," Biomedical Engineering Letters, Jan., 2019, 9(1), 53-71.

(56) References Cited

OTHER PUBLICATIONS (Chen, 2014), "Soft, Comfortable Polymer Dry Electrodes for High Quality ECG and EEG Recording," Sensors, Dec. 10, 2014, 14(12), 23758-80.
(Chen, 2016), "Polymer-Based Dry Electrodes for Biopotential Measurements," Thesis, Arenberg Doctoral School, 2016.
(Chi, 2010), "Dry-Contact and Noncontact Biopotential Electrodes: Methodological Review," IEEE Reviews in Biomedical Engineering, 2010, 3, 106-119.
(Chlaihawi, 2018), "Development of Printed and Flexible Dry ECG Electrodes," Sensing and Bio-Sensing Research, 2018, 20, 9-15.
(Flumeri, 2019), "The Dry Revolution: Evaluation of Three Different EEG Dry Electrode Types in Terms of Signal Spectral Features, Mental States Classification and Usability," Sensors, Mar. 19, 2019, 19(6), 1365.
(Fu, 2020), "Dry Electrodes for Human Bioelectrical Signal Monitoring," Sensors, Jun. 29, 2020, 20(13), 3651.
(Gao, 2018), "Soft Pin-Shaped Dry Electrode with Bristles for EEG Signal Measurements," Sensors and Actuators, 2018, vol. 283, 348-361.
(Hsu, 2014), "Developing Barbed Microtip-Based Electrode Arrays for Biopotential Measurement," Sensors, 2014, 14(7), 12370-12386.
(Kocturova, 2019), "Comparison of Dry Electrodes for Mobile EEG System," 2019.
(Krachunov, 2016), "3D Printed Dry EEG Electrodes," Sensors, 2016, 16(10), 1635.
(Lau-Zhu, 2019), "Mobile EEG in Research on Neurodevelopmental Disorders: Opportunities and Challenges," Developmental Cognitive Neuroscience, 2019, vol. 36.
(Lee, 2015), "Reverse-Curve-Arch-Shaped Dry EEG Electrode for Increased Skin-Electrode Contact Area on Hairy Scalps," Electronics Letters, Oct. 1, 2015.
(Lopez-Gordo, 2014), "Dry EEG Electrodes," Sensors, Jul. 18, 2014, 14(7), 12847-70.
(Mota, 2013), "Development of a Quasi-Dry Electrode for EEG Recording," Sensors and Actuators, 2013, vol. 199, 310-317.
(Olesen, 2020), "Development and Assessment of Electrodes and Instrumentation for Plantar Skin Impedance Measurements," Thesis, Master in Electronics, Informatics and Technology, University of Oslo, Autumn, 2020.
(Ouyang, 2021), "Application of Intrinsically Conducting Polymers in Flexible Electronics," SmartMat, Aug. 18, 2021, 2.
(Ruffini, 2008), "First Human Trials of a Dry Electrophysiology Sensor Using a Carbon Nanotube Array Interface," Sensors and Actuators, Jun. 15, 2008, 144.
(Shad, 2020), "Impedance and Noise of Passive and Active Dry EEG Electrodes: A Review," IEEE Sensors Journal, Jul. 27, 2020.
(Sunwoo, 2020), "Advances in Soft Bioelectronics for Brain Research and Clinical Neuroengineering," Matter, 2020, 3(6) 1923-1947.
(Zhang, 2020), "Fully Organic Compliant Dry Electrodes Self-Adhesive to Skin for Long-Term Motion-Robust Epidermal Biopotential Monitoring," Nature Communications, 2020, 11, 4683.

\* cited by examiner

EYEWEAR (EYEGLASSES) WITH ELECTRODES (EEG SENSORS) FOR PREDICTION AND/OR DETECTION OF HEALTH EVENTS OR USE AS A BRAIN-TO-COMPUTER INTERFACE (BCI)

CROSS-REFERENCE TO RELATED APPLICATIONS

This patent application is a continuation-in-part of U.S. patent application Ser. No. 18/219,684 filed on 2023 Jul. 9. U.S. patent application Ser. No. 18/219,684 was a continuation-in-part of U.S. patent application Ser. No. 17/714,988 filed on 2022 Apr. 6. U.S. patent application Ser. No. 18/219,684 was a continuation-in-part of U.S. patent application Ser. No. 16/838,541 filed on 2020 Apr. 2.

U.S. patent application Ser. No. 17/714,988 was a continuation-in-part of U.S. patent application Ser. No. 17/665,086 filed on 2022 Feb. 4. U.S. patent application Ser. No. 17/714,988 was a continuation-in-part of U.S. patent application Ser. No. 17/136,117 filed on 2020 Dec. 29. U.S. patent application Ser. No. 17/714,988 was a continuation-in-part of U.S. patent application Ser. No. 16/554,029 filed on 2019 Aug. 28. U.S. patent application Ser. No. 17/665,086 was a continuation-in-part of U.S. patent application Ser. No. 17/136,117 filed on 2020 Dec. 29. U.S. patent application Ser. No. 17/665,086 was a continuation-in-part of U.S. patent application Ser. No. 16/554,029 filed on 2019 Aug. 28.

U.S. patent application Ser. No. 17/136,117 was a continuation-in-part of U.S. patent application Ser. No. 16/838,541 filed on 2020 Apr. 2. U.S. patent application Ser. No. 17/136,117 claimed the priority benefit of U.S. provisional patent application 62/972,692 filed on 2020 Feb. 11. U.S. patent application Ser. No. 17/136,117 was a continuation-in-part of U.S. patent application Ser. No. 16/737,052 filed on 2020 Jan. 8. U.S. patent application Ser. No. 17/136,117 was a continuation-in-part of U.S. patent application Ser. No. 16/568,580 filed on 2019 Sep. 12. U.S. patent application Ser. No. 17/136,117 was a continuation-in-part of U.S. patent application Ser. No. 16/554,029 filed on 2019 Aug. 28.

U.S. patent application Ser. No. 16/838,541 claimed the priority benefit of U.S. provisional patent application 62/972,692 filed on 2020 Feb. 11. U.S. patent application Ser. No. 16/838,541 was a continuation-in-part of U.S. patent application Ser. No. 16/554,029 filed on 2019 Aug. 28. U.S. patent application Ser. No. 16/838,541 claimed the priority benefit of U.S. provisional patent application 62/851,917 filed on 2019 May 23. U.S. patent application Ser. No. 16/838,541 claimed the priority benefit of U.S. provisional patent application 62/837,712 filed on 2019 Apr. 23. U.S. patent application Ser. No. 16/838,541 was a continuation-in-part of U.S. patent application Ser. No. 15/236,401 filed on 2016 Aug. 13. U.S. patent application Ser. No. 16/737,052 was a continuation-in-part of U.S. patent application Ser. No. 16/568,580 filed on 2019 Sep. 12. U.S. patent application Ser. No. 16/737,052 was a continuation-in-part of U.S. patent application Ser. No. 15/963,061 filed on 2018 Apr. 25. U.S. patent application Ser. No. 16/568,580 was a continuation-in-part of U.S. patent application Ser. No. 15/963,061 filed on 2018 Apr. 25.

U.S. patent application Ser. No. 16/554,029 claimed the priority benefit of U.S. provisional patent application 62/851,904 filed on 2019 May 23. U.S. patent application Ser. No. 16/554,029 claimed the priority benefit of U.S. provisional patent application 62/796,901 filed on 2019 Jan. 25. U.S. patent application Ser. No. 16/554,029 claimed the priority benefit of U.S. provisional patent application 62/791,838 filed on 2019 Jan. 13. U.S. patent application Ser. No. 16/554,029 was a continuation-in-part of U.S. patent application Ser. No. 16/022,987 filed on 2018 Jun. 29. U.S. patent application Ser. No. 16/022,987 was a continuation-in-part of U.S. patent application Ser. No. 15/136,948 filed on 2016 Apr. 24. U.S. patent application Ser. No. 15/963,061 was a continuation-in-part of U.S. patent application Ser. No. 15/464,349 filed on 2017 Mar. 21.

U.S. patent application Ser. No. 15/464,349 claimed the priority benefit of U.S. provisional patent application 62/430,667 filed on 2016 Dec. 6. U.S. patent application Ser. No. 15/464,349 was a continuation-in-part of U.S. patent application Ser. No. 15/136,948 filed on 2016 Apr. 24. U.S. patent application Ser. No. 15/464,349 was a continuation-in-part of U.S. patent application Ser. No. 14/562,719 filed on 2014 Dec. 7. U.S. patent application Ser. No. 15/464,349 was a continuation-in-part of U.S. patent application Ser. No. 14/330,649 filed on 2014 Jul. 14. U.S. patent application Ser. No. 15/236,401 was a continuation-in-part of U.S. patent application Ser. No. 15/136,948 filed on 2016 Apr. 24. U.S. patent application Ser. No. 15/236,401 was a continuation-in-part of U.S. patent application Ser. No. 14/599,522 filed on 2015 Jan. 18.

U.S. patent application Ser. No. 15/136,948 claimed the priority benefit of U.S. provisional patent application 62/322,594 filed on 2016 Apr. 14. U.S. patent application Ser. No. 15/136,948 claimed the priority benefit of U.S. provisional patent application 62/303,126 filed on 2016 Mar. 3. U.S. patent application Ser. No. 15/136,948 claimed the priority benefit of U.S. provisional patent application 62/169,661 filed on 2015 Jun. 2. U.S. patent application Ser. No. 15/136,948 claimed the priority benefit of U.S. provisional patent application 62/160,172 filed on 2015 May 12. U.S. patent application Ser. No. 15/136,948 was a continuation-in-part of U.S. patent application Ser. No. 14/599,522 filed on 2015 Jan. 18.

U.S. patent application Ser. No. 14/599,522 claimed the priority benefit of U.S. provisional patent application 62/089,696 filed on 2014 Dec. 9. U.S. patent application Ser. No. 14/599,522 was a continuation-in-part of U.S. patent application Ser. No. 14/562,719 filed on 2014 Dec. 7. U.S. patent application Ser. No. 14/599,522 claimed the priority benefit of U.S. provisional patent application 62/017,615 filed on 2014 Jun. 26. U.S. patent application Ser. No. 14/599,522 claimed the priority benefit of U.S. provisional patent application 61/939,244 filed on 2014 Feb. 12. U.S. patent application Ser. No. 14/599,522 claimed the priority benefit of U.S. provisional patent application 61/932,517 filed on 2014 Jan. 28.

U.S. patent application Ser. No. 14/562,719 claimed the priority benefit of U.S. provisional patent application 61/932,517 filed on 2014 Jan. 28. U.S. patent application Ser. No. 14/330,649 was a continuation-in-part of U.S. patent application Ser. No. 13/797,955 filed on 2013 Mar. 12. U.S. patent application Ser. No. 14/330,649 was a continuation-in-part of U.S. patent application Ser. No. 13/523,739 filed on 2012 Jun. 14. U.S. patent application Ser. No. 13/797,955 claimed the priority benefit of U.S. provisional patent application 61/729,494 filed on 2012 Nov. 23.

The entire contents of these applications are incorporated herein by reference.

FEDERALLY SPONSORED RESEARCH

Not Applicable

SEQUENCE LISTING OR PROGRAM

Not Applicable

BACKGROUND

Field of Invention

This invention relates to eyewear with electrodes.

Introduction

Eyewear (e.g. eyeglasses) with electrodes (e.g. EEG sensors) which collect brain activity data (e.g. electroencephalographic data) can be used to predict and/or detect health events (e.g. seizure, stroke, or heart attack) or function as a BCI (Brain-to-Computer Interface) for communication.

Review of the Relevant Art

In the patent literature, U.S. patent applications 20060252978 (Vesely et al., Nov. 9, 2006, "Biofeedback Eyewear System") and 20060252979 (Vesely et al., Nov. 9, 2006, "Biofeedback Eyewear System") disclose a biofeedback eyewear system with stereo lenses, binaural audio, and electrodes. U.S. patent application 20070019279 (Goodall et al., Jan. 25, 2007, "Adjustable Lens System with Neural-Based Control") discloses using neural or neuromuscular activity to control an adjustable lens. U.S. patent application 20070106172 (Abreu, May 10, 2007, "Apparatus and Method for Measuring Biologic Parameters") discloses putting sensors on a physiologic tunnel in order to measure physical, chemical and biological parameters.

U.S. patent application 20110298706 (Mann, Dec. 8, 2011, "Brainwave Actuated Apparatus") discloses a brainwave-actuated apparatus with a brainwave sensor for outputting a brainwave signal, an effector responsive to an input signal, a controller, and a control input to said effector. With respect to wearable technology pioneers, he's the man! U.S. patent application 20130274583 (Heck, Oct. 17, 2013, "Electrodes Adapted for Transmitting or Measuring Voltages Through Hair") discloses an electrode to measure and/or deliver voltages through skin covered with hair. U.S. patent application 20140023999 (Greder, Jan. 23, 2014, "Detection and Feedback of Information Associated with Executive Function") discloses a neurosensing and feedback device which detects mental states.

U.S. patent application 20140347265 (Aimone et al., Nov. 27, 2014, "Wearable Computing Apparatus and Method") discloses a method of using a wearable computing device with bio-signal sensors. U.S. Pat. No. 9,204,796 (Tran, Dec. 8, 2015, "Personal Emergency Response (PER) System") discloses a system with sensors which detects activities of a mobile object. U.S. patent application 20150379896 (Yang, Dec. 31, 2015, "Intelligent Eyewear and Control Method Thereof") discloses intelligent eyewear including an eyeglass, an eyeglass frame, and a leg with a brainwave recognizer. U.S. patent application 20160070122 (Sales, Mar. 10, 2016, "Computerized Replacement Temple for Standard Eyewear") discloses a computerized eyewear retrofit kit comprising a replacement temple.

U.S. patent application 20160143554 (Lim et al., May 26, 2016, "Apparatus for Measuring Bioelectrical Signals") discloses using tapered electrodes to measure bioelectrical signals. U.S. patent application 20160256086 (Byrd et al., Sep. 8, 2016, "Non-Invasive, Bioelectric Lifestyle Management Device") discloses identification of biological conditions via bioelectric signals. U.S. patent application 20160287173 (Abreu, Oct. 6, 2016, "Apparatus Configured to Support a Device on a Head") discloses adjustments to improve the fit of a head-positioned apparatus.

U.S. patent application 20170258410 (Gras, Sep. 14, 2017, "Method and Apparatus for Prediction of Epileptic Seizures") discloses a system for predicting epileptic seizures via sensors which record brain activity. U.S. patent application 20180103894 (Tzvieli, Apr. 19, 2018, "Neurofeedback Eyeglasses") discloses using forehead thermal measurements in brain-related treatments such as neurofeedback. U.S. patent application 20180221620 (Metzger, Aug. 9, 2018, "Modulation of Brainwave Activity Using Non-Invasive Stimulation of Sensory Pathways") discloses modulation of the central nervous system (e.g. brain oscillatory activity) via non-invasive stimuli.

U.S. patent application 20200081247 (Khaderi et al., Mar. 15, 2019, "Modular Display and Sensor System for Attaching to Eyeglass Frames and Capturing Physiological Data") discloses a modular device with EOG sensors that is integrated with eyeglasses. U.S. patent application 20190101977 (Armstrong-Muntner et al., Apr. 4, 2019, "Monitoring a User of a Head-Wearable Electronic Device") and U.S. patent Ser. No. 10/809,796 (Armstrong-Muntner et al., Oct. 20, 2020, "Monitoring a User of a Head-Wearable Electronic Device") disclose systems, methods, and computer-readable media for monitoring a person via a light-sensing head-wearable electronic device. U.S. patent application 20190200925 (Aimone et al., Jul. 4, 2019, "Wearable Computing Device") discloses a wearable device with a flexible band on a portion of a person's head.

U.S. patent application 20190239807 (Watson et al., Aug. 8, 2019, "Hair Ratcheting Electroencephalogram Sensors") discloses a locking mechanism in an EEG sensor which permits one-way axial motion of a thread. U.S. patent application 20190336765 (Charlesworth et al., Nov. 7, 2019, "Apparatuses and Methods for Transdermal Electrical Stimulation of Nerves to Modify or Induce a Cognitive State") discloses Transdermal Electrical Stimulation (TES) applicators for modifying a subject's cognitive state by applying stimulation. U.S. patent Ser. No. 10/512,770 (Wingeier et al., Dec. 24, 2019, "System for Electrical Stimulation") discloses electrodes with hydrophilic and conductive layers.

U.S. patent applications 20200019243 (Aimone et al., Jan. 16, 2020, "Wearable Computing Device with Electrophysiological Sensors") and 20210200313 (Aimone et al., Jul. 1, 2021, "Wearable Computing Device with Electrophysiological Sensors") disclose a wearable computing device with bio-signal sensors and feedback providing an interactive mediated reality ("VR") environment. U.S. Pat. No. 10,564,717 (Shahmohammadi et al., Feb. 18, 2020, "Apparatus, Systems, and Methods for Sensing Biopotential Signals") and U.S. Pat. No. 10,656,710 (Shahmohammadi et al., May 19, 2020, "Apparatus, Systems, and Methods for Sensing Biopotential Signals Via Compliant Electrodes") disclose a head-mounted-display device with electrodes which measures an EOG or EMG signal.

U.S. patent applications 20200133393 (Forsland et al., Apr. 30, 2020, "Brain Computer Interface for Augmented Reality") and 20210223864 (Forsland et al., Jul. 22, 2021, "Brain Computer Interface for Augmented Reality") disclose a brain computer interface in a headset with an augmented reality display, one or more sensors, a processing module, at least one biofeedback device, and a battery. U.S. patent application 20200237249 (Gunasekar et al., Jul. 30, 2020, "Headset and Electrodes for Sensing Bioelectrical Potential and Methods of Operation Thereof") discloses medical devices for sensing bioelectrical potential including an electroencephalography (EEG) headset with electrodes.

U.S. patent application 20200264454 (Mackenzie et al., Aug. 20, 2020, "Eyeglasses with Bio-Signal Sensors") discloses eyeglasses with a front portion for holding two lenses, an assembly for attaching to a signal pod, side arms connected to the front portion, a nose assembly connected to the front portion, and nose contacts for supporting the front portion. U.S. patent applications 20200268296 (Alcaide et al., Aug. 27, 2020, "Brain-Computer Interface with Adaptations for High-Speed, Accurate, and Intuitive User Interactions") and 20200337653 (Alcaide et al., Oct. 29, 2020, "Brain-Computer Interface with Adaptations for High-Speed, Accurate, and Intuitive User Interactions") disclose a Brain-to-Computer Interface (BCI) that combines real-time eye-movement tracking and brain activity tracking.

U.S. patent application 20200375524 (Aminifar et al, Dec. 3, 2020, "A Wearable System for Real-Time Detection of Epileptic Seizures") discloses a wearable system for epileptic seizure detection comprising eyeglasses with electrodes in the left and right arms. U.S. Pat. No. 10,962,789 (Lewis, Mar. 30, 2021, "Digital Eyewear System and Method for the Treatment and Prevention of Migraines and Photophobia") and U.S. Pat. No. 11,209,654 (Lewis, Dec. 28, 2021, "Digital Eyewear System and Method for the Treatment and Prevention of Migraines and Photophobia") disclose digital eyewear for monitoring, detecting, and predicting, preventing, treating, and training patients for self-care of migraines and/or photophobia.

U.S. patent application 20210121115 (Chiang, Apr. 29, 2021, "EEG Signal Monitoring Adapter Device Configurable on Eyewear") discloses an EEG adapter device for eyewear which can be worn invisibly and continuously. U.S. patent application 20230018247 (Elias, Jan. 19, 2023, "Brain-Activity Actuated Extended-Reality Device") discloses the use of quantum sensors in an extended reality device. U.S. patent application 20230172468 (Kaplan et al., Jun. 8, 2023, "PPG and ECG Sensors for Smart Glasses") discloses smart glasses with photoplethysmography and electrocardiogram sensors.

U.S. patent application 20230320669 (Desai et al., Oct. 12, 2023, "Real-Time In-Ear Electroencephalography Signal Verification") discloses a real-time in-ear EEG signal verification system. U.S. Pat. No. 11,850,055 (Hiratsuka, Dec. 26, 2023, "Electroencephalographic Data Analysis System, Information Processing Terminal, Electronic Device, and Method of Presenting Information for Dementia Examination") discloses an electronic device to acquire and analyze electroencephalogram data for examination of cognitive function.

There is also relevant art in the non-patent literature. (Acar, 2019), "Wearable and Flexible Textile Electrodes for Biopotential Signal Monitoring: A Review," Electronics, 2019, 8(5), 479, presents a systematic review of wearable textile electrodes for physiological signal monitoring. (Casson, 2019), "Wearable EEG and Beyond," Biomedical Engineering Letters, January, 2019, 9(1), 53-71, reviews recent progress on electrodes used to make connections to the head and the physical EEG hardware. (Chen, 2014), "Soft, Comfortable Polymer Dry Electrodes for High Quality ECG and EEG Recording," Sensors, Dec. 10, 2014, 14(12), 23758-80, discloses dry electrodes fabricated from EPDM rubber containing various additives for optimum conductivity, flexibility and ease of fabrication.

(Chen, 2016), "Polymer-Based Dry Electrodes for Biopotential Measurements," Thesis, Arenberg Doctoral School, 2016, investigates the mechanical properties of the polymer dry electrodes with compression tests for elastic modulus and compliance characterization. (Chi, 2010), "Dry-Contact and Noncontact Biopotential Electrodes: Methodological Review," IEEE Reviews in Biomedical Engineering, 2010, 3, 106-119, explores the use of dry/noncontact electrodes for clinical use by explaining the electrical models for dry, insulated and noncontact electrodes and showing performance limits, along with measured data. (Chlaihawi, 2018), "Development of Printed and Flexible Dry ECG Electrodes," Sensing and Bio-Sensing Research, 2018, 20, 9-15, discloses printed, flexible and wearable dry electrodes for monitoring electrocardiogram (ECG) signals without any skin preparation or wet gel.

(Flumeri, 2019), "The Dry Revolution: Evaluation of Three Different EEG Dry Electrode Types in Terms of Signal Spectral Features, Mental States Classification and Usability," Sensors, Mar. 19, 2019, 19(6), 1365, compares three different dry electrode types: gold-coated single pin, multiple pins and solid-gel. (Fu, 2020), "Dry Electrodes for Human Bioelectrical Signal Monitoring," Sensors, Jun. 29, 2020, 20(13), 3651, gives a retrospective overview of the development of dry electrodes used for monitoring bioelectrical signals, including sensing principles, material selection, device preparation, and measurement performance. (Gao, 2018), "Soft Pin-Shaped Dry Electrode with Bristles for EEG Signal Measurements," Sensors and Actuators, 2018, Vol. 283, 348-361, presents a novel soft pin-shaped dry electrode for electroencephalography recording.

(Hsu, 2014), "Developing Barbed Microtip-Based Electrode Arrays for Biopotential Measurement," Sensors, 2014, 14(7), 12370-12386, discloses the fabrication of barbed microtip-based electrode arrays via silicon wet etching. (Kocturova, 2019), "Comparison of Dry Electrodes for Mobile EEG System," 2019, evaluates two types of comb electrodes: one based on a Ag—AgCl alloy and one based on a flexible conductive polymer. (Krachunov, 2016), "3D Printed Dry EEG Electrodes," Sensors, 2016, 16(10), 1635, presents a novel methodology for the design and manufacture of dry electrodes using low cost desktop 3D printers.

(Lau-Zhu, 2019), "Mobile EEG in Research on Neurodevelopmental Disorders: Opportunities and Challenges," Developmental Cognitive Neuroscience, 2019, Vol. 36, presents a brief overview of recent developments in mobile EEG technologies. (Lee, 2015), "Reverse-Curve-Arch-Shaped Dry EEG Electrode for Increased Skin-Electrode Contact Area on Hairy Scalps," Electronics Letters, Oct. 1, 2015, discloses reverse-curve-arch-shaped dry EEG electrodes for use in increasing the skin-electrode contact area on hairy scalps. (Lopez-Gordo, 2014), "Dry EEG Electrodes," Sensors, Jul. 18, 2014, 14(7), 12847-70, reviews current approaches to developing dry EEG electrodes for clinical and other applications.

(Mota, 2013), "Development of a Quasi-Dry Electrode for EEG Recording," Sensors and Actuators, 2013, Vol. 199, 310-317, reports on the development of a novel polymer-based electrode prototype for electroencephalography (EEG) between classic "wet" and "dry" electrodes. (Olesen, 2020), "Development and Assessment of Electrodes and Instrumentation for Plantar Skin Impedance Measurements," Thesis, Master in Electronics, Informatics and Technology, University of Oslo, Autumn, 2020, describes the development and testing of electrodes for plantar bioimpedance measurements. (Ouyang, 2021), "Application of Intrinsically Conducting Polymers in Flexible Electronics," SmartMat, Aug. 18, 2021, 2, discusses the use of intrinsically conducting polymers (ICPs), such as polyacetylene, polyaniline, polypyrrole, polythiophene, and poly(3,4-ethylenedioxythiophene) (PEDOT) for dry electrodes.

(Ruffini, 2008), "First Human Trials of a Dry Electrophysiology Sensor Using a Carbon Nanotube Array Interface," Sensors and Actuators, Jun. 15, 2008, 144, reports the results from the first human trials of a new dry electrode sensor for surface biopotential applications, wherein the contact surface of the electrode is covered with carbon nanotubes. (Shad, 2020), "Impedance and Noise of Passive and Active Dry EEG Electrodes: A Review," IEEE Sensors Journal, Jul. 27, 2020, reviews the impedance and noise of passive and active dry EEG electrodes. (Sunwoo, 2020), "Advances in Soft Bioelectronics for Brain Research and Clinical Neuroengineering," Matter, 2020, 3(6) 1923-1947, reviews recent technological advances using unconventional soft materials, such as silicon/metal nanowires, functionalized hydrogels, and stretchable conductive nanocomposites. (Zhang, 2020), "Fully Organic Compliant Dry Electrodes Self-Adhesive to Skin for Long-Term Motion-Robust Epidermal Biopotential Monitoring," Nature Communications, 2020, 11, 4683, reports an intrinsically conductive polymer dry electrode with excellent self-adhesiveness, stretchability, and conductivity.

SUMMARY OF THE INVENTION

This invention is eyewear (e.g. eyeglasses) with electrodes (e.g. EEG sensors) which collect brain activity data (e.g. electroencephalographic data). There can be an electrode on the anterior portion of an eyewear temple (e.g. sidepiece) and an electrode on the posterior portion of the temple. The posterior electrode can have multiple electroconductive protrusions to help penetrate between strands of hair. The temple can have an upward and/or inward curving wave or arm. This eyewear can be used to predict and/or detect health events (e.g. epileptic seizure, stroke, or heart attack) or function as a BCI (Brain-to-Computer Interface) for communication.

INTRODUCTION TO THE FIGURES

DETAILED DESCRIPTION OF THE FIGURES

Figure 1:
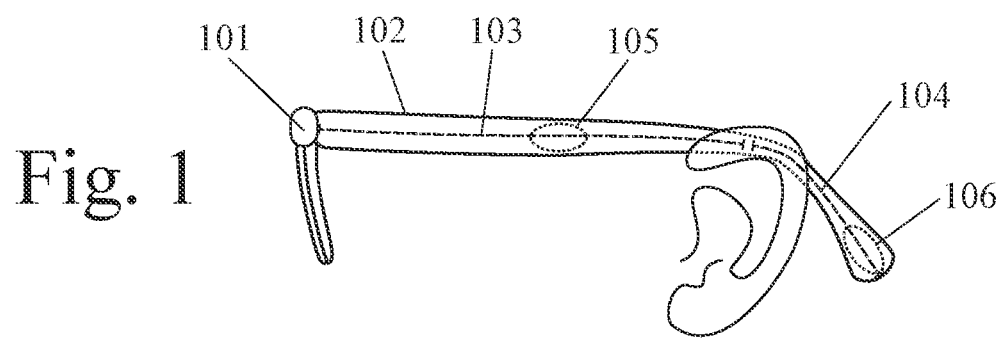
FIGS. 1-3 show three views of eyewear with anterior and posterior electrodes on a conventional temple.

Before discussing example embodiments in specific figures, it is useful to provide an introductory section. This introductory section discloses several useful design concepts and example variations which can then be applied to the figures which follow. To start this section, it is important to note that eyewear (e.g. eyeglasses) can comprise: a front piece (further comprising lenses, rims around the lenses, a nose bridge, and nose pads); a right-side temple (also called a sidepiece, bow, arm, or leg) which spans between the front piece and a person's right outer ear (e.g. auricle); and a left-side temple which spans between the front piece the person's left outer ear.

The eyewear temple (also called a sidepiece, bow, arm, or leg) can be conceptually divided into an anterior portion and a posterior portion, wherein the dividing point between the anterior portion and the posterior portion is where the temple rests on top of a person's outer ear (auricle). The anterior longitudinal axis of the temple is the central longitudinal axis through the anterior portion of the temple. The posterior longitudinal axis of the temple is the central longitudinal axis through the posterior portion of the temple.

Electrodes which are incorporated into eyewear (e.g. eyeglasses) can comprise EEG sensors. An EEG sensor is a sensor which monitors and/or records electrical and/or electromagnetic energy from a person's brain (e.g. brainwaves). An EEG sensor can also be described as an electrical and/or electromagnetic energy sensor which monitors and/or records electrical signals from a person's brain.

In an example, eyewear (e.g. eyeglasses) with electrodes (EEG sensors and/or electromagnetic energy sensors) can comprise: an eyewear front piece; two eyewear temples, wherein a temple is conceptually divided into an anterior portion which is anterior to where the temple rests on a person's auricle and a posterior portion which is posterior to where the temple rests on the person's auricle; at least one an anterior electrode, wherein the anterior electrode is on the anterior portion of a temple; and at least one a posterior electrode, wherein the posterior electrode is on the posterior portion of the temple. In an example, the side of the anterior electrode which faces toward a person's head can be substantially flat and the side of the posterior electrode which faces toward the person's head can have a plurality of electroconductive protrusions which contact the surface of the person's head.

In an example, electroencephalographic eyewear can comprise: a front section of an eyewear frame which is configured to span the front of a person's face; a side section of the eyewear frame which is configured to: span forward from one of the person's ears; then span upward, forward, and inward toward the center of the person's forehead to a location over the person's forehead above one of the person's eyes; then span downward, backward, and outward away from the center of the person's forehead; and then span forward to connect to the front section; and at least one electromagnetic energy sensor which is attached to the side section which collects data concerning electromagnetic brain activity.

In an example, eyewear (e.g. eyeglasses) with electrodes (EEG sensors and/or electromagnetic energy sensors) can comprise: a front piece which is configured to span the front of a person's head; a temple which is configured to span from an auricle to the front piece; a flexible protrusion which is part of, or attached to, the temple; and an electrode which collects data concerning brain activity, wherein the protrusion is configured to hold the electrode on the person's head. In an example, the flexible protrusion can have a first configuration in which it extends a first distance from the temple toward the person's head and a second configuration in which it extends a second distance from the temple toward the person's head, wherein the second distance is greater than the first distance. In an example, the flexible protrusion can be moved from the first configuration to the second configuration by moving a knob, button, pin, or clip. In an example, the flexible protrusion can be moved from the first configuration to the second configuration by moving sliding the knob, button, pin, or clip, thereby moving one end of the flexible protrusion closer to the other end of the flexible protrusion and causing a middle portion of the flexible protrusion to bulge out towards toward the person's head. In an example, one end of the flexible protrusion can be slid closer to the other end along a track or channel, thereby causing the middle portion of the flexible protrusion to bulge out toward the person's head.

In an example, an electrode (e.g. EEG sensor) on eyewear (e.g. eyeglasses) worn by a person can part be of a system to predict and/or detect a health event (e.g. seizure, stroke, or heart attack) by monitoring and/or recording electromagnetic signals from the person's brain (e.g. brainwaves). In an example, data from electrodes on eyewear worn by a person can be analyzed by artificial intelligence and/or machine learning to identify (e.g. interpret) messages (e.g. words) from the person's (electrical and/or electromagnetic) brain activity, wherein these messages are then communicated to one or more other people. In an example, data from electrodes on eyewear worn by a person can be analyzed by artificial intelligence and/or machine learning to predict and/or detect a cardiovascular or neurological event (e.g. heart attack or stroke).

In an example, eyewear (e.g. eyeglasses) with a plurality of electrodes (e.g. EEG sensors) can comprise a BCI (Brain-to-Computer Interface) which enables a person wearing the eyewear to issue commands and/or send communication to a computer via thought alone. In an example, eyewear with one or more electrodes can detect electrical activity in a person's brain. In an example, eyewear with one or more electrodes (e.g. EEG sensors) worn by a person can collect data concerning brain wave activity which is used to predict and/or detect an acute health event (e.g. seizure, stroke, or heart attack). In an example, a wearable device or system for predicting and/or detecting health events (e.g. a seizure, stroke, or heart attack) can comprise a module with at least one electrode (e.g. EEG sensor) which is removably-attached to eyewear (e.g. eyeglasses).

In an example, a wearable device or system for diagnosing, detecting, and/or predicting a health condition or event (e.g. seizure, stroke, or heart attack) can comprise an arcuate module with at least one electrode (e.g. EEG sensor) which monitors and/or records electrical signals from a person's brain, wherein the module is removably-attached to eyewear (e.g. eyeglasses) worn by the person, and wherein the module has a rounded quadrilateral shape. In an example, a wearable device or system for diagnosing, detecting, and/or predicting a health condition or event (e.g. seizure, stroke, or heart attack) can comprise an arcuate module with at least one electrode (e.g. EEG sensor) which monitors and/or records electrical signals from a person's brain, wherein the module is removably-attached to eyewear (e.g. eyeglasses) worn by the person, and wherein the module has a crescent or kidney-bean shape.

In an example, a reference or ground electrode can be attached (e.g. clipped) to a person's ear lobe. In an example, an electrode (e.g. EEG sensor) can be attached (e.g. clipped) to a person's ear lobe. In an example, a system for monitoring and/or recording brainwaves can include eyewear with one or more electrodes and an earpiece (e.g. earbud) with one or more electrodes, wherein the eyewear and earpiece are in electromagnetic communication with each other. In an example, there can be at least two electrodes (e.g. EEG sensors) on each side (e.g. right and left) of eyewear (e.g. eyeglasses), wherein at least one of the electrodes is located anterior to (e.g. in front of) a person's auricle (outer ear) and at least one of the electrodes is located posterior to (e.g. behind or curving around the rear of) the person's auricle (outer ear).

In an example, an electrode can be a capacitive electrode. In an example, an electrode can be a single-pole electrode. In an example, an electrode can be based on impedance. In an example, an electrode can record and/or monitor brain waves. In an example, at least part of an electrode can be made with Thermoplastic PolyUrethane (TPU). In an example, at least part of an electrode can be made from a soft rubber and/or elastomer. In an example, data from electrodes can be filtered to remove muscle activity signals and isolate brain activity signals. In an example, electrodes can be in electromagnetic communication with a person's head. In an example, the side of an electrode (e.g. EEG sensor) which faces toward the surface of a person's head can have electroconductive ridges.

In an example, eyewear (e.g. eyeglasses) can include a power source (e.g. battery). In an example, eyewear can comprise EEG eyeglasses. In an example, eyewear can include a touch screen and/or display. In an example, a brow bar with one or more electrodes (e.g. EEG sensors) can be attached to the right and left rims of conventional eyewear (e.g. eyeglasses) in order to convert the conventional eyewear into smart eyewear which monitors (electrical and/or electromagnetic) brain activity. In an example, an electrode (e.g. EEG sensor) on eyewear (e.g. glasses) can be made with PDMS (polydimethylsiloxane) which has been impregnated, doped, filled, and/or coated with silver particles. In an example, an electrode (e.g. EEG sensor) on eyewear (e.g. eyeglasses) worn by a person can function as part of a BCI (brain-to-computer) interface by monitoring and/or recording electromagnetic signals from the person's brain (e.g. brainwaves).

In an example, data from electrodes can be partly processed (including amplification) locally within an eyewear frame and the further processed after transmission to a remote device. In an example, eyewear (e.g. eyeglasses) can include one or more inertial motion units (e.g. accelerometers, gyroscopes, and/or inclinometers) as well as electrodes (e.g. EEG sensors). In an example, eyewear (e.g. eyeglasses) can comprise electrodes (e.g. EEG sensors) which are in capacitive contact with a person's head. In an example, eyewear (e.g. eyeglasses) can include a data transmitter which transmits data from electrodes (e.g. EEG sensors) to a data processor in a separate device (e.g. a phone). In an example, eyewear (e.g. eyeglasses) which is worn by a person can comprise a plurality of electrodes (e.g. EEG sensors) which monitor and/or record the person's brainwaves.

In an example, eyewear (e.g. eyeglasses) worn by a person can incorporate one or more electrodes (e.g. EEG sensors) which monitor and/or record the person's brainwaves. In an example, eyewear (e.g. eyeglasses) worn by a person can include an electromagnetic mechanism which oscillates and/or vibrates an electrode (e.g. EEG sensor) to secure better electroconductive contact with the surface of the person's head. In an example, eyewear can include an extension (or attachment) to the eyewear front piece which holds one or more electrodes on a person's forehead above their eyes. In an example, eyewear can include an extension (or attachment) to the eyewear front piece which holds one or more electrodes above a person's eye.

In an example, eyewear can include two extensions (or attachments) to the eyewear front piece which hold electrodes on a person's forehead above the eyewear rims. In an example, eyewear with electrodes (e.g. EEG sensors) can include a transceiver/communication component. In an example, eyewear with electrodes (e.g. EEG sensors) can include a blood pressure sensor. In an example, eyewear with electrodes (e.g. EEG sensors) can be used for cognitive training. In an example, eyewear with electrodes can be used as a BCI (brain-to-computer interface) for navigating the internet. In an example, eyewear with one or more electrodes can include an analog-to-digital converter. In an example, eyewear with one or more electrodes can include a speaker and a microphone. In an example, eyewear with one or more electrodes can include a data processing unit (e.g., CPU, GPU, and/or memory).

In an example, eyewear with one or more electrodes can comprise a head-mounted display (HMD). In an example, eyewear with one or more electrodes (e.g. EEG sensors) worn by a person can collect data concerning brain wave activity which is used to evaluate the health (e.g. neurological or cardiovascular health) of the person. In an example, eyewear with one or more electrodes (e.g. EEG sensors) worn by a person can collect data concerning brain wave activity which is used to evaluate the person's alertness level. In an example, eyewear with one or more electrodes (e.g. EEG sensors) worn by a person can collect data concerning brain wave activity which is analyzed to evaluate the person's emotional state.

In an example, eyewear with one or more electrodes (e.g. EEG sensors) worn by a person can collect data concerning brain wave activity which is used to evaluate the person's response to a product or commercial for a product. In an example, one or more electrodes on eyewear (e.g. eyeglasses) can function as a neurostimulator. In an example, the amount by which an electrode (e.g. EEG sensor) extends inward from an eyewear frame toward the surface of a person's head can be adjusted by inflating or deflating a chamber which is between the electrode and the eyewear frame. In an example, the lenses of eyewear with electrodes can display virtual objects and/or project virtual objects in a person's view of the real world. In an example, the pressure exerted by an electrode (e.g. EEG sensor) on the surface of a person's head can be adjusted by rotating a threaded member which is between the electrode and the eyewear frame.

In an example, there can be compressible foam (or gel) between an electrode (e.g. EEG sensor) and an eyewear frame. In an example, eyewear (e.g. eyeglasses) for monitoring and/or recording EEG signals can include a substantially-transparent and flexible strap (e.g. strap, band, loop, or arm) which spans the middle of a person's forehead, from the right side of the forehead to the left side of the forehead, wherein there are at least two electrodes (e.g. EEG sensors) on the strap. In an example, eyewear (e.g. eyeglasses) worn by a person can include a downwardly-concave loop (e.g. loop, arch, wave, or arm) which is over (e.g. higher than) the rims of an eyewear front piece, wherein the loop spans from the right-side rim of the front piece to the left-side front piece, and wherein the loop holds at least two electrodes (e.g. EEG sensors) in electrical communication with the person's forehead.

In an example, eyewear (e.g. eyeglasses) worn by a person can include a right-side arch (e.g. arch, wave, arm, or loop) over (e.g. higher than) the right-side rim of an eyewear front piece and a left-side arch over the left-side rim of the front piece, wherein the right-side and left-side arches are approximately parallel to the person's eyebrows, and wherein each arch has at least one electrode (e.g. EEG sensor) which is in electrical communication with the person's forehead. In an example, eyewear (e.g. eyeglasses) worn by a person can include an upwardly-convex loop (e.g. loop, arch, wave, or arm) over (e.g. higher than) the right-side rim of an eyewear front piece and an upwardly-convex loop over the left-side rim of the front piece, wherein each loop holds at least one electrode (e.g. EEG sensor) in electrical communication with the person's forehead.

In an example, eyewear (e.g. eyeglasses) worn by a person can include a right-side arch (e.g. arch, wave, arm, or loop) over (e.g. higher than) the right-side rim of an eyewear front piece and a left-side arch over the left-side rim of the front piece, wherein each arch holds at least one electrode (e.g. EEG sensor) in electrical communication with the person's forehead. In an example, there can an arch (e.g. arch, loop, or arm) over each rim on an eyewear front piece (suggestive of upper eyebrows), wherein there is at least one electrode (e.g. EEG sensor) on each arch. In an example, an electrode can comprise a nonconductive elastomeric polymer that is sprayed with conductive material. In an example, an electrode can comprise electroconductive fibers (e.g. fibers, threads, or wires) which are embedded in an elastomeric polymer. In an example, an electrode can comprise non-electroconductive foam which is coated with electroconductive material.

In an example, at least part of an electrode can be made with a compressible, malleable, and/or low-durometer nonconductive material (e.g. a non-conductive elastomeric polymer) which has been impregnated, doped, and/or filled with a conductive material (e.g. carbon or metal particles). In an example, at least part of an electrode can be made from an elastomeric polymer which has been impregnated, doped, filled, and/or coated with a metal powder (e.g. silver, copper, gold, steel, or aluminum), graphite, or carbon nanotubes. In an example, electrodes can be separated from each other by insulating material.

In an example, an electrode (e.g. EEG sensor) on eyewear can be made from material with a Shore 00 value between 10 and 30. In an example, an electrode (e.g. EEG sensor) on eyewear (e.g. glasses) can be made with compressible, compliant, and/or elastomeric material. In an example, an electrode (e.g. EEG sensor) on eyewear (e.g. glasses) can be made with a silicone-based elastomeric polymer which has been impregnated, doped, filled, and/or coated with electroconductive material. In an example, a device or system for monitoring and/or recording EEG signals can include a module with at least one electrode (e.g. EEG sensor), whereon the module is removably-attached to eyewear (e.g. eyeglasses) behind a person's auricle (outer ear).

In an example, an electrode (or electrode module) can comprise two parallel components, a first component which is closer to the surface of a person's head and a second component which is farther from the surface of the person's head, wherein the first component is rotationally-oscillated (e.g. rotated back and forth in alternating clockwise and counter-clockwise directions) relative to the second component. In an example, an electrode (or electrode module) can be attached to an eyewear frame by parts on the electrode (or electrode module) and frame which snap together. In an example, an electrode (or electrode module) can be attached to an eyewear frame by magnetic parts on the electrode (or electrode module) and frame which plug together.

In an example, an electrode or electrode module can be attached to an eyewear frame by an adhesive. In an example, one or more electrode modules can be selectively and reversibly connected to different locations an eyewear frame. In an example, one or more electrode modules can be selectively and reversibly connected to different locations an eyewear frame, wherein connection provides an electronic connection between the eyewear frame and the module. In an example, there can be a solenoid between an electrode (or electrode module) and an eyewear frame. In an example, there can be compressible foam between an electrode (or electrode module) and an eyewear frame. In an example, a modular wearable device or system for monitoring and/or recording signals from a person's brain can include a cardioid, paint-palette, or lily-pad shaped module with an electrode (e.g. EEG sensor), wherein the module is removably-attached to an eyewear (e.g. eyeglasses) frame.

In an example, a wearable device or system for monitoring and/or recording signals from a person's brain can include an electrode (e.g. EEG sensor) module with a rounded square, rectangular, trapezoidal, or keystone shape which is removably-attached to an eyewear frame. In an example, a wearable device or system for monitoring and/or recording signals from a person's brain can include an electrode (e.g. EEG sensor) module with a cardioid, paint-palette, or lily-pad shape which is removably-attached to an eyewear frame.

In an example, a wearable device or system for predicting and detecting neurological seizures can comprise a module with at least one electrode (e.g. EEG sensor) which is removably-attached to the nose bridge of eyewear (e.g. eyeglasses). In an example, one or more electrodes can be located on the nose bridge of eyewear. In an example, a device or system for monitoring and/or recording EEG signals can include a module with at least one electrode (e.g. EEG sensor), whereon the module is removably-attached to the nose bridge and/or nose pads of eyewear. In an example, electrodes on eyewear which are anterior to an auricle can be substantially flat and electrodes on the eyewear which are posterior to the auricle can have a radial array of electroconductive protrusions (e.g. protrusions, prongs, teeth, legs, pins, and/or bumps).

In an example, eyewear (e.g. eyeglasses) worn by a person can comprise: a first plurality of substantially-flat electrodes (e.g. EEG sensors) which monitor electrical and/or electromagnetic signals from the person's brain from contact with areas of the person's head which are anterior to the person's auricles (e.g. auricles); and a second plurality of electrodes with protrusions (e.g. protrusions, prongs, teeth, legs, pins, and/or bumps) which monitor those signals from contact with areas of the person's head which are posterior to the person's auricles. In an example, a protrusion (e.g. protrusion, prong, tooth, leg, pin, and/or bump) which extends out from an electrode base toward the surface of a person's head can have a central nonconductive core and an outer electroconductive layer.

In an example, a protrusion (e.g. protrusion, prong, tooth, leg, pin, and/or bump) which extends out from an electrode base toward the surface of a person's head can comprise a central electroconductive core and an outer non-conductive layer, wherein the outer layer becomes thicker closer to the electrode base. In an example, a protrusion (e.g. protrusion, prong, tooth, leg, pin, and/or bump) which extends out from an electrode base toward the surface of a person's head can comprise a central nonconductive core and an outer electroconductive layer, wherein the outer layer becomes thicker farther from the electrode base. In an example, an electrode (e.g. EEG sensor) can comprise a base and a plurality of electroconductive protrusions (e.g. protrusions, prongs, teeth, legs, pins, and/or bumps) which extend out from the base toward the surface of a person's head, wherein the protrusions are tapered.

In an example, an electrode (e.g. EEG sensor) can comprise a base and a plurality of electroconductive protrusions (e.g. protrusions, prongs, teeth, legs, pins, and/or bumps) which extend out in a non-perpendicular manner from the base toward the surface of a person's head. In an example, an electrode (e.g. EEG sensor) can comprise abase and a plurality of electroconductive protrusions (e.g. protrusions, prongs, teeth, legs, pins, and/or bumps) which extend out from the base toward the surface of a person's head, wherein the diameters and/or cross-sectional perimeters of the protrusions decrease with distance from the base. In an example, an electrode (e.g. EEG sensor) can comprise a base and a plurality of electroconductive protrusions (e.g. protrusions, prongs, teeth, legs, pins, and/or bumps) which extend out from the base toward the surface of a person's head, wherein the angles at which the protrusions extend out from the base vary monotonically with the radial distance from the center of the base.

In an example, an electrode (e.g. EEG sensor) can comprise a base and a plurality of electroconductive protrusions (e.g. protrusions, prongs, teeth, legs, pins, and/or bumps) which extend out from the base toward the surface of a person's head, wherein the electroconductivity of the protrusions decreases with distance from the base. In an example, an electrode (e.g. EEG sensor) can comprise a base and a plurality of protrusions (e.g. protrusions, prongs, teeth, legs, pins, and/or bumps) which extend out from the base, wherein the protrusions are softer (e.g. more flexible and/or compliant) than the base. In an example, an electrode can comprise one or more electromagnetic actuators which move one or more protrusions (e.g. protrusions, prongs, teeth, legs, pins, and/or bumps) in a direction which is oblique to the surface of a person's head and/or to the surface of the base of the electrode, thereby enabling the protrusions to slide between strands of hair on the person's head.

In an example, an electrode can comprise one or more electromagnetic actuators which vibrate and/or oscillate one or more protrusions (e.g. protrusions, prongs, teeth, legs, pins, and/or bumps) in directions which are oblique to the surface of a person's head and/or to the surface of the base of the electrode, thereby enabling the protrusions to slide between strands of hair on the person's head. In an example, an electrode can comprise one or more electromagnetic actuators which move one or more protrusions (e.g. protrusions, prongs, teeth, legs, pins, and/or bumps) in a direction which is substantially parallel to the surface of a person's head and/or to the surface of the base of the electrode. In an example, an electrode can comprise a plurality of electromagnetic actuators, each of which moves a protrusion (e.g. protrusion, prong, teeth, leg, pin, and/or bump) which extends out from the electrode.

In an example, an electrode can have a base and plurality of protrusions (e.g. protrusions, prongs, teeth, legs, pins, and/or bumps) which extend out from the base, wherein a portion of a protrusion which is farther from the base is harder (less flexible and/or compliant) than a portion of the protrusion which is closer to the base. In an example, an electrode can include a plurality of spring-loaded protrusions (e.g. protrusions, prongs, teeth, legs, pins, and/or bumps) which extend out from an electrode base at angles which increase with the distance of a protrusion from the center of the electrode base. In an example, an electrode can include a plurality of protrusions (e.g. protrusions, prongs, teeth, legs, pins, and/or bumps) which extend out from the electrode base and which vibrate and/or oscillate along vectors which are substantially perpendicular to the electrode base.

In an example, an electrode can include a plurality of parallel spring-loaded protrusions (e.g. protrusions, prongs, teeth, legs, pins, and/or bumps). In an example, an electrode with a plurality of protrusions (e.g. protrusions, prongs, teeth, legs, pins, and/or bumps) can be rotationally oscillated (e.g. rotated back and forth in clockwise and counter-clockwise directions), which helps the protrusions to slide between strands of hair. In an example, the diameter of a protrusion (e.g. protrusion, prong, tooth, pin, or bump) which extends out from an electrode base can increase with distance from the electrode base. In an example, eyewear (e.g. eyeglasses) worn by a person can comprise: a first plurality of substantially-flat electrodes (e.g. EEG sensors) which monitor electrical and/or electromagnetic signals from the person's brain from contact with areas of the person's head which are not covered with hair; and a second plurality of electrodes with protrusions (e.g. protrusions, prongs, teeth, legs, pins, and/or bumps) which monitor those signals from contact with areas of the person's head which are covered with hair.

In an example, eyewear (e.g. eyeglasses) worn by a person can include a vibrating mechanism which vibrates an electrode (e.g. EEG sensor) with a plurality of electroconductive protrusions (e.g. protrusions, prongs, teeth, legs, pins, and/or bumps) to help the protrusions to penetrate between strands of hair on the person's head. In an example, eyewear (e.g. eyeglasses) worn by a person can include an electromagnetic mechanism which moves (e.g. moves, oscillates, and/or vibrates) an electrode (e.g. EEG sensor) in a reciprocating manner to help protrusions (e.g. protrusions, prongs, teeth, legs, pins, and/or bumps) on the sensor to penetrate between strands of hair on the person's head.

In an example, the base of an electrode (e.g. EEG sensor) can be made with material with a Shore 00 value between 10 and 30 and protrusions (e.g. protrusions, prongs, teeth, legs, pins, and/or bumps) extending out from that base can be made with material with a Shore 00 value between 30 and 80. In an example, an electrode (e.g. EEG sensor) on eyewear (e.g. glasses) can have protrusions (e.g. protrusions, prongs, teeth, legs, pins, and/or bumps) which are made from an elastomeric polymer which has been impregnated, doped, filled, and/or coated with electroconductive material.

In an example, an electrode (or electrode module) can comprise two parallel components, a first component with electroconductive protrusions (e.g. protrusions, prongs, teeth, legs, pins, and/or bumps) which is closer to the surface of a person's head and a second component which is farther from the surface of the person's head, wherein the first component is rotationally-oscillated (e.g. rotated back and forth in alternating clockwise and counter-clockwise directions) relative to the second component. In an example, an electrode (e.g. EEG sensor) on the anterior portion of an eyewear temple can be flat against the surface of a person's head and an electrode (e.g. EEG sensor) on the posterior portion of the temple can have a plurality electroconductive protrusions (e.g. protrusions, prongs, teeth, legs, pins, and/or bumps) which extend toward the surface of the person's head.

In an example, eyewear (e.g. eyeglasses) can comprise an arm or protrusion which extends upward from the eyewear temple, wherein one or more electrodes (e.g. EEG sensors) are on the arm or protrusion. In an example, the anterior longitudinal axis of an eyewear temple can have an upwardly-convex wave (e.g. wave, curve, bump, loop, and/or protrusion) on which an electrode (e.g. EEG sensor) is located. In an example, there can be a concave wave (e.g. wave, curve, bump, loop, and/or protrusion) in the anterior longitudinal axis of an eyewear temple and at least one electrode (e.g. EEG sensor) on the wave. In an example, there can be a concave wave (e.g. wave, curve, bump, loop, and/or protrusion) in the anterior longitudinal axis of an eyewear temple and at least one electrode (e.g. EEG sensor) on the wave, wherein the wave has a height between ½ and 3 inches. In an example, there can be an upward wave (wave, curve, bump, loop, and/or protrusion) in the anterior longitudinal axis of an eyewear temple and at least one electrode (e.g. EEG sensor) on the wave, wherein the wave has a height between ½ and 3 inches and a length between ½ and 3 inches.

In an example, there can be an upward wave (e.g. wave, curve, bump, loop, and/or protrusion) in the anterior third of the anterior longitudinal axis of an eyewear temple, wherein an electrode (e.g. EEG sensor) is located on the upward wave. In an example, the anterior longitudinal axis of an eyewear temple can have an upward wave (e.g. wave, curve, bump, loop, and/or protrusion) on which an electrode (e.g. EEG sensor) is located, wherein the wave has a sinusoidal shape (e.g. the shape of a complete sinusoidal cycle or a portion thereof). In an example, a wearable device or system for monitoring and/or recording signals from a person's brain can include an electrode (e.g. EEG sensor) with a rounded square, rectangular, trapezoidal, or keystone shape.

In an example, a wearable device or system for monitoring and/or recording signals from a person's brain can include an electrode (e.g. EEG sensor) with a cardioid, paint-palette, or lily-pad shape. In an example, the shape of an eyewear frame can be adjusted. In an example, the shape of an eyewear frame can be adjusted (e.g. custom fit to the contour of an individual's head) by changing the tension of a spring mechanism on the frame. In an example, eyewear can include an arcuate (e.g. downwardly-concave) extension (or attachment) to the eyewear front piece which holds one or more electrodes on a person's forehead above the eyewear rims. In an example, eyewear can include two arcuate (e.g. downwardly-concave) extensions (or attachments) to the eyewear front piece which hold electrodes on a person's forehead above the eyewear rims.

In an example, eyewear (e.g. eyeglasses) worn by a person can include a crescent-or-parenthesis-shaped right-side arch (e.g. arch, wave, arm, or loop) over (e.g. higher than) the right-side rim of an eyewear front piece and a crescent-or-parenthesis-shaped left-side arch over the left-side rim of the front piece, wherein each arch has at least one electrode (e.g. EEG sensor) which is in electrical communication with the person's forehead. In an example, a wearable device or system for diagnosing, detecting, and/or predicting a health condition or event (e.g. seizure, stroke, or heart attack) can comprise: a right-side module which is removably-attached to the right-side temple of eyewear (e.g. eyeglasses), wherein the right-side module includes at least one electrode (e.g. EEG sensor); and a left-side module which is removably-attached to the left-side temple of eyewear, wherein the left-side module includes at least one electrode.

In an example, a temple (e.g. side section) of eyewear (e.g. eyeglasses) can span forward from the rear of a person's auricle (e.g. outer ear) in the following manner: start with a posterior (rear) end which is worn posterior to (behind) the person's auricle; then curve upward and forward around the tissue connection between the person's outer auricle and the rest of the person's head, to the top of this tissue connection; then curve downward and forward; then curve upward, forward, and inward to a location on the person's temple and/or forehead; and then curve downward, forward, and outward to an anterior (front) end which connects to (or becomes part of) a front piece (e.g. front section) of the eyewear. In an example, the temple can hold an electrode (e.g. EEG sensor and/or electromagnetic energy sensor) on a person's head.

In an example, a temple (e.g. side section) of eyewear (e.g. eyeglasses) can span forward from the rear of a person's auricle (e.g. outer ear) in the following manner: start with a posterior (rear) end which is worn posterior to (behind) the person's auricle; then curve upward and forward around the tissue connection between the person's outer auricle and the rest of the person's head, to the top of this tissue connection; then curve downward and forward 1"-3"; then curve upward, forward, and inward 1"-3" to a location on the person's temple and/or forehead; and then curve downward, forward, and outward to an anterior (front) end which connects to (or becomes part of) a front piece (e.g. front section) of the eyewear. In an example, the temple can hold an electrode (e.g. EEG sensor and/or electromagnetic energy sensor) on a person's head.

In an example, eyewear (e.g. eyeglasses) with electrodes (e.g. EEG sensors and/or electromagnetic energy sensors) can comprise: an eyewear frame which further comprises a front piece (e.g. front section) which spans the front of a person's head, a first temple (e.g. side section) which spans from a first auricle (e.g. outer ear) to the front piece, and a second temple which spans from a second auricle to the front piece; a plurality of arcuate (sinusoidal) protrusions which are part of, or attached to, a temple; a plurality of electrodes which collect data concerning brain activity, wherein the plurality of protrusions hold the plurality of electrodes on the person's head; an energy source; a data processor; and a data transmitter and/or receiver. In an example, protrusions can be made from compressible foam or filled with a gas or liquid. In an example, extension of the protrusions can be adjusted by adjusting the amounts and/or pressures of gases or liquids inside them.

In an example, eyewear (e.g. eyeglasses) with electrodes (e.g. EEG sensors and/or electromagnetic energy sensors) can comprise: an eyewear frame which further comprises a front piece (e.g. front section) which spans the front of a person's head; a first temple (e.g. side section) which spans from a first auricle (e.g. outer ear) to the front piece; a second temple which spans from a second auricle to the front piece; an arcuate tensile protrusion which is part of, or attached to, a temple; an electrode which collects data concerning brain activity, wherein the protrusion holds the electrode on the person's head; an energy source; a data processor; and a data transmitter and/or receiver. In an example, the posterior (rear) end of this protrusion can be directly attached to the temple and the anterior end of the protrusion is not directly attached to the temple. In an example, this protrusion can have a half-sinusoidal shape.

In an example, eyewear (e.g. eyeglasses) with electrodes (e.g. EEG sensors and/or electromagnetic energy sensors) can comprise: an eyewear frame which further comprises a front piece (e.g. front section) which spans the front of a person's head, a first temple (e.g. side section) which spans from a first auricle (e.g. outer ear) to the front piece, and a second temple which spans from a second auricle to the front piece; an arcuate tensile protrusion which is part of, or attached to, a selected temple; an electrode which collects data concerning brain activity; wherein the protrusion holds the electrode on the person's head; an energy source; a data processor; and a data transmitter and/or receiver. In an example, there can be a spring between the anterior (front) end of the arcuate protrusion and the selected temple.

In an example, eyewear (e.g. eyeglasses) with electrodes (e.g. EEG sensors and/or electromagnetic energy sensors) can comprise: an eyewear frame which further comprises a front piece (e.g. front section) which spans the front of a person's head; a first temple (e.g. side section) which spans from a first auricle (e.g. outer ear) to the front piece; a second temple which spans from a second auricle to the front piece; an arcuate tensile protrusion which is part of, or attached to, a temple; an electrode which collects data concerning brain activity, wherein the protrusion holds the electrode on the person's head; an energy source; a data processor; and a data transmitter and/or receiver. In an example, both the posterior (rear) end and the anterior (front) end of the arcuate tensile protrusion can be directly attached to the temple, but the middle of the arcuate tensile protrusion between these ends is not directly attached to the temple.

In an example, eyewear (e.g. eyeglasses) with electrodes (e.g. EEG sensors and/or electromagnetic energy sensors) can comprise: an eyewear frame which further comprises a front piece (e.g. front section) which spans the front of a person's head, a first temple (e.g. side section) which spans from a first auricle (e.g. outer ear) to the front piece; a second temple which spans from a second auricle to the front piece; an arcuate tensile protrusion which is part of, or attached to, the selected temple; an electrode which collects data concerning brain activity, wherein the protrusion holds the electrode on the person's head; an energy source; a data processor; and a data transmitter and/or receiver. In an example: both the posterior (rear) end and the anterior (front) end of the arcuate tensile protrusion can be directly attached to the temple; and there can be a spring between the middle portion of the arcuate tensile protrusion and the temple.

In an example, the extension of a flexible protrusion which holds an electrode (e.g. EEG sensor and/or electromagnetic energy sensor) on a person's head can be adjusted. In an example, eyewear (e.g. eyeglasses) with electrodes (e.g. EEG sensors and/or electromagnetic energy sensors) can comprise: an eyewear frame which further comprises front piece (e.g. front section) which spans the front of a person's head, a first temple (e.g. side section) which spans from a first auricle (e.g. outer ear) to the front piece; a second temple which spans from a second auricle to the front piece; a flexible protrusion which is part of, or attached to, a temple; an electrode which collects data concerning brain activity; wherein the protrusion holds the electrode on the person's head; an energy source; a data processor; a data transmitter and/or receiver; and a knob (e.g. knob, button, pin, or clip).

In an example, the flexible protrusion can have a first configuration in which it extends a first distance from a temple toward a person's head and have a second configuration in which it extends a second distance from the temple toward the person's head, wherein the second distance is greater than the first distance, and wherein the flexible protrusion is reversibly moved from the first configuration to the second configuration by moving (e.g. sliding or turning) the knob.

In an example, a flexible protrusion can be adjusted (moved or changed) from its first configuration to its second configuration by manually moving sliding the knob, which moves one end of the flexible protrusion closer to the other end of the flexible protrusion and causes the middle of the flexible protrusion to bulge (further) towards toward the person's head. In an example, one end of the flexible protrusion can be slid closer to the other end along a track or channel, thereby causing the middle of the flexible protrusion to bulge (further) outwards toward the person's head. In another example, a flexible protrusion can be automatically moved from its first configuration to its second configuration by an actuator.

In an example, eyewear (e.g. eyeglasses) with electrodes (e.g. EEG sensors and/or electromagnetic energy sensors) can comprise: an eyewear frame which further comprises front piece (e.g. front section) which spans the front of a person's head; a first temple (e.g. side section) which spans from a first auricle (e.g. outer ear) to the front piece; a second temple which spans from a second auricle to the front piece; a folded and/or pleated protrusion which is part of, or attached to, a temple; an electrode (e.g. EEG sensor and/or electromagnetic energy sensor) which collects data concerning brain activity, wherein the protrusion holds the electrode on the person's head; an energy source; a data processor; and a data transmitter and/or receiver. In an example, a folded and/or pleated protrusion can be extended (further) from the temple toward the person's head by filling the protrusion with a gas or liquid. In an example, the folded and/or pleated protrusion can be shaped like a bellows or accordion.

In an example, eyewear (e.g. eyeglasses) with electrodes (e.g. EEG sensors and/or electromagnetic energy sensors) can comprise: an eyewear frame which further comprises a front piece (e.g. front section) which spans the front of a person's head; a first temple (e.g. side section) which spans from a first auricle (e.g. outer ear) to the front piece; a second temple which spans from a second auricle to the front piece; a pivoting protrusion (e.g. protrusion or arm) which is part of, or attached to, the selected temple; an electrode which collects data concerning brain activity; wherein the protrusion holds the electrode on the person's head; an energy source; a data processor; and a data transmitter and/or receiver. In an example, there can be a spring between the pivoting protrusion and the temple.

In an example, eyewear (e.g. eyeglasses) with electrodes (e.g. EEG sensors and/or electromagnetic energy sensors) can comprise: an eyewear frame which further comprises a front piece (e.g. front section) which spans the front of a person's head; a first temple (e.g. side section) which spans from a first auricle (e.g. outer ear) to the front piece; and a second temple which spans from a second auricle to the front piece; a wedge-shaped flexible protrusion which is part of, or attached to, a temple; an electrode which collects data concerning brain activity, wherein the protrusion holds the electrode on the person's head; an energy source; a data processor; and a data transmitter and/or receiver. In an example, the wedge-shaped protrusion can be made from compressible foam.

In an example, eyewear (e.g. eyeglasses) with electrodes (e.g. EEG sensors and/or electromagnetic energy sensors) can comprise: an eyewear frame which further comprises a front piece (e.g. front section) which spans the front of a person's head; a first temple (e.g. side section) which spans from a first auricle (e.g. outer ear) to the front piece; a second temple which spans from a second auricle to the front piece; a wedge-shaped flexible protrusion which is part of, or attached to, a temple; an electrode which collects data concerning brain activity, wherein the protrusion holds the electrode on the person's head; an energy source; a data processor; a data transmitter and/or receiver; and a pump. In an example, the wedge-shaped protrusion can be inflated or deflated by activation of the pump.

In example, eyewear (e.g. eyeglasses) with electrodes (e.g. EEG sensors and/or electromagnetic energy sensors) can comprise: a frame for eyewear, wherein this frame further comprises a front piece which spans the front of a person's head; a first temple (e.g. side section) which spans from a first auricle (e.g. outer ear) to the front piece; a second temple which spans from a second auricle to the front piece; wherein the first temple starts with a posterior end which is worn posterior to a person's auricle, then curves upward and forward around the tissue connection between the person's outer auricle and the rest of the person's head to the top of this tissue connection, then curves downward and forward, then curves upward, forward, and inward to a location over the person's temple and/or forehead, and then curves downward, forward, and outward to connect to the front piece; a flexible protrusion which is part of, or attached to, the temple; an electrode which collects data concerning brain activity, wherein the flexible protrusion holds the electrode on the person's head; an energy source; a data processor; and a data transmitter and/or receiver.

In an example, eyewear (e.g. eyeglasses) with electrodes (e.g. EEG sensors and/or electromagnetic energy sensors) can comprise: a front piece (e.g. front section) of an eyewear frame which spans the front of a person's face; a temple (e.g. side section) of the eyewear frame which spans: forward from one of the person's auricles (e.g. outer ears); then upward, forward, and inward (toward the center of the person's forehead) to a location on the person's forehead (above one of the person's eyes); then downward, backward, and outward (away from the center of the person's forehead); and then forward to connect to the front piece; and at least one electrode which collects data concerning brain activity which is attached to the temple. In an example, the eyewear from can include a second temple with a similar configuration.

In an example, eyewear with electrodes can comprise: a front piece of an eyewear frame which spans the front of a person's face; a temple of the eyewear frame, wherein the temple spans forward from one of the person's auricles, then spans upward, forward, and inward toward the center of the person's forehead to a location on the person's forehead, then spans downward, backward, and outward away from the center of the person's forehead, and then spans forward to connect to the front piece; and at least one electrode on the temple, wherein the electrode collects data concerning brain activity.

This example of eyewear (e.g. eyeglasses) with electrodes (e.g. EEG sensors and/or electromagnetic energy sensors) can also be described as comprising: a front piece (e.g. front section) of an eyewear frame which spans the front of a person's face; a temple (e.g. side section) of the eyewear frame which includes an upward loop which is configured to curve upward, forward, and inward (toward the center of the person's forehead) to a location on the person's forehead (above one of the person's eyes) and then curve downward, backward, and outward (away from the center of the person's forehead); and at least one electrode which collects data concerning brain activity which is attached to the temple. In an example, the eyewear from can include a second temple with a similar configuration.

This example of eyewear (e.g. eyeglasses) with electrodes (e.g. EEG sensors and/or electromagnetic energy sensors) can also be described as comprising: a front piece (e.g. front section) of an eyewear frame which spans the front of a person's face; a temple (e.g. side section) of the eyewear frame with an arcuate zigzag portion, wherein this arcuate zigzag portion is configured to span forward (to a location on the person's forehead above one of the person's eyes), then span backward (to a location over the person's temple), and then span forward again to connect to the front piece; and at least one electrode which collects data concerning brain activity which is attached to the temple. In an example, the eyewear from can include a second temple with a similar configuration.

This example of eyewear (e.g. eyeglasses) with electrodes (e.g. EEG sensors and/or electromagnetic energy sensors) can also be described as comprising: a front piece (e.g. front section) of an eyewear frame which spans the front of a person's face; a temple (e.g. side section) of the eyewear frame with an arcuate zigzag portion, wherein this arcuate zigzag portion is configured to span forward and upward (to a location on the person's forehead above one of the person's eyes), then span backward and downward, and then span forward to connect to the front piece; and at least one electrode which collects data concerning brain activity which is attached to the temple. In an example, the eyewear from can include a second temple with a similar configuration.

This example of eyewear (e.g. eyeglasses) with electrodes (e.g. EEG sensors and/or electromagnetic energy sensors) can also be described as comprising: a front piece (e.g. front section) of an eyewear frame which spans the front of a person's face; a temple (e.g. side section) of the eyewear frame with an arcuate zigzag portion, wherein this arcuate zigzag portion is configured to span forward, upward, and inward toward the center of the person's forehead (to a location on the person's forehead above one of the person's eyes), then span backward, downward, and outward away from the center of the person's forehead, and then span forward to connect to the front piece; and at least one electrode which collects data concerning brain activity which is attached to the temple. In an example, the eyewear from can include a second temple with a similar configuration.

In an example, eyewear (e.g. eyeglasses) with electrodes (e.g. EEG sensors and/or electromagnetic energy sensors) can comprise: a front piece (e.g. front section) of an eyewear frame; a first temple (e.g. side section) of the eyewear frame, wherein the first temple spans from one of the person's auricles (e.g. outer ears) to the front piece of the eyewear frame, wherein the first temple includes a loop which curves upward, forward, and inward (closer to the center of the person's forehead) to a location on the person's forehead (above an eye) and then curves downward, backward, and outward (farther from the center of the person's forehead); a first flexible protrusion on the first temple; a first electrode which collects data concerning brain activity on the first flexible protrusion; a first energy source; a first data processor; a first data transmitter and/or receiver; a second temple of the eyewear frame, wherein the second temple spans from one of the person's auricles to the front piece of the eyewear frame, wherein the second temple includes a loop which curves upward, forward, and inward (closer to the center of the person's forehead) to a location on the person's forehead (above an eye) and then curves downward, backward, and outward (farther from the center of the person's forehead); a second flexible protrusion on the second temple; a second electrode which collects data concerning brain activity on the second flexible protrusion; a second energy source; a second data processor; and a second data transmitter and/or receiver.

In an example, there can be an energy source, a data processor, and a data transmitter and/or receiver on each temple (e.g. side section). In an example, there can be an energy source, data processor, and data transmitter and/or receiver on only one temple. In an example, a flexible protrusion and/or an electrode (e.g. EEG sensor and/or electromagnetic energy sensor) can be attached to a portion of a temple which is located on the person's forehead above an eye. In an example, there can be only one electrode on a temple. In an example, there can be two or more electrodes on a temple.

In an example, a temple (e.g. side section) can extend inward toward the center of a person's forehead. In an example, there can be two electrodes (e.g. EEG sensors and/or electromagnetic energy sensors) on each temple. In an example, inward loops of right-side and left-temples can be separated by a distance of 5" or less (across a person's forehead). In an example, inward loops of right-side and left-temples can be separated by a distance of 3" or less (across a person's forehead).

In an example, eyewear (e.g. eyeglasses) with electrodes (e.g. EEG sensors and/or electromagnetic energy sensors) can comprise: a front piece (e.g. front section) of an eyewear frame; a first temple (e.g. side section) of the eyewear frame, wherein the first temple spans from one of the person's auricles (e.g. outer ears) to the front piece of the eyewear frame, wherein the first temple includes a loop which curves upward, forward, and inward (closer to the center of the person's forehead) to a location on the person's forehead (above an eye) and then curves downward, backward, and outward (farther from the center of the person's forehead); first and second flexible protrusions on the first temple; first and second electrodes which collect data concerning brain activity on the first flexible protrusion; a first energy source; a first data processor; a first data transmitter and/or receiver; a second temple of the eyewear frame, wherein the second temple spans from one of the person's auricles to the front piece of the eyewear frame, wherein the second temple includes a loop which curves upward, forward, and inward (closer to the center of the person's forehead) to a location on the person's forehead (above an eye) and then curves downward, backward, and outward (farther from the center of the person's forehead); third and fourth flexible protrusions on the second temple; third and fourth electrodes which collect data concerning brain activity on the second flexible protrusion; a second energy source; a second data processor; and a second data transmitter and/or receiver.

In an example, eyewear temples (e.g. side sections) can each include a direct link which connects the ends of a forward-upward loop. This creates a bifurcation in a temple: with a first branch of the temple extending forward, upward, and inward to a location on the person's forehead; and a second branch of the temple extending in a relatively straight manner from the person's auricle (e.g. outer ear) to the front sector of the eyewear frame.

In an example, eyewear (e.g. eyeglasses) with electrodes (e.g. EEG sensors and/or electromagnetic energy sensors) can comprise: a front piece (e.g. front section) of an eyewear frame; a first temple (e.g. side section) of the eyewear frame, wherein the first temple spans from one of the person's auricles (e.g. outer ears) to the front piece of the eyewear frame, wherein the first temple includes a loop which curves upward, forward, and inward (closer to the center of the person's forehead) to a location on the person's forehead (above an eye) and then curves downward, backward, and outward (farther from the center of the person's forehead); first and second flexible protrusions on the first temple; first and second electrodes which collect data concerning brain activity on the first flexible protrusion; a first energy source; a first data processor; a first data transmitter and/or receiver; a second temple of the eyewear frame, wherein the second temple spans from one of the person's auricles to the front piece of the eyewear frame, wherein the second temple includes a loop which curves upward, forward, and inward (closer to the center of the person's forehead) to a location on the person's forehead (above an eye) and then curves downward, backward, and outward (farther from the center of the person's forehead); third and fourth flexible protrusions on the second temple; third and fourth electrodes which collect data concerning brain activity on the second flexible protrusion; a second energy source; a second data processor; and a second data transmitter and/or receiver.

In an example, eyewear (e.g. eyeglasses) with electrodes (e.g. EEG sensors and/or electromagnetic energy sensors) can comprise: a front piece (e.g. front section) of an eyewear frame which spans the front of a person's face; a temple (e.g. side section) of the eyewear frame which is configured to: span forward from one of the person's auricles (e.g. outer ears); then span upward, forward, and inward toward the center of the person's forehead to a location on the person's forehead above one of the person's eyes; then span downward, backward, and outward away from the center of the person's forehead; and then span forward to connect to the front piece; and at least one electrode which is attached to the temple which collects data concerning brain activity.

In an example, a wearable device or system for diagnosing, detecting, and/or predicting a health condition or event (e.g. seizure, stroke, or heart attack) can include a module which is removably-attached by adhesion to an eyewear temple worn by a person, wherein the module includes at least one electrode (e.g. EEG sensor). In an example, a wearable device or system for diagnosing, detecting, and/or predicting a health condition or event (e.g. seizure, stroke, or heart attack) can include a module which is removably-attached by a magnet to an eyewear temple worn by a person, wherein the module includes at least one electrode (e.g. EEG sensor). In an example, a wearable device or system for predicting and detecting neurological seizures can comprise a module with at least one electrode (e.g. EEG sensor) which is removably-attached to the temple of eyewear (e.g. eyeglasses).

In an example, a wearable device or system for diagnosing, detecting, and/or predicting a health condition or event (e.g. seizure, stroke, or heart attack) can include a module which is removably-attached by one or more elastic bands (or strips) to an eyewear temple worn by a person, wherein the module includes at least one electrode (e.g. EEG sensor). In an example, a wearable device or system for predicting and detecting neurological seizures can comprise an arcuate module with at least two electrodes (e.g. EEG sensors) which monitor and/or record electrical signals from a person's brain, wherein the module is removably-attached to eyewear (e.g. eyeglasses) worn by the person, wherein at least one of the electrodes is higher where the module is attached to the temple, and at least one of the electrodes is below where the module is attached to the temple. In an example, a wearable device or system for predicting and detecting neurological seizures can comprise an arcuate module with at least one electrode (e.g. EEG sensor) which monitors and/or records electrical signals from a person's brain, wherein the module is removably-attached to eyewear (e.g. eyeglasses) worn by the person, and wherein part of the module is higher than the temple and part of the module is lower than the temple.

In an example, a wearable device or system for predicting and detecting neurological seizures can comprise an arcuate module with at least one electrode (e.g. EEG sensor) which monitors and/or records electrical signals from a person's brain, wherein the module is removably-attached to eyewear (e.g. eyeglasses) worn by the person, and wherein at least 75% of the module is extends above the location where it is attached to the temple. In an example, the central longitudinal axis of the section of a temple (e.g. sidepiece) of an eyewear (e.g. eyeglasses) frame which extends from a person's auricle (outer ear) to the front piece of the eyewear can include an upwardly-convex wave or curve. In an example, the section of a temple (e.g. sidepiece) of an eyewear (e.g. eyeglasses) frame which extends from a person's auricle (outer ear) to the front piece of the eyewear can include an upward wave or curve.

In an example, the section of a temple (e.g. sidepiece) of an eyewear (e.g. eyeglasses) frame which extends from a person's auricle (outer ear) to the front piece of the eyewear can bifurcate. In an example, a temple (also called a sidepiece, bow, arm, or leg) of eyewear (e.g. eyeglasses) rests on a person's auricle (e.g. outer ear) at a first location which is at a first height (when the person is standing upright), a first electrode (e.g. EEG sensor) is on the temple is at a second location which is at a second height, and a second electrode is on the temple at a third location which is at a third height, wherein the second height is between ½ and 3 inches above the first height, and wherein the third height is between ½ and 3 inches below the first height.

In an example, a temple (also called a sidepiece, bow, arm, or leg) of eyewear (e.g. eyeglasses) rests on a person's auricle (e.g. outer ear) at a first location which is at a first height (when the person is standing upright), a first electrode (e.g. EEG sensor) is on the temple at a second location which is at a second height, and a second electrode is on the temple at a third location which is at a third height, wherein the second height is above the first height, and wherein the third height is above the first height.

In an example, a temple (also called a sidepiece, bow, arm, or leg) of eyewear (e.g. eyeglasses) rests on a person's auricle (e.g. outer ear) at a first location which is at a first height (when the person is standing upright), a first electrode (e.g. EEG sensor) is on the temple at a second location which is at a second height, and a second electrode is on the temple at a third location which is at a third height, wherein the second height is between ½ and 3 inches above the first height, wherein the third height is between ½ and 3 inches above the first height, wherein the second location is anterior to the first location, and wherein the third location is posterior to the first location.

In an example, the anterior section of an eyewear temple can extend from a person's auricle (outer ear) to the front piece of the eyewear, wherein the central third of this anterior section bifurcates into an upper branch and a lower branch, wherein there is at least one electrode (e.g. EEG sensor) on the upper branch. In an example, there can be at least three electrodes (e.g. EEG sensors) on an eyewear temple, wherein at least two electrodes are anterior to (e.g. in front of) the person's auricle (outer ear) and one electrode is posterior to (e.g. behind or curved around the rear of) the person's auricle. In an example, there can be at least two electrodes (e.g. EEG sensors) on an eyewear temple, wherein at least one electrode is higher than the top of the person's auricle (outer ear) and at least one electrode is below the top of the person's auricle.

In an example, there can be at least two electrodes (e.g. EEG sensors) on an eyewear temple, wherein at least one electrode is at least ½ inch higher than the top of the person's auricle (outer ear) and at least one electrode is below the top of the person's auricle. In an example, there can be at least two electrodes (e.g. EEG sensors) on a right-side eyewear temple worn by a person, wherein at least one of the electrodes is anterior to (e.g. in front of) the person's right auricle (outer ear) and at least one of the electrodes is posterior to (e.g. behind or curved around the rear of) the person's right auricle. In an example, the section of a temple (e.g. sidepiece) of an eyewear (e.g. eyeglasses) frame which extends from a person's auricle (outer ear) to the front piece of the eyewear can be arcuate.

In an example, the curvature of the posterior portion of an eyewear temple can be adjusted (e.g. custom fit to the contour of an individual's head) by heating and cooling this portion. In an example, the tension of a spring in the connection between an eyewear front piece and eyewear temple can be adjusted. In an example, a foam piece between the temple of eyewear and an electrode can be made by 3D printing. In an example, an electrode (e.g. EEG sensor) can slide along a longitudinal track (or channel) on the side of an eyewear temple which faces toward the surface of a person's head. In an example, an electrode (e.g. EEG sensor) can be part of (or removably-attached to) the anterior third of an eyewear temple worn by a person, wherein the electrode monitors and/or records electromagnetic signals from the person's brain (e.g. brainwaves). In an example, an electrode (e.g. EEG sensor) can be attached to an eyewear temple by two or more tension-adjustable springs.

In an example, an electrode (e.g. EEG sensor) can be attached to an eyewear temple by two or more springs with different-size radii. In an example, an electrode (e.g. EEG sensor) can be attached to an eyewear temple by two or more springs with different elasticities. In an example, an electrode (e.g. EEG sensor) can be attached to an eyewear temple by two or more springs which intersect (e.g. at connected to) the temple at different angles. In an example, an electrode (e.g. EEG sensor) can be attached to an eyewear temple by a spring inside compressible foam. In an example, an electrode (or movable component holding an electrode) can have a first configuration in which it is aligned with the temple of eyewear and a second configuration in which it is extends above the temple, wherein the electrode (or component) is moved from its first configuration to its second configuration by being pivoted, rotated, unfolded, or bent.

In an example, an eyewear frame can include a pivoting and/or rotating arm with one or more electrodes on it, wherein the arm has a first configuration in which it is aligned with an eyewear temple and a second configuration in which it extends out from the temple. In an example, an eyewear temple can have a (central) wave (e.g. wave, arch, and/or curve) which curves upward from the rest of the temple and inward toward the surface of a person's head, wherein there are one or more electrodes (e.g. EEG sensors) on the central wave. In an example, an eyewear temple can have a (central) wave (e.g. wave, arch, and/or curve) which curves upward from the rest of the temple and forward to span across a person's forehead, wherein there are one or more electrodes (e.g. EEG sensors) on the central wave.

In an example, an eyewear temple can comprise of a longitudinal series of linked segments, wherein one or more of the segments includes one or more electrodes (e.g. EEG sensors) for measuring brain activity. In an example, eyewear (e.g. eyeglasses) can comprise six electrodes (e.g. EEG sensors): one sensor on the anterior portion of the right temple, one sensor on the posterior portion of the right temple, one sensor on the anterior portion of the left temple, one sensor on the posterior portion of the left temple, one sensor the right side of the front piece, and one sensor on the left side of the front piece.

In an example, eyewear (e.g. eyeglasses) worn by a person can have temples with electrodes (e.g. EEG sensors) on them, wherein the temples are connected to a front piece by spring-loaded hinges which press (or pull) the temples inward toward the surface of the person's head, thereby pressing the electrodes onto the surface of the person's head, and wherein the tension of the springs can be adjusted to adjust the force with which the electrodes are pressed onto the surface of the person's head. In an example, one or more electrodes can be printed onto an eyewear temple using electroconductive ink. In an example, one or more electrodes (or arms with one or more electrodes) can have a first configuration in which they are recessed onto or within an eyewear temple and a second configuration in which they extend out from the temple in order to contact the surface of a person's head, wherein the electrodes are changed from their first configuration to their second configuration (or vice versa) by one or more solenoids.

In an example, one or more electrodes (or arms with one or more electrodes) can have a first configuration in which they lay flat against the temple of eyewear and a second configuration in which they extend out from the temple in order to contact the surface of a person's head, wherein the electrodes pivot, rotate, and/or fold out from the temple in order to change from their first configuration to their second configuration. In an example, the central third of the anterior portion of the temple of eyewear can be at least 50% wider than the anterior and posterior thirds of the anterior portion in order to allow placement of one or more electrodes at locations which are higher than the anterior and posterior thirds of the anterior portion. In an example, the location of an electrode (e.g. EEG sensor) on the temple of eyewear can be adjusted (in an anterior direction or in a posterior direction) by moving (e.g. sliding) the electrode (e.g. EEG sensor) along a longitudinal track or channel on the temple.

In an example, the tension of a hinge which connects a front piece of eyewear to an eyewear temple can be manually adjusted in order to adjust the contact pressure of between one or more electrodes on the temple and a person's head. In an example, there can be at least three electrodes (e.g. EEG sensors) on the right-side eyewear temple and at least three electrode on the left-side temple of the eyewear. In an example, there can be at least two electrodes (e.g. EEG sensors) on a right-side eyewear temple and at least two electrodes on a left-side eyewear temple.

In an example, a strap (e.g. strap, band, loop, or arm) which loops over the top (e.g. the upper third) of a person's head can be attached to the right-side and left-side temples of eyewear (e.g. eyeglasses), wherein there is at least one electrode (e.g. EEG sensor) on the strap. In an example, a strap (e.g. strap, band, loop, or arm) which loops over the top (e.g. the upper third) of a person's head can be attached by (tension-adjustable) spring mechanisms to the right-side and left-side temples of eyewear (e.g. eyeglasses), wherein there is at least one electrode (e.g. EEG sensor) on the strap. In an example, an eyewear temple can have a (central) wave (e.g. wave, arch, loop, or bend) which curves upward from the rest of the temple, wherein there are one or more electrodes (e.g. EEG sensors) on the central wave and/or arch.

In an example, an upper band (e.g. band, strap, or arm) which loops over the top (e.g. the upper third) of a person's head can be attached to the central-longitudinal-third of a right-side eyewear temple and to the central-longitudinal-third of a left-side eyewear temple, wherein there is at least one electrode (e.g. EEG sensor) on the band. In an example, eyewear (e.g. eyeglasses) for monitoring and/or recording EEG signals can include a strap (e.g. strap, band, loop, or arm) which spans the middle of a person's forehead, from the right side of the forehead to the left side of the forehead, wherein there are at least two electrodes (e.g. EEG sensors) on the strap, and wherein the strap is connected to the right side and left side temples of the eyewear. In an example, eyewear (e.g. eyeglasses) can comprise a loop or wave which extends upward from the eyewear temple, wherein one or more electrodes (e.g. EEG sensors) are on the loop or wave.

In an example, eyewear can comprise a flexible band (e.g. band, arm, strap, or strip), wherein the band includes one or more electrodes, wherein the band has a first configuration in which it is retracted (e.g. coiled) onto or within an eyewear temple and a second configuration in which it is extended (e.g. uncoiled) from the temple and loops over the top (e.g. the upper third) of the person's head. In an example, eyewear can comprise a flexible band (e.g. band, arm, strap, or strip) which spans a person's forehead from one temple of the eyewear to the other, wherein there are two or more electrodes (e.g. EEG sensors) on the band.

In an example, an electrode (e.g. EEG sensor) on the anterior portion of an eyewear temple can be made with material with a Shore 00 value between 10 and 30 and an electrode (e.g. EEG sensor) on the posterior portion of the eyewear temple can be made with material with a Shore 00 value between 30 and 80. In an example, a device or system for monitoring and/or recording EEG signals can include a module with at least one electrode (e.g. EEG sensor), whereon the module is removably-attached to the anterior portion of an eyewear temple. In an example, a system or device for monitoring and/or recording brain activity can comprise a module with at least one electrode (e.g. EEG sensor), wherein the module is plugged (e.g. plugged, inserted, or snapped) into one of a plurality of different slots (e.g. slots, receptacles, or openings) along the temple (e.g. sidepiece) of eyewear.

In an example, a wearable device or system for monitoring and/or recording signals from a person's brain can include a module with at least one electrode (e.g. EEG sensor), wherein the module is removably-attached to an eyewear temple, and wherein the module spans between 35% and 60% of the anterior portion of the temple. In an example, a wearable device or system for monitoring and/or recording signals from a person's brain can include a module with at least one electrode (e.g. EEG sensor), wherein the module is removably-attached to an eyewear temple, and wherein the module (e.g. the electrode on the module) is pressed against the surface of the person's head by a (tension-adjustable) spring between the module and the temple.

In an example, a wearable device or system for monitoring and/or recording signals from a person's brain can include a module with at least one electrode (e.g. EEG sensor), wherein the module is removably-attached to an eyewear temple, and wherein the module (e.g. the electrode on the module) is pressed against the surface of the person's head by a length-adjustable solenoid between the module and the temple. In an example, a wearable device or system for monitoring and/or recording signals from a person's brain can include a module with at least one electrode (e.g. EEG sensor), wherein the module is removably-attached to an eyewear temple, and wherein the electrode is pressed against the surface of the person's head by an anterior (tension-adjustable) spring between the electrode and the module and by a posterior (tension-adjustable) spring between the electrode and the module.

In an example, a wearable device or system for monitoring and/or recording signals from a person's brain can include a module with at least one electrode (e.g. EEG sensor), wherein the module is removably-attached to an eyewear temple, and wherein the electrode is pressed against the surface of the person's head by an adjustable electromagnetic actuator between the electrode and the module. In an example, a wearable device or system for monitoring and/or recording signals from a person's brain can include a module with at least one electrode (e.g. EEG sensor) which is removably-attached to an eyewear temple, wherein the module has an upper edge (or side) which is higher than (where it attaches to) the temple and a lower edge (or side) which is lower than (where it attaches to) the temple, and wherein the lower edge (or side) is at least 25% greater than the upper edge (or side).

In an example, a wearable device or system for monitoring and/or recording signals from a person's brain can include a module with at least one electrode (e.g. EEG sensor) which is removably-attached to an eyewear temple by two magnets, wherein the two magnets are at least ½ inch apart from each other. In an example, a wearable device or system for monitoring and/or recording signals from a person's brain can include a module with at least one electrode (e.g. EEG sensor) which is removably-attached to an eyewear temple by a first attachment mechanism (e.g. clip, clasp, clamp, snap, or hook) and a second attachment mechanism (e.g. clip, clasp, clamp, snap, or hook), wherein the first attachment mechanism is a first distance from the front piece, the second attachment mechanism is a second distance from the front piece, and the second distance is between ½ and 3 inches greater than the first distance. In an example, an electrode (or electrode module) can include a sleeve which slides onto (or over) an eyewear temple.

In an example, an electrode (or electrode module) can have one or more clips, clasps, or clamps which can be fastened onto different locations along the longitudinal axis of an eyewear temple, thereby enabling adjustment of the location of the electrode. In an example, an electrode (or electrode module) can have one or more rings into which (or through which) an eyewear temple is inserted, enabling the electrode (or electrode module) to be slid along the longitudinal axis of the temple and attached to each of several different locations on the temple. In an example, an electrode (or electrode module) can be attached to an eyewear temple by two or more springs of different diameters. In an example, an electrode (or electrode module) can be attached to an eyewear temple by one or more springs.

In an example, an eyewear temple can comprise of a series of modular components which can be connected to each other in different configurations, sequences, and/or orders, wherein one or more of the components include one or more electrodes for measuring brain wave activity. In an example, an eyewear temple can have a plurality of locations (e.g. slots, receptacles, ports, openings, or holes) onto which one or more electrodes (or electrode modules) can be selectively and reversibly fastened (e.g. snapped, clipped, clamped, hooked, inserted, or plugged), thereby enabling customization (e.g. varying and selective placement) of the locations of one or more electrodes along the temple. In an example, an eyewear temple can comprise of a longitudinal series of interdigitated modules, wherein one or more of the modules include one or more electrodes (e.g. EEG sensors) for measuring brain activity.

In an example, one or more electrode modules can be selectively and reversibly connected to different locations on a temple of an eyewear frame. In an example, one or more electrode modules can be selectively and reversibly connected to different locations on a temple of an eyewear frame, wherein connection provides power from a power source in the temple to a module. In an example, there can be a plurality of slots (e.g. slots, receptacles, ports, and/or openings) on an eyewear temple into which one or more electrodes (or electrode modules) can be inserted, wherein this insertion enables the transmission of electrical signals from the electrode to electronic components in the temple. In an example, a (modular) EEG monitoring system can include a strap (e.g. strap, band, loop, or arm) which spans a person's forehead, wherein the strap is removably-attached to the right-side and left-side temples of eyewear (e.g. eyeglasses), and wherein there is at least one electrode (e.g. EEG sensor) on the strap.

In an example, a (modular) EEG monitoring system can include a flexible (and elastic) strap (e.g. strap, band, loop, or arm) which spans a person's forehead, wherein the strap is removably-attached to the right-side and left-side temples of eyewear (e.g. eyeglasses), and wherein there is at least one electrode (e.g. EEG sensor) on the strap. In an example, a module with one or more electrodes can comprise an anterior connector (e.g. clip, clasp, clamp, hook, loop, strap, magnet, or hook-and-loop fabric) which attaches the module to an eyewear temple at a first location and a posterior connector (e.g. clip, clasp, clamp, hook, loop, strap, magnet, or hook-and-loop fabric) which attaches the module to the temple at a second location, wherein the anterior connector is at least one inch closer to the front piece of the eyewear than the posterior connector.

In an example, a wearable device or system for monitoring and/or recording signals from a person's brain can include a module with at least one electrode (e.g. EEG sensor) which is removably-attached to an eyewear temple by a first loop and a second loop, wherein the first loop is a first distance from the front piece, the second loop is a second distance from the front piece, and the second distance is at least ½ inch greater than the first distance. In an example, a wearable device or system for monitoring and/or recording signals from a person's brain can include a kidney-bean, crescent, or banana shaped module with an electrode (e.g. EEG sensor), wherein the module can be removably-attached to an eyewear (e.g. eyeglasses) frame, and wherein the longitudinal axis of the module is substantially parallel to the longitudinal axis of an eyewear temple when attached.

In an example, a wearable device or system for monitoring and/or recording signals from a person's brain can include an electrode (e.g. EEG sensor) module with a rounded square, rectangular, trapezoidal, or keystone shape which is removably-attached to the temple of an eyewear frame. In an example, a wearable device or system for monitoring and/or recording signals from a person's brain can include an electrode (e.g. EEG sensor) module with a cardioid, paint-palette, or lily-pad shape which is removably-attached to the temple of an eyewear frame.

In an example, an electrode module with one or more electrodes (e.g. EEG sensors) which is removably-attached to an eyewear temple can have a kidney-bean or crescent shape. In an example, an electrode module with one or more electrodes (e.g. EEG sensors) which is removably-attached to an eyewear temple can have a circular, elliptical, or oval shape. In an example, six electrodes (e.g. EEG sensors) can be integrated into eyewear (e.g. eyeglasses), wherein there are two electrodes on each temple (e.g. sidepiece) of the eyewear and two electrodes) on the nose pads of the eyewear. In an example, an eyewear temple can have a (longitudinal axis with a) shape comprising between one and two phases of a sinusoidal curve.

In an example, the anterior longitudinal axis of an eyewear temple can be arcuate. In an example, eyewear (e.g. eyeglasses) can comprise an arcuate (e.g. quarter-circle) arm which extends upward from the eyewear temple, wherein there are one or more electrodes (e.g. EEG sensors) on the arm. In an example, eyewear (e.g. eyeglasses) can comprise an arcuate (e.g. quarter-circle) arm which extends upward, inward, and forward (e.g. anteriorly) from the center of the eyewear temple, wherein one or more electrodes (e.g. EEG sensors) are on the arm. In an example, eyewear (e.g. eyeglasses) can comprise an arcuate (e.g. quarter-circle) arm which extends upward from the eyewear temple, wherein one or more electrodes (e.g. EEG sensors) are on the arm.

In an example, eyewear (e.g. eyeglasses) can comprise an arcuate (e.g. quarter-circle) arm which extends upward and forward (e.g. anteriorly) from the center of the eyewear temple, wherein one or more electrodes (e.g. EEG sensors) are on the arm. In an example, an eyewear frame can include a (flexible) arcuate arm (e.g. arm, band, strip, or loop) whose anterior end is attached to an eyewear rim and whose posterior end is attached to an eyewear temple, wherein there are one or more electrodes (e.g. EEG sensors) on this arm. In an example, an eyewear temple can bifurcate, wherein there is a circular, elliptical, or oval opening (e.g. opening, hole, or gap) between the upper branch (e.g. branch, arm, or loop) of the bifurcation and the lower branch of the bifurcation, and wherein there are one or more electrodes (e.g. EEG sensors) on one or both of the branches.

In an example, eyewear (e.g. eyeglasses) can comprise an arcuate loop or wave which extends upward, inward, and forward (e.g. anteriorly) from the eyewear temple, wherein one or more electrodes (e.g. EEG sensors) are on the loop or wave. In an example, eyewear (e.g. eyeglasses) can comprise an arcuate loop or wave which extends upward, inward, and forward (e.g. anteriorly) from the anterior third of the eyewear temple, wherein one or more electrodes (e.g. EEG sensors) are on the loop or wave. In an example, eyewear (e.g. eyeglasses) can comprise an arcuate loop or wave which extends upward and forward (e.g. anteriorly) from the eyewear temple, wherein one or more electrodes (e.g. EEG sensors) are on the loop or wave.

In an example, eyewear (e.g. eyeglasses) can comprise an arcuate loop or wave which extends upward and forward (e.g. anteriorly) from anterior third of the eyewear temple, wherein one or more electrodes (e.g. EEG sensors) are on the loop or wave. In an example, a neurological event (e.g. an epileptic seizure) can be predicted and/or detected by analysis a combination of data from one or more electrodes (e.g. EEG sensors) and one or more inertial motion units (e.g. accelerometers, gyroscopes, and/or inclinometers) which are on eyewear (e.g. eyeglasses). In an example, an electrode (e.g. EEG sensor) on eyewear (e.g. eyeglasses) worn by a person can function as part of a BCI (brain-to-computer) interface by monitoring and/or recording electromagnetic signals from the person's brain (e.g. brainwaves), wherein these electromagnetic signals are analyzed to interpret words, expressions, and/or commands from the person.

In an example, data from electrodes on eyewear worn by a person can be analyzed by artificial intelligence and/or machine learning to identify (e.g. interpret) words (e.g. commands) from the person's (electrical and/or electromagnetic) brain activity, wherein these words (e.g. commands) are used to control one or more devices (e.g. appliances, vehicles, security systems, environmental control systems, etc.). In an example, data from electrodes on eyewear can be analyzed by machine learning and/or artificial intelligence to identify (brain wave) patterns which are associated with particular words, phrases, commands, objects, neurological states, neurological events, and/or neurological conditions In an example, eyewear can comprise AR (augmented reality), MR (mixed reality), and/or VR (virtual reality) eyewear, wherein data from electrodes (e.g. EEG sensors) on the eyewear is analyzed to identify word and/or commands from the person. In an example, eyewear with one or more electrodes (e.g. EEG sensors) worn by a person can collect data concerning brain wave activity which is used to interpret words, commands, and/or communication from the person. In an example, eyewear with one or more electrodes (e.g. EEG sensors) worn by a person can collect data concerning brain wave activity which is used to predict and/or detect a stroke. In an example, a wearable device or system for predicting and/or detecting health events (e.g. a seizure, stroke, or heart attack) can comprise a module with at least one electrode (e.g. EEG sensor) which is removably-attached to a rim of eyewear (e.g. eyeglasses).

In an example, a wearable device or system for diagnosing, detecting, and/or predicting a health condition or event (e.g. seizure, stroke, or heart attack) can comprise an arcuate module with at least one electrode (e.g. EEG sensor) which monitors and/or records electrical signals from a person's brain, wherein the module is removably-attached to eyewear (e.g. eyeglasses) worn by the person, and wherein the module has a rounded trapezoidal shape. In an example, a wearable device or system for diagnosing, detecting, and/or predicting a health condition or event (e.g. seizure, stroke, or heart attack) can comprise an arcuate module with at least one electrode (e.g. EEG sensor) which monitors and/or records electrical signals from a person's brain, wherein the module is removably-attached to eyewear (e.g. eyeglasses) worn by the person, and wherein the module has an undulating (e.g. sinusoidal) shape. In an example, an earring can function as an electrode.

In an example, a device or system for monitoring and/or recording EEG signals can include at least one electrode (e.g. EEG sensor) which is part of eyewear (e.g. eyeglasses) behind a person's auricle (outer ear). In an example, an earring can function as an electrode and be in electrical communication with eyewear via a flexible wire. In an example, there can be at least two electrodes (e.g. EEG sensors) on each side (e.g. right and left) of eyewear (e.g. eyeglasses), wherein at least one electrode is located anterior to (e.g. in front of) the location where the eyewear rests on a person's auricle (outer ear) and at least one electrode is located posterior to (e.g. behind) that location. In an example, an electrode can be a dipole electrode. In an example, an electrode can be an electroconductive electrode.

In an example, an electrode can be made from a hydrogel which has been impregnated, doped, filled, and/or coated with silver, steel, copper, gold, aluminum, and/or carbon. In an example, an electrode can serve as an EEG sensor, a brainwave sensor, and/or a brain activity sensor. In an example, at least part of an electrode can be made with silicone. In an example, at least part of an electrode can be made from a hydrogel. In an example, data from electrodes can be locally amplified. In an example, electrodes can be in galvanic communication with a person's head.

In an example, the side of an electrode (e.g. EEG sensor) which faces toward the surface of a person's head can have parallel electroconductive ridges. In an example, eyewear (e.g. eyeglasses) may not really qualify as really being smart, but is at least above average. In an example, eyewear can comprise encephalographic eyeglasses. In an example, eyewear can include a wireless data transmitter. In an example, a brow bar with one or more electrodes (e.g. EEG sensors) can be attached to the front piece of conventional eyewear (e.g. eyeglasses) in order to convert the conventional eyewear into smart eyewear which monitors (electrical and/or electromagnetic) brain activity. In an example, an electrode (e.g. EEG sensor) on eyewear (e.g. eyeglasses) worn by a person can monitor and/or record the person's brainwaves.

In an example, an electrode (e.g. EEG sensor) can be part of (or removably-attached to) a front rim of eyewear (e.g. eyeglasses) worn by a person, wherein the electrode monitors and/or records electromagnetic signals from the person's brain (e.g. brainwaves). In an example, data from electrodes on eyewear worn by a person can be analyzed by artificial intelligence and/or machine learning to identify a health (e.g. neurological) condition. In an example, eyewear (e.g. eyeglasses) can include one or more electrodes (e.g. EEG sensors) which are located on a person's forehead above the eyewear rims. In an example, eyewear (e.g. eyeglasses) can include a data transmitter which transmits data from electrodes (e.g. EEG sensors) to a remote data processor (e.g. remote server).

In an example, eyewear (e.g. eyeglasses) can include a data processor, wherein data from electrodes (e.g. EEG sensors) on the eyewear is (at least partially) processed. In an example, eyewear (e.g. eyeglasses) with a plurality of electrodes (e.g. EEG sensors) can comprise augmented reality (AR) or virtual reality (VR) eyewear. In an example, eyewear (e.g. eyeglasses) worn by a person can incorporate one or more electrodes (e.g. EEG sensors) which monitor and/or record electromagnetic signals from the person's brain.

In an example, eyewear can comprise AR (augmented reality), MR (mixed reality), and/or VR (virtual reality) eyewear, wherein data from electrodes (e.g. EEG sensors) which serves as a BCI (Brain-to-Computer Interface).

In an example, eyewear can include an extension (or attachment) to the eyewear front piece which holds one or more electrodes on a person's forehead above the eyewear rims. In an example, eyewear can include one or more electrodes which are located on a person's forehead above their eyes. In an example, eyewear with electrodes (e.g. EEG sensors) can include speakers. In an example, eyewear with electrodes (e.g. EEG sensors) can include a heart rate sensor. In an example, eyewear with electrodes (e.g. EEG sensors) can function as a communication device for people who are unable to communicate vocally. In an example, eyewear with electrodes can be used as a BCI (brain-to-computer interface) for a person with neuromuscular paralysis.

In an example, eyewear with one or more electrodes can include an optical sensor. In an example, eyewear with one or more electrodes can include an electrode vibrator. In an example, eyewear with one or more electrodes can include a signal amplifier. In an example, eyewear with one or more electrodes can include a data communication unit (e.g., a WiFi transceiver, Bluetooth transceiver, or cellular transceiver). In an example, eyewear with one or more electrodes (e.g. EEG sensors) worn by a person can function as a brain-to-computer interface (BCI) which enables the person to control devices and/or send communications using their brain waves. In an example, eyewear with one or more electrodes (e.g. EEG sensors) worn by a person can collect data concerning brain wave activity which is used to control the operation of a medical device (e.g. a pacemaker or drug pump).

In an example, eyewear with one or more electrodes (e.g. EEG sensors) worn by a person can collect data concerning brain wave activity which is used to evaluate the person's fatigue level. In an example, eyewear with one or more electrodes (e.g. EEG sensors) worn by a person can collect data concerning brain wave activity which is analyzed to evaluate the person's mental state. In an example, one or more electrodes on eyewear (e.g. glasses) can serve as ground or reference electrodes. In an example, one or more electrodes on eyewear (e.g. eyeglasses) can emit electrical energy. In an example, the amount by which an electrode (e.g. EEG sensor) extends inward from an eyewear frame toward the surface of a person's head can be adjusted by moving a solenoid between the electrode and the eyewear frame.

In an example, the pressure exerted by an electrode (e.g. EEG sensor) on the surface of a person's head can be adjusted by inflating or deflating a chamber which is between the electrode and the eyewear frame. In an example, the pressure exerted by an electrode (e.g. EEG sensor) on the surface of a person's head can be adjusted by turning a spring which is between the electrode and the eyewear frame. In an example, eyewear (e.g. eyeglasses) worn by a person can include a substantially-transparent loop (e.g. loop, arch, wave, or arm) which is over (e.g. higher than) the rims of an eyewear front piece, wherein the loop spans from the right-side rim of the front piece to the left-side front piece, and wherein the loop holds at least two electrodes (e.g. EEG sensors) which are in electrical communication with the person's forehead.

In an example, eyewear (e.g. eyeglasses) worn by a person can include a loop (e.g. loop, arch, wave, or arm) which is over (e.g. higher than) the rims of an eyewear front piece, wherein the loop spans from the right-side rim of the front piece to the left-side front piece, and wherein the loop holds at least two electrodes (e.g. EEG sensors) in electrical communication with the person's forehead. In an example, eyewear (e.g. eyeglasses) worn by a person can include a bimodal loop (e.g. loop, arch, wave, or arm) which is over (e.g. higher than) the rims of an eyewear front piece, wherein the loop spans from the right-side rim of the front piece to the left-side front piece, and wherein the loop holds at least two electrodes (e.g. EEG sensors) in electrical communication with the person's forehead.

In an example, eyewear (e.g. eyeglasses) for monitoring and/or recording EEG signals can include a strap (e.g. strap, band, loop, or arm) which spans the middle of a person's forehead, from the right side of the forehead to the left side of the forehead, wherein there is an electrode (e.g. EEG sensor) on the strap above each eye and an electrode (e.g. EEG sensor) on the strap in the center of the forehead. In an example, eyewear (e.g. eyeglasses) worn by a person can include a substantially-transparent right-side arch (e.g. arch, wave, arm, or loop) over (e.g. higher than) the right-side rim of an eyewear front piece and a substantially-transparent left-side arch over the left-side rim of the front piece, wherein each arch holds at least one electrode (e.g. EEG sensor) in electrical communication with the person's forehead.

In an example, eyewear (e.g. eyeglasses) worn by a person can include a downwardly-concave loop (e.g. loop, arch, wave, or arm) over (e.g. higher than) the right-side rim of an eyewear front piece and a downwardly-concave loop over the left-side rim of the front piece, wherein each loop holds at least one electrode (e.g. EEG sensor) in electrical communication with the person's forehead. In an example, there can an arch (e.g. arch, loop, or arm) over each rim on an eyewear front piece, wherein there is at least one electrode (e.g. EEG sensor) on each arch, and wherein each electrode on an arch is in contact with a person's forehead. In an example, an electrode can comprise a nonconductive elastomeric polymer that is impregnated or doped with conductive material.

In an example, an electrode can comprise elastomeric material which has been impregnated, doped, filled, and/or coated with electroconductive material. In an example, at least part of an electrode can be made with an elastomeric polymer which has been impregnated, doped, filled, and/or coated with electroconductive material (e.g. silver, silver-chloride, steel, aluminum, or carbon). In an example, at least part of an electrode can be made from PDMS which has been impregnated, doped, filled, and/or coated with a metal powder (e.g. silver, copper, gold, steel, or aluminum), graphite, or carbon nanotubes. In an example, at least part of an electrode can be made from a silicone-based polymer which has been impregnated, doped, filled, and/or coated with silver, steel, copper, gold, aluminum, and/or carbon.

In an example, an electrode (e.g. EEG sensor) on eyewear can be made from material with a Shore 00 value between 30 and 80. In an example, an electrode (e.g. EEG sensor) on eyewear (e.g. glasses) can be made with PDMS (polydimethylsiloxane) which has been impregnated, doped, filled, and/or coated with electroconductive material. In an example, an electrode (e.g. EEG sensor) on eyewear (e.g. glasses) can be made with an electroconductive polymer. In an example, an electrode (e.g. EEG sensor) on eyewear (e.g. glasses) can be made with a silicone-based elastomeric polymer which has been impregnated, doped, filled, and/or coated with carbon material (e.g. carbon nanotubes). In an example, a device or system for monitoring and/or recording EEG signals can include a module with at least one electrode (e.g. EEG sensor), whereon the module is removably-attached to eyewear (e.g. eyeglasses) behind a person's auricle (outer ear) by a (tension-adjustable) spring mechanism.

In an example, data from electrodes can be processed (including amplification) locally within an electrode module. In an example, an electrode (or electrode module) can be attached to an eyewear frame by parts on the electrode (or electrode module) and frame which stick together. In an example, an electrode (or electrode module) can be attached to an eyewear frame by interdigitating parts on the electrode (or electrode module) and frame, wherein the interdigitating parts connect to each other. In an example, data from electrodes can be processed (including amplification) locally within an electrode module which is removably-attached to an eyewear frame. In an example, one or more electrode modules can be selectively and reversibly connected to an eyewear frame. In an example, one or more electrode (e.g. EEG sensor) modules can be selectively and reversibly connected to different locations an eyewear frame, wherein each module contains a power source and data processing unit as well as an electrode.

In an example, there can be a telescoping mechanism (e.g. telescoping rod, piston, or shock absorber) between an electrode (or electrode module) and an eyewear frame. In an example, there can be a metal or polymer spring between an electrode (or electrode module) and an eyewear frame. In an example, a modular wearable device or system for monitoring and/or recording signals from a person's brain can include a circular, elliptical, or oval module with an electrode (e.g. EEG sensor), wherein the module is removably-attached to an eyewear (e.g. eyeglasses) frame. In an example, a wearable device or system for monitoring and/or recording signals from a person's brain can include an electrode (e.g. EEG sensor) module with a kidney-bean, crescent, or banana shape which is removably-attached to an eyewear frame.

In an example, an electrode (e.g. EEG sensor) on eyewear (e.g. eyeglasses) worn by a person can part be of a system to diagnose and/or treat a neurological condition by monitoring and/or recording electromagnetic signals from the person's brain (e.g. brainwaves). In an example, a device or system for monitoring and/or recording EEG signals can include at least one electrode (e.g. EEG sensor) which is part of the nose bridge and/or nose pads of eyewear. In an example, smart eyewear can include an electrode on each of two nose pads. In an example, a device or system for monitoring and/or recording EEG signals can include a module with at least one electrode (e.g. EEG sensor), whereon the module is removably-attached to the nose bridge and/or nose pads of eyewear by a (tension-adjustable) spring mechanism.

In an example, electrodes on eyewear which are anterior to an auricle can be substantially flat and electrodes on the eyewear which are posterior to the auricle can have a concentric array of electroconductive protrusions (e.g. protrusions, prongs, teeth, legs, pins, and/or bumps). In an example, there can be at least two electrodes (e.g. EEG sensors) on each side (e.g. right and left) of eyewear (e.g. eyeglasses), wherein at least one anterior electrode is located anterior to (e.g. in front of) the location where the eyewear rests on a person's auricle (outer ear) and at least one posterior electrode is located posterior to (e.g. behind) that location, wherein the side of the anterior electrode which faces toward a person's head is substantially flat, and wherein the side of the posterior electrode which faces toward the person's head has a plurality of electroconductive protrusions (e.g. protrusions, prongs, teeth, legs, pins, and/or bumps) which contact the surface of the person's head.

In an example, a protrusion (e.g. protrusion, prong, tooth, leg, pin, and/or bump) which extends out from an electrode base toward the surface of a person's head can comprise a central electroconductive core and an outer non-conductive layer, wherein the core and the outer layer are concentric. In an example, a protrusion (e.g. protrusion, prong, tooth, leg, pin, and/or bump) which extends out from an electrode base toward the surface of a person's head can comprise a central nonconductive core and an outer electroconductive layer, wherein the outer layer becomes thicker closer to the electrode base. In an example, an electrode (e.g. EEG sensor) can comprise a base with a Shore 00 value between 30 and 80 and a plurality of protrusions (e.g. protrusions, prongs, teeth, legs, pins, and/or bumps) with Shore 00 values between 15 and 50.

In an example, an electrode (e.g. EEG sensor) can comprise a base and a plurality of electroconductive protrusions (e.g. protrusions, prongs, teeth, legs, pins, and/or bumps) which extend out from the base toward the surface of a person's head, wherein the protrusions are configured in rows and columns on the base. In an example, an electrode (e.g. EEG sensor) can comprise a base and a plurality of electroconductive protrusions (e.g. protrusions, prongs, teeth, legs, pins, and/or bumps) which extend out from the base toward the surface of a person's head, wherein the electroconductivity of the protrusions increases with distance from the base. In an example, an electrode (e.g. EEG sensor) can comprise a base and a plurality of electroconductive protrusions (e.g. protrusions, prongs, teeth, legs, pins, and/or bumps) which extend out from the base toward the surface of a person's head, wherein the durometer levels of the protrusions increase with distance from the base.

In an example, an electrode (e.g. EEG sensor) can comprise a base and a plurality of electroconductive protrusions (e.g. protrusions, prongs, teeth, legs, pins, and/or bumps) which extend out from the base toward the surface of a person's head, wherein the angles at which the protrusions extend out from the base increase with their distance from the center of the base. In an example, an electrode (e.g. EEG sensor) can comprise a base and a plurality of electroconductive protrusions (e.g. protrusions, prongs, teeth, legs, pins, and/or bumps) which extend out from the base toward the surface of a person's head, wherein the durometer levels of the protrusions decrease with distance from the base.

In an example, an electrode can comprise one or more electromagnetic actuators which move one or more protrusions (e.g. protrusions, prongs, teeth, legs, pins, and/or bumps) in a direction which is substantially perpendicular to the surface of a person's head and/or to the surface of the base of the electrode, thereby adjusting the pressure with which the protrusions contact the surface of the person's head. In an example, an electrode can comprise one or more electromagnetic actuators which vibrate and/or oscillate one or more protrusions (e.g. protrusions, prongs, teeth, legs, pins, and/or bumps) in directions which are substantially perpendicular to the surface of a person's head and/or to the surface of the base of the electrode, thereby adjusting the pressure with which the protrusions contact the surface of the person's head.

In an example, an electrode can comprise one or more electromagnetic actuators which move one or more protrusions (e.g. protrusions, prongs, teeth, legs, pins, and/or bumps). In an example, an electrode can comprise one or more electromagnetic actuators which move one or more protrusions (e.g. protrusions, prongs, teeth, legs, pins, and/or bumps) closer to, or farther from, the surface of a person's head. In an example, an electrode can comprise a plurality of electromagnetic actuators, each of which individually moves one protrusion (e.g. protrusion, prong, tooth, leg, pin, and/or bump) which extends out from the electrode. In an example, an electrode can include a plurality of spring-loaded protrusions (e.g. protrusions, prongs, teeth, legs, pins, and/or bumps) which extend out from an electrode base at different angles. In an example, an electrode can include a plurality of spring-loaded protrusions (e.g. protrusions, prongs, teeth, legs, pins, and/or bumps) which extend out from an electrode base at angles which decrease with the distance of a protrusion from the center of the electrode base.

In an example, an electrode can include a plurality of protrusions (e.g. protrusions, prongs, teeth, legs, pins, and/or bumps) which extend out from the electrode base and which vibrate and/or oscillate along vectors which intersect the electrode base at acute angles. In an example, an electrode can include a plurality of non-parallel spring-loaded protrusions (e.g. protrusions, prongs, teeth, legs, pins, and/or bumps). In an example, an electrode with a plurality of protrusions (e.g. protrusions, prongs, teeth, legs, pins, and/or bumps) can be rotated to enable the protrusions to slide between strands of hair.

In an example, the diameter of a protrusion (e.g. protrusion, prong, tooth, pin, or bump) which extends out from an electrode base can decrease with distance from the electrode base. In an example, eyewear (e.g. eyeglasses) worn by a person can include an electromagnetic actuator which moves an electrode (e.g. EEG sensor) with a plurality of electroconductive protrusions (e.g. protrusions, prongs, teeth, legs, pins, and/or bumps) to help the protrusions to penetrate between strands of hair on the person's head. In an example, eyewear (e.g. eyeglasses) worn by a person can include an electromagnetic actuator which rotates and/or revolves an electrode (e.g. EEG sensor) to help protrusions (e.g. protrusions, prongs, teeth, legs, pins, and/or bumps) on the sensor to penetrate between strands of hair and achieve better electroconductive contact with the person's head.

In an example, eyewear (e.g. eyeglasses) worn by a person can include an electromagnetic mechanism which moves (e.g. moves, oscillates, and/or vibrates) an electrode (e.g. EEG sensor) in a reciprocating manner to help protrusions (e.g. protrusions, prongs, teeth, legs, pins, and/or bumps) on the sensor to penetrate between strands of hair and achieve better electroconductive contact with the person's head. In an example, an electrode (e.g. EEG sensor) on eyewear can have protrusions (e.g. protrusions, prongs, teeth, legs, pins, and/or bumps) which are made with material with a Shore 00 value between 15 and 50.

In an example, an electrode (e.g. EEG sensor) on eyewear (e.g. glasses) can have protrusions (e.g. protrusions, prongs, teeth, legs, pins, and/or bumps) which are made from an elastomeric polymer which has been impregnated, doped, filled, and/or coated with electroconductive material, wherein the protrusions can penetrate between strands of hair to improve electromagnetic communication between the electrode and the person's head. In an example, an electrode (or electrode module) can comprise two parallel disk-shaped components, a first disk-shaped component with electroconductive protrusions (e.g. protrusions, prongs, teeth, legs, pins, and/or bumps) which is closer to the surface of a person's head and a second disk-shaped component which is farther from the surface of the person's head, wherein the first component rotates relative to the second component.

In an example, eyewear (e.g. eyeglasses) can have one or more electrodes (e.g. EEG sensors) with protrusions (e.g. protrusions, prongs, teeth, legs, pins, and/or bumps) on the temples, wherein the temples have hinges and/or joints which move when the eyewear is put onto a person's head, and wherein this movement causes the protrusions to slide relative to the surface of the person's head, thereby causing the protrusions to slide between strands of hair for better electroconductive contact with the person's head. In an example, eyewear (e.g. eyeglasses) can comprise an arm or protrusion which extends upward and inward from the eyewear temple, wherein one or more electrodes (e.g. EEG sensors) are on the arm or protrusion. In an example, the anterior longitudinal axis of an eyewear temple can have an upward wave (e.g. wave, curve, bump, loop, and/or protrusion) on which an electrode (e.g. EEG sensor) is located.

In an example, there can be a concave wave (e.g. wave, curve, bump, loop, and/or protrusion) in the anterior longitudinal axis of an eyewear temple and at least one electrode (e.g. EEG sensor) on the wave, wherein the wave has a length between ½ and 3 inches. In an example, there can be a concave wave (e.g. wave, curve, bump, loop, and/or protrusion) in the anterior longitudinal axis of an eyewear temple and at least one electrode (e.g. EEG sensor) on the wave, wherein the wave has a height between ½ and 3 inches and a length between ½ and 3 inches. In an example, there can be an upward wave (e.g. wave, curve, bump, loop, and/or protrusion) in the posterior third of the anterior longitudinal axis of an eyewear temple, wherein an electrode (e.g. EEG sensor) is located on the upward wave.

In an example, eyewear (e.g. eyeglasses) can comprise an undulating (e.g. sinusoidal) arm or protrusion which extends upward from the eyewear temple, wherein one or more electrodes (e.g. EEG sensors) are on the arm or protrusion. In an example, the anterior longitudinal axis of an eyewear temple can have an upward wave (e.g. wave, curve, bump, loop, and/or protrusion) on which an electrode (e.g. EEG sensor) is located, wherein the wave has a semi-circular shape. In an example, a wearable device or system for monitoring and/or recording signals from a person's brain can include an electrode (e.g. EEG sensor) with a kidney-bean, crescent, or banana shape. In an example, the side of an electrode (e.g. EEG sensor) which faces toward the surface of a person's head can have circular electroconductive ridges. In an example, the shape of an eyewear frame can be adjusted (e.g. custom fit to the contour of an individual's head) by heating and cooling the frame.

In an example, eyewear can include an arcuate (e.g. downwardly-concave) extension (or attachment) to the eyewear front piece which holds one or more electrodes on a person's forehead above their eyes. In an example, eyewear can include an arcuate (e.g. downwardly-concave) extension (or attachment) to the eyewear front piece which holds one or more electrodes above a person's eye. In an example, eyewear (e.g. eyeglasses) worn by a person can include an undulating (e.g. sinusoidal) loop (e.g. loop, arch, wave, or arm) which is over (e.g. higher than) the rims of an eyewear front piece, wherein the loop spans from the right-side rim of the front piece to the left-side front piece, and wherein the loop holds at least two electrodes (e.g. EEG sensors) in electrical communication with the person's forehead. In an example, there are can be at least one censer in the interior portion of the temple, one censer in the middle portion of the temple, and one censer in the outer courts.

In an example, a wearable device or system for diagnosing, detecting, and/or predicting a health condition or event (e.g. seizure, stroke, or heart attack) can comprise: a right-side module which is attached (e.g. clipped, clamped, snapped, hooked, or adhered) to the right-side temple of eyewear (e.g. eyeglasses), wherein the right-side module includes at least one electrode (e.g. EEG sensor); and a left-side module which is attached to the left-side temple of eyewear, wherein the left-side module includes at least one electrode. In an example, a wearable device or system for diagnosing, detecting, and/or predicting a health condition or event (e.g. seizure, stroke, or heart attack) can include a module which is removably-attached by a snap, clip, clamp, clasp, or hook to an eyewear temple worn by a person, wherein the module includes at least one electrode (e.g. EEG sensor).

In an example, a wearable device or system for diagnosing, detecting, and/or predicting a health condition or event (e.g. seizure, stroke, or heart attack) can include a module with a longitudinal channel (e.g. opening) into which (and/or through which) an eyewear temple is inserted, wherein the module includes at least one electrode (e.g. EEG sensor). In an example, a wearable device or system for predicting and detecting neurological seizures can include a module with at least one electrode (e.g. EEG sensor) which is removably-attached to an eyewear temple at two places along the longitudinal axis of the temple. In an example, a wearable device or system for diagnosing, detecting, and/or predicting a health condition or event (e.g. seizure, stroke, or heart attack) can include a module which is removably-attached by hook-and-loop material to an eyewear temple worn by a person, wherein the module includes at least one electrode (e.g. EEG sensor).

In an example, a wearable device or system for predicting and detecting neurological seizures can comprise an arcuate module with at least one electrode (e.g. EEG sensor) which monitors and/or records electrical signals from a person's brain, wherein the module is removably-attached to the temple of eyewear (e.g. eyeglasses), wherein the arcuate module has an circular, elliptical, or oval shape, wherein the longitudinal axis of the module is substantially perpendicular to the longitudinal axis of the temple, and wherein at least half of the module extends above the location where the module is attached to the temple. In an example, a wearable device or system for predicting and detecting neurological seizures can comprise an arcuate module with at least one electrode (e.g. EEG sensor) which monitors and/or records electrical signals from a person's brain, wherein the module is removably-attached to eyewear (e.g. eyeglasses) worn by the person, and wherein at least 25% of the module is extends above the location where it is attached to the temple.

In an example, the central longitudinal axis of the section of a temple (e.g. sidepiece) of an eyewear (e.g. eyeglasses) frame which extends from a person's auricle (outer ear) to the front piece of the eyewear can be substantially straight. In an example, the central longitudinal axis of the section of a temple (e.g. sidepiece) of an eyewear (e.g. eyeglasses) frame which extends from a person's auricle (outer ear) to the front piece of the eyewear can include both an upwardly-convex wave (or curve) and a downwardly-convex wave (or curve). In an example, the section of a temple (e.g. sidepiece) of an eyewear (e.g. eyeglasses) frame which extends from a person's auricle (outer ear) to the front piece of the eyewear can include an upwardly-convex wave or curve.

In an example, the section of a temple (e.g. sidepiece) of an eyewear (e.g. eyeglasses) frame which extends from a person's auricle (outer ear) to the front piece of the eyewear can have a bifurcated sub-section. In an example, a temple (also called a sidepiece, bow, arm, or leg) of eyewear (e.g. eyeglasses) rests on a person's auricle (e.g. outer ear) at a first location which is at a first height (when the person is standing upright), a first electrode (e.g. EEG sensor) is on the temple at a second location which is at a second height, and a second electrode is on the temple at a third location which is at a third height, wherein the second height is above the first height, and wherein the third height is below the first height.

In an example, a temple (also called a sidepiece, bow, arm, or leg) of eyewear (e.g. eyeglasses) rests on a person's auricle (e.g. outer ear) at a first location which is at a first height (when the person is standing upright), a first electrode (e.g. EEG sensor) is on the temple at a second location which is at a second height, and a second electrode is on the temple at a third location which is at a third height, wherein the second height is between ½ and 3 inches above the first height, wherein the third height is between ½ and 3 inches below the first height, wherein the second location is anterior to the first location, and wherein the third location is posterior to the first location.

In an example, a temple (also called a sidepiece, bow, arm, or leg) of eyewear (e.g. eyeglasses) rests on a person's auricle (e.g. outer ear) at a first location which is at a first height (when the person is standing upright), a first electrode (e.g. EEG sensor) is on the temple at a second location which is at a second height, and a second electrode is on the temple at a third location which is at a third height, wherein the second height is above the first height, wherein the third height is above the first height, wherein the second location is anterior to the first location, and wherein the third location is posterior to the first location. In an example, there can be at least two electrodes (e.g. EEG sensors) on the right-side eyewear temple, wherein at least one of the electrodes is anterior to the person's auricle (outer ear) and at least one of the electrodes is posterior to (e.g. behind or curved around the back of) the person's auricle.

In an example, there can be at least two electrodes (e.g. EEG sensors) on an eyewear temple, wherein at least one of the electrodes is anterior to (e.g. in front of) the person's auricle (outer ear) and at least one of the electrodes is posterior to (e.g. behind or curved around the rear of) the person's auricle. In an example, there can be at least two electrodes (e.g. EEG sensors) on an eyewear temple, wherein at least one electrode is higher than the location where the temple rests on the person's auricle (outer ear) and at least one electrode is lower than this location. In an example, there can be at least two electrodes (e.g. EEG sensors) on an eyewear temple, wherein at least one electrode is at least ½ inch higher than the top of the person's auricle (outer ear) and at least one electrode is at least ½ inch below the top of the person's auricle.

In an example, there can be at least two electrodes (e.g. EEG sensors) on a left-side eyewear temple worn by a person, wherein at least one of the electrodes is anterior to (e.g. in front of) the person's left auricle (outer ear) and at least one of the electrodes is posterior to (e.g. behind or curved around the rear of) the person's left auricle. In an example, the anterior longitudinal axis of an eyewear temple can be substantially straight. In an example, the curvature of the posterior portion of an eyewear temple can be adjusted (e.g. custom fit to the contour of an individual's head) by inflation of an inflatable chamber. In an example, a device or system for monitoring and/or recording EEG signals can include at least one electrode (e.g. EEG sensor) which is part of the posterior portion of an eyewear temple.

In an example, a smart temple with one or more electrodes can replace a conventional temple on conventional eyewear (e.g. eyeglasses), thereby turning the conventional eyewear into smart eyewear which can monitor (electrical and/or electromagnetic) brain activity. In an example, an electrode (e.g. EEG sensor) can be slid back and forth along the longitudinal axis of an eyewear temple and also locked (e.g. snapped, clipped, or clamped) in a selected location on the temple, thereby enabling adjustment of the location where the electrode contacts the surface of a person's head. In an example, an electrode (e.g. EEG sensor) can be part of (or removably-attached to) the posterior half of an eyewear temple worn by a person, wherein the electrode monitors and/or records electromagnetic signals from the person's brain (e.g. brainwaves). In an example, an electrode (e.g. EEG sensor) can be attached to an eyewear temple by two or more springs.

In an example, an electrode (e.g. EEG sensor) can be attached to an eyewear temple by two or more springs with different lengths. In an example, an electrode (e.g. EEG sensor) can be attached to an eyewear temple by two or more springs whose tensions can be adjusted. In an example, an electrode (e.g. EEG sensor) can be attached to an eyewear temple by two or more nested (e.g. concentric) springs. In an example, an electrode (or movable component holding an electrode) can have a first configuration in which it is recessed into an eyewear temple and a second configuration in which it extends out from the temple toward the surface of a person's head, wherein the electrode (or component) is moved from its first configuration to its second configuration by being pivoted, rotated, unfolded, or bent.

In an example, an eyewear frame can include a pivoting and/or rotating arm with one or more electrodes on it, wherein the arm has a first configuration in which it is parallel with the longitudinal axis of an eyewear temple and a second configuration in which it is perpendicular to the longitudinal axis at an acute angle. In an example, an eyewear frame can include a pivoting and/or rotating arm with one or more electrodes on it, wherein the arm has a first configuration in which it is recessed into an eyewear temple and a second configuration in which it extends out from the temple. In an example, an eyewear temple can have a (central) wave (e.g. wave, arch, and/or curve) which curves upward from the rest of the temple and forward toward a person's forehead, wherein there are one or more electrodes (e.g. EEG sensors) on the central wave.

In an example, an eyewear temple can comprise of a plurality of linkable components, wherein the components can be linked (e.g. linked, connected, attached, snapped, fit) together in different configurations, sequences, or orders, and wherein one or more of the components includes one or more electrodes (e.g. EEG sensors) for measuring brain activity. In an example, an eyewear temple can include a track (e.g. track, channel, slot, or groove) along which a plurality of electrodes (e.g. EEG sensors) can be slid back and forth, or locked at a selected locations on the temple. In an example, eyewear (e.g. eyeglasses) can comprise at least six electrodes (e.g. EEG sensors): at least one sensor on the anterior portion of the right temple, at least one sensor on the posterior portion of the right temple, at least one sensor on the anterior portion of the left temple, at least one sensor on the posterior portion of the left temple, at least one sensor the right side of the front piece, and at least one sensor on the left side of the front piece.

In an example, eyewear (e.g. eyeglasses) can comprise: a front piece; and right and left side temples; wherein a temple is connected to the front piece by a hinge, wherein there is at least one electrode (e.g. EEG sensor) on the temple, and wherein the distance between the electrode on the surface of the person's head is adjusted by adjusting the tension of a spring (or other tensile mechanism) attached to the hinge and/or temple. In an example, one or more electrodes (or arms with one or more electrodes) can have a first configuration in which they are recessed onto or within an eyewear temple and a second configuration in which they extend out from the temple in order to contact the surface of a person's head.

In an example, one or more electrodes (or arms with one or more electrodes) can have a first configuration in which they are recessed onto or within an eyewear temple and a second configuration in which they extend out from the temple in order to contact the surface of a person's head, wherein the electrodes are changed from their first configuration to their second configuration (or vice versa) by one or more inflatable chambers. In an example, six electrodes (e.g. EEG sensors) can be integrated into eyewear (e.g. eyeglasses), wherein there are two electrodes on each temple (e.g. sidepiece) of the eyewear and two electrodes on the rims of the eyewear. In an example, the central third of the anterior portion of the temple of eyewear can be at least 25% wider than the anterior and posterior thirds of the anterior portion in order to allow placement of one or more electrodes at locations which are higher than the anterior and posterior thirds of the anterior portion.

In an example, the posterior end of an eyewear temple can bifurcate, wherein there is at least one electrode (e.g. EEG sensor) on each branch of the bifurcation. In an example, the tension of a hinge which connects a front piece of eyewear to an eyewear temple can be automatically adjusted in order to adjust the contact pressure of between one or more electrodes on the temple and a person's head. In an example, there can be at least two electrodes (e.g. EEG sensors) on each temple (e.g. the right-side and left-side sidepieces) of eyewear (e.g. eyeglasses). In an example, there can be compressible foam (or gel) between an electrode (e.g. EEG sensor) and the temple of an eyewear frame.

In an example, a strap (e.g. strap, band, loop, or arm) which spans a person's forehead can be attached to the right-side and left-side temples of eyewear (e.g. eyeglasses), wherein there is at least one electrode (e.g. EEG sensor) on the strap. In an example, a strap (e.g. strap, band, loop, or arm) which spans a person's forehead can be attached by (tension-adjustable) spring mechanisms to the right-side and left-side temples of eyewear (e.g. eyeglasses), wherein there is at least one electrode (e.g. EEG sensor) on the strap. In an example, an eyewear temple can have a (central) wave (e.g. wave, arch, loop, or bend) which curves inward from the rest of the temple toward the surface of a person's head, wherein there are one or more electrodes (e.g. EEG sensors) on the central wave and/or arch.

In an example, an upper band (e.g. band, strap, or arm) which loops over the top (e.g. the upper third) of a person's head can be attached to the anterior-longitudinal-third of a right-side eyewear temple and to the anterior-longitudinal-third of a left-side eyewear temple, wherein there is at least one electrode (e.g. EEG sensor) on the band. In an example, eyewear (e.g. eyeglasses) for monitoring and/or recording EEG signals can include a strap (e.g. strap, band, loop, or arm) which spans the middle of a person's forehead, from the right side of the forehead to the left side of the forehead, wherein there are at least two electrodes (e.g. EEG sensors) on the strap, and wherein the strap is connected to (the central one-third longitudinal sections of) the right-side and left-side temples of the eyewear.

In an example, eyewear (e.g. eyeglasses) can comprise a loop or wave which extends upward and inward from the eyewear temple, wherein one or more electrodes (e.g. EEG sensors) are on the loop or wave. In an example, eyewear can comprise a flexible band (e.g. band, arm, strap, or strip), wherein the band includes one or more electrodes, wherein the band has a first configuration in which it is retracted (e.g. coiled) onto or within an eyewear temple and a second configuration in which it is extended (e.g. uncoiled) from the temple and loops around the rear of the person's head. In an example, eyewear can comprise a substantially-transparent band (e.g. band, arm, strap, or strip) which spans a person's forehead from one temple of the eyewear to the other, wherein there are two or more electrodes (e.g. EEG sensors) on the band.

In an example, eyewear can comprise a band (e.g. band, arm, strap, or strip) made from shape memory material, wherein the band extends out from an eyewear temple, and wherein the band holds one or more electrodes (e.g. EEG sensors) against the surface of a person's head. In an example, a device or system for monitoring and/or recording EEG signals can include a module with at least one electrode (e.g. EEG sensor), whereon the module is removably-attached to the posterior portion of an eyewear temple by a (tension-adjustable) spring mechanism. In an example, a system or device for monitoring and/or recording brain activity can comprise two or more modules, wherein each module has at least one electrode (e.g. EEG sensor), and wherein each module is plugged (e.g. plugged, inserted, or snapped) into one of a plurality of different slots (e.g. slots, receptacles, or openings) along the temple (e.g. sidepiece) of eyewear.

In an example, a wearable device or system for monitoring and/or recording signals from a person's brain can include a module with at least one electrode (e.g. EEG sensor), wherein the module is removably-attached to an eyewear temple, and wherein the module spans between 20% and 40% of the anterior portion of the temple. In an example, a wearable device or system for monitoring and/or recording signals from a person's brain can include a module with at least one electrode (e.g. EEG sensor), wherein the module is removably-attached to an eyewear temple, and wherein the module (e.g. the electrode on the module) is pressed against the surface of the person's head by an anterior (tension-adjustable) spring between the module and a posterior (tension-adjustable) spring between the module and the temple.

In an example, there can be a flexible protrusion (e.g. flexible spring or strip) between an electrode and an eyewear temple, wherein the protrusion pushes the electrode out from the temple into contact with a person's head, wherein the anterior and posterior ends of the protrusion are attached to the temple, wherein the middle of the protrusion extends (e.g. bulges) out from the temple, wherein the amount by which the middle of the protrusion extends out from the temple (and the amount of pressure exerted by the electrode on the person's head) can be adjusted by moving (e.g. sliding) the anterior and posterior ends of the protrusion closer together or father apart, wherein there is a knob (e.g. knob, pin, button, or clip) on the anterior end or the posterior end of the protrusion, and wherein the anterior and posterior ends of the protrusion are moved closer together or farther apart by moving (e.g. sliding) the knob.

In an example, eyewear can comprise a wave (e.g. wave, loop, branch, or arm) which extends (e.g. extends, spans, or curves) between ½ and 3 inches inward from its connection with the (middle third of the) anterior portion of an eyewear temple, wherein there is at least one electrode on the wave. In an example, eyewear can comprise a wave (e.g. wave, loop, branch, or arm) which extends (e.g. extends, spans, or curves) between ½ and 3 inches upward from its connection with the (middle third of the) anterior portion of an eyewear temple, wherein there is at least one electrode on the wave. In an example, eyewear can comprise a temple whose anterior portion is generally straight (and horizontal) except for a wave (e.g. wave, loop, branch, or arm) which extends (e.g. extends, spans, or curves) upward from where it deviates from the otherwise straight anterior portion of an eyewear temple, wherein there is at least one electrode on the wave.

In an example, there can be a flexible protrusion (e.g. flexible spring or strip) between an electrode and an eyewear temple, wherein the protrusion pushes the electrode out from the temple into contact with a person's head, wherein the anterior and posterior ends of the protrusion are attached to the temple, wherein the middle of the protrusion extends (e.g. bulges) out from the temple, wherein the amount by which the middle of the protrusion extends out from the temple (and the amount of pressure exerted by the electrode on the person's head) can be adjusted by moving (e.g. sliding) the anterior and posterior ends of the protrusion closer together or father apart, wherein there is a knob (e.g. knob, pin, button, or clip) on the anterior end or the posterior end of the protrusion, wherein the anterior and posterior ends of the protrusion are moved closer together or farther apart by moving (e.g. sliding) the knob, and wherein rotating the knob in a first direction enables an end to be moved, but rotating the knob in the opposite direction locks the end in place.

In an example, eyewear can comprise a protrusion (e.g. protrusion, arm, band, strap, or loop) which is connected to the posterior third of the anterior portion of the eyewear temple, wherein there is at least one electrode on the protrusion. In an example, eyewear can comprise an anterior electrode on the anterior portion of a temple and a posterior electrode on the posterior portion of a temple, wherein the side (e.g. side or surface) of the posterior electrode which faces toward a person's head has several electroconductive protrusions (e.g. protrusions, prongs, teeth, pins, ridges, or bumps) which slide between strands of hair and the side of the anterior electrode which faces toward the person's head does not have these protrusions.

In an example, eyewear can comprise a temple whose anterior portion is generally straight (and horizontal) except for a wave (e.g. wave, loop, branch, or arm) which extends (e.g. extends, spans, or curves) between ½ and 3 inches upward from where it deviates from the otherwise straight anterior portion of an eyewear temple, wherein there is at least one electrode on the wave. In an example, eyewear can comprise a temple whose anterior portion is generally straight (and horizontal) except for a wave (e.g. wave, loop, branch, or arm) which extends (e.g. extends, spans, or curves) inward from the rest of the anterior portion (e.g. extending out from the middle third of the anterior portion) of an eyewear temple, wherein there is at least one electrode on the wave.

In an example, eyewear can comprise a temple whose anterior portion is generally straight (and horizontal) except for a wave (e.g. wave, loop, branch, or arm) which extends (e.g. extends, spans, or curves) between ½ and 3 inches inward from the rest of the anterior portion (e.g. extending out from the middle third of the anterior portion) of an eyewear temple, wherein there is at least one electrode on the wave. In an example, eyewear can comprise a temple whose anterior portion is generally straight (and horizontal) except for a wave (e.g. wave, loop, branch, or arm) which extends (e.g. extends, spans, or curves) between ½ and 3 inches upward and between ½ and 3 inches inward from the rest of the anterior portion (e.g. extending out from the middle third of the anterior portion) of an eyewear temple, wherein there is at least one electrode on the wave.

In an example, there can be a flexible protrusion (e.g. flexible spring or strip) between an electrode and an eyewear temple, wherein the protrusion pushes the electrode out from the temple into contact with a person's head, wherein the anterior and posterior ends of the protrusion are attached to the temple, and wherein the middle of the protrusion extends (e.g. bulges) out from the temple. In an example, eyewear can comprise a temple whose anterior portion is generally straight (and horizontal) except for a wave (e.g. wave, loop, branch, or arm) which extends (e.g. extends, spans, or curves) inward from where it deviates from the otherwise straight anterior portion of an eyewear temple, wherein there is at least one electrode on the wave.

In an example, eyewear can comprise a temple whose anterior portion is generally straight (and horizontal) except for a wave (e.g. wave, loop, branch, or arm) which extends (e.g. extends, spans, or curves) between ½ and 3 inches inward from where it deviates from the otherwise straight anterior portion of an eyewear temple, wherein there is at least one electrode on the wave. In an example, eyewear can comprise a wave (e.g. wave, loop, branch, or arm) which extends (e.g. extends, spans, or curves) upward and inward from its connection with the (middle third of the) anterior portion of an eyewear temple, wherein there is at least one electrode on the wave. In an example, eyewear can comprise an anterior electrode (anterior to an auricle) and a posterior electrode (posterior to the auricle), wherein the side (e.g. side or surface) of the posterior electrode which faces toward a person's head has several electroconductive protrusions (e.g. protrusions, prongs, teeth, pins, ridges, or bumps) which slide between strands of hair and the side of the anterior electrode which faces toward the person's head does not have these protrusions. In an example, eyewear can comprise an anterior electrode (anterior to an auricle) and a posterior electrode (posterior to the auricle), wherein the side (e.g. side or surface) of the posterior electrode which faces toward a person's head has several electroconductive protrusions (e.g. protrusions, prongs, teeth, pins, ridges, or bumps) and the side of the anterior electrode which faces toward the person's head does not have these protrusions. In an example, eyewear can comprise a temple whose anterior portion is generally straight (and horizontal) except for a wave (e.g. wave, loop, branch, or arm) which extends (e.g. extends, spans, or curves) upward and inward from where it deviates from the otherwise straight anterior portion of an eyewear temple, wherein there is at least one electrode on the wave.

In an example, there can be a flexible protrusion (e.g. flexible spring or strip) between an electrode and an eyewear temple, wherein the protrusion pushes the electrode out from the temple into contact with a person's head, wherein the anterior and posterior ends of the protrusion are attached to the temple, wherein the middle of the protrusion extends (e.g. bulges) out from the temple, and wherein the amount by which the middle of the protrusion extends out from the temple (and the amount of pressure exerted by the electrode on the person's head) can be adjusted. In an example, eyewear can comprise a temple whose anterior portion is generally straight (and horizontal) except for a wave (e.g. wave, loop, branch, or arm) which extends (e.g. extends, spans, or curves) between ½ and 3 inches upward and between ½ and 3 inches inward from where it deviates from the otherwise straight anterior portion of an eyewear temple, wherein there is at least one electrode on the wave.

In an example, there can be a flexible protrusion (e.g. flexible spring or strip) between an electrode and an eyewear temple, wherein the protrusion pushes the electrode out from the temple into contact with a person's head, wherein the anterior and posterior ends of the protrusion are attached to the temple, wherein the middle of the protrusion extends (e.g. bulges) out from the temple, and wherein the amount by which the middle of the protrusion extends out from the temple (and the amount of pressure exerted by the electrode on the person's head) can be adjusted by moving (e.g. sliding) the anterior and posterior ends of the protrusion closer together or father apart. In an example, eyewear can comprise a protrusion (e.g. protrusion, arm, band, strap, or loop) which is connected to the anterior third of the anterior portion of the eyewear temple, wherein there is at least one electrode on the protrusion.

In an example, eyewear can comprise an anterior electrode on the anterior portion of a temple and a posterior electrode on the posterior portion of a temple, wherein the side (e.g. side or surface) of the posterior electrode which faces toward a person's head has several electroconductive protrusions (e.g. protrusions, prongs, teeth, pins, ridges, or bumps) and the side of the anterior electrode which faces toward the person's head does not have these protrusions. In an example, eyewear can comprise a protrusion (e.g. protrusion, arm, band, strap, or loop) which extends (e.g. extends, spans, or curves) out (e.g. upward or inward) from the anterior third of the anterior portion of the eyewear temple, wherein there is at least one electrode on the protrusion.

In an example, eyewear can comprise an anterior electrode on the anterior portion of a temple and a posterior electrode on the posterior portion of a temple, wherein the side (e.g. side or surface) of the posterior electrode which faces toward a person's head has several electroconductive protrusions (e.g. protrusions, prongs, teeth, pins, ridges, or bumps) which extend out between ⅛ and ½ of an inch from the base of the electrode and the side of the anterior electrode which faces toward the person's head does not have these protrusions. In an example, eyewear can comprise a temple whose anterior portion is generally straight (and horizontal) except for a wave (e.g. wave, loop, branch, or arm) which extends (e.g. extends, spans, or curves) between ½ and 3 inches upward from the rest of the anterior portion (e.g. extending out from the middle third of the anterior portion) of an eyewear temple, wherein there is at least one electrode on the wave.

In an example, there can be a flexible protrusion (e.g. flexible spring or strip) between an electrode and an eyewear temple, wherein the protrusion pushes the electrode out from the temple into contact with a person's head, wherein the anterior and posterior ends of the protrusion are attached to the temple, wherein the middle of the protrusion extends (e.g. bulges) out from the temple, wherein the amount by which the middle of the protrusion extends out from the temple (and the amount of pressure exerted by the electrode on the person's head) can be adjusted by moving (e.g. sliding) the anterior and posterior ends of the protrusion closer together or father apart, wherein there is a knob (e.g. knob, pin, button, or clip) on the anterior end or the posterior end of the protrusion, wherein the anterior and posterior ends of the protrusion are moved closer together or farther apart by moving (e.g. sliding) the knob, and wherein pulling on the knob enables an end to be moved, but pushing the knob locks the end in place.

In an example, eyewear can comprise a protrusion (e.g. protrusion, arm, band, strap, or loop) which extends (e.g. extends, spans, or curves) out (e.g. upward or inward) from the middle third of the anterior portion of the eyewear temple, wherein there is at least one electrode on the protrusion. In an example, eyewear can comprise an anterior electrode on the anterior portion of a temple and a posterior electrode on the posterior portion of a temple, wherein the side (e.g. side or surface) of the posterior electrode which faces toward a person's head has several electroconductive protrusions (e.g. protrusions, prongs, teeth, pins, ridges, or bumps) which extend out between ¼ and ¾ or an inch from the base of the electrode and the side of the anterior electrode which faces toward the person's head does not have these protrusions.

In an example, eyewear can comprise a temple whose anterior portion is generally straight (and horizontal) except for a wave (e.g. wave, loop, branch, or arm) which extends (e.g. extends, spans, or curves) upward and inward from the rest of the anterior portion (e.g. extending out from the middle third of the anterior portion) of an eyewear temple, wherein there is at least one electrode on the wave. In an example, there can be a flexible protrusion (e.g. flexible spring or strip) between an electrode and an eyewear temple, wherein the protrusion extends (e.g. bulges) out from the temple and pushes the electrode into contact with a person's head, and wherein the protrusion has a semicircular, arch, sinusoidal-phase, and/or wave shape.

In an example, eyewear can comprise a wave (e.g. wave, loop, branch, or arm) which extends (e.g. extends, spans, or curves) inward from its connection with the (middle third of the) anterior portion of an eyewear temple, wherein there is at least one electrode on the wave. In an example, eyewear can comprise a protrusion (e.g. protrusion, arm, band, strap, or loop) which is connected to the middle third of the anterior portion of the eyewear temple, wherein there is at least one electrode on the protrusion. In an example, eyewear can comprise an anterior electrode on the anterior portion of a temple and a posterior electrode on the posterior portion of a temple, wherein the side (e.g. side or surface) of the anterior electrode which faces toward a person's head has a first amount of surface curvature variation, wherein the side (e.g. side or surface) of the posterior electrode which faces toward a person's head has a second amount of surface curvature variation, and wherein the second amount is greater than the first amount.

In an example, eyewear can comprise a wave (e.g. wave, loop, branch, or arm) which extends (e.g. extends, spans, or curves) upward from its connection with the (middle third of the) anterior portion of an eyewear temple, wherein there is at least one electrode on the wave. In an example, eyewear can comprise a protrusion (e.g. protrusion, arm, band, strap, or loop) which extends (e.g. extends, spans, or curves) out (e.g. upward or inward) from the posterior third of the anterior portion of the eyewear temple, wherein there is at least one electrode on the protrusion. In an example, there can be a flexible protrusion (e.g. flexible spring or strip) between an electrode and an eyewear temple, wherein the protrusion extends (e.g. bulges) out from the temple and pushes the electrode into contact with a person's head, and wherein the protrusion has a concave shape.

In an example, eyewear can comprise a wave (e.g. wave, loop, branch, or arm) which extends (e.g. extends, spans, or curves) between ½ and 3 inches upward and between ½ and 3 inches inward from its connection with the (middle third of the) anterior portion of an eyewear temple, wherein there is at least one electrode on the wave. In an example, eyewear can comprise a temple whose anterior portion is generally straight (and horizontal) except for a wave (e.g. wave, loop, branch, or arm) which extends (e.g. extends, spans, or curves) upward from the rest of the anterior portion (e.g. extending out from the middle third of the anterior portion) of an eyewear temple, wherein there is at least one electrode on the wave.

In an example, a wearable device or system for monitoring and/or recording signals from a person's brain can include a module with at least one electrode (e.g. EEG sensor), wherein the module is removably-attached to an eyewear temple, and wherein the module (e.g. the electrode on the module) is pressed against the surface of the person's head by an adjustable electromagnetic actuator between the module and the temple. In an example, a wearable device or system for monitoring and/or recording signals from a person's brain can include a module with at least one electrode (e.g. EEG sensor), wherein the module is removably-attached to an eyewear temple, and wherein the electrode is pressed against the surface of the person's head by compressible foam between the electrode and the module.

In an example, a wearable device or system for monitoring and/or recording electrical signals from a person's brain can comprise: a right-side module with at least one electrode (e.g. EEG sensor) which is removably-attached to the right-side temple of eyewear (e.g. eyeglasses); and a left-side module with at least one electrode which is removably-attached to the left-side temple of the eyewear. In an example, a wearable device or system for monitoring and/or recording signals from a person's brain can include a module with at least one electrode (e.g. EEG sensor) which is removably-attached to an eyewear temple, wherein the module has an anterior edge (or side) and a posterior edge (or side), and wherein the anterior edge (or side) is at least 25% greater (e.g. wider) than the posterior edge (or side).

In an example, a wearable device or system for monitoring and/or recording signals from a person's brain can include a module with at least one electrode (e.g. EEG sensor) which is removably-attached to an eyewear temple by two clips, clasps, clamps, hooks, pins, or snaps, wherein the two clips, clasps, clamps, hooks, pins, or snaps are at least ½ inch apart from each other. In an example, a wearable device or system for monitoring and/or recording signals from a person's brain can include a module with at least one electrode (e.g. EEG sensor) which is removably-attached to an eyewear temple at two places along a longitudinal axis of the temple, wherein the two places are at least ½ inch apart from each other.

In an example, an electrode (or electrode module) can be inserted into a slot (e.g. receptacle, slot, port, opening, or hole) on an eyewear temple. In an example, an electrode (or electrode module) can include a hook, clasp, or clamp which is fastened onto an eyewear temple to hold the electrode (or electrode module) on the temple. In an example, an electrode (or electrode module) can include a ring into which (or through which) an eyewear temple is inserted to hold the electrode (or electrode module) on the temple. In an example, an electrode (or electrode module) can be attached to an eyewear temple by two or more nested (e.g. concentric) springs.

In an example, an electrode (e.g. EEG sensor) or electrode module can be moved backward or forward (e.g. slid in a posterior direction or in anterior direction) along a track (e.g. track, channel, slot, or groove) on an eyewear temple and then locked (e.g. snapped, clipped, or clamped) into place at a selected location on the temple, thereby enabling adjustment of the location where the electrode contacts the surface of a person's head. In an example, an eyewear temple can comprise a channel (e.g. channel, track, slot, or groove) along which one or more electrodes (or electrode modules) can be slid in an anterior direction or in a posterior direction. In an example, an eyewear temple can comprise of a series of modular components which can be connected (e.g. connected, attached, inserted, snapped, or clipped) together in different configurations, sequences, or orders, wherein one or more of the components include one or more electrodes (e.g. EEG sensors) for measuring brain activity.

In an example, an eyewear temple can comprise of a longitudinal series of interconnected and/or linked modules, wherein one or more of the modules includes one or more electrodes (e.g. EEG sensors) for measuring brain activity. In an example, one or more electrode modules can be selectively and reversibly connected to a temple of an eyewear frame. In an example, one or more electrode modules can be selectively and reversibly connected to different locations on a temple of an eyewear frame, wherein connection provides an electronic connection between the temple and the module.

In an example, a (modular) EEG monitoring system can include a strap (e.g. strap, band, loop, or arm) which loops around the back of a person's head, wherein the strap is removably-attached to the posterior ends of the right-side and left-side temples of eyewear (e.g. eyeglasses), and wherein there is at least one electrode (e.g. EEG sensor) on the strap. In an example, a (modular) EEG monitoring system can include a flexible (e.g. flexible and elastic) strap (e.g. strap, band, loop, or arm) which loops around the back of a person's head, wherein the strap is removably-attached to the posterior ends of the right-side and left-side temples of eyewear (e.g. eyeglasses), and wherein there is at least one electrode (e.g. EEG sensor) on the strap.

In an example, a module with one or more electrodes can comprise an anterior connector (e.g. clip, clasp, clamp, hook, loop, strap, magnet, or hook-and-loop fabric) which attaches the module to an eyewear temple at a first location and a posterior connector (e.g. clip, clasp, clamp, hook, loop, strap, magnet, or hook-and-loop fabric) which attaches the module to the temple at a second location, wherein the anterior connector is closer to the front piece of the eyewear than the posterior connector. In an example, a wearable device or system for monitoring and/or recording signals from a person's brain can include a module with at least one electrode (e.g. EEG sensor) which is removably-attached to an eyewear temple by two loops, wherein the two loops are at least ½ inch apart from each other.

In an example, a wearable device or system for monitoring and/or recording signals from a person's brain can include a module with at least one electrode (e.g. EEG sensor) which is removably-attached to an eyewear temple by a first loop and a second loop, wherein the first loop is a first distance from the front piece, the second loop is a second distance from the front piece, and the second distance is between ½ and 3 inches greater than the first distance. In an example, a wearable device or system for monitoring and/or recording signals from a person's brain can include a circular, elliptical, or oval module with an electrode (e.g. EEG sensor), wherein the module can be removably-attached to an eyewear (e.g. eyeglasses) frame, and wherein the longitudinal axis of the module is substantially parallel to the longitudinal axis of an eyewear temple when attached.

In an example, a wearable device or system for monitoring and/or recording signals from a person's brain can include an electrode (e.g. EEG sensor) module with a kidney-bean, crescent, or banana shape which is removably-attached to the temple of an eyewear frame. In an example, an electrode module with one or more electrodes (e.g. EEG sensors) which is removably-attached to an eyewear temple can have an hourglass shape. In an example, an electrode module with one or more electrodes (e.g. EEG sensors) which is removably-attached to an eyewear temple can have a hyperbolic shape. In an example, an electrode module with one or more electrodes (e.g. EEG sensors) which is removably-attached to an eyewear temple can have a cardioid shape. In an example, an eyewear temple can have a (longitudinal axis with a) sinusoidal shape.

In an example, an eyewear temple can have a (longitudinal axis with a) shape comprising at least two complete phases of a sinusoidal curve. In an example, a custom-shaped foam piece between the temple of eyewear and an electrode can be created by 3D printing based on the size and shape of an individual's head. In an example, eyewear (e.g. eyeglasses) can comprise a crescent, kidney, or banana shaped arm which extends upward from the eyewear temple, wherein there are one or more electrodes (e.g. EEG sensors) on the arm. In an example, eyewear (e.g. eyeglasses) can comprise an arcuate (e.g. quarter-circle) arm which extends upward, inward, and forward (e.g. anteriorly) from the (longitudinally) central one-third of the eyewear temple, wherein one or more electrodes (e.g. EEG sensors) are on the arm.

In an example, eyewear (e.g. eyeglasses) can comprise an arcuate (e.g. quarter-circle) arm which extends upward and inward from the eyewear temple, wherein one or more electrodes (e.g. EEG sensors) are on the arm. In an example, eyewear (e.g. eyeglasses) can comprise an arcuate (e.g. quarter-circle) arm which extends upward and forward (e.g. anteriorly) from (longitudinally) central one-third of the eyewear temple, wherein one or more electrodes (e.g. EEG sensors) are on the arm.

In an example, an eyewear temple can bifurcate, wherein there is an opening (e.g. opening, hole, or gap) between the upper branch (e.g. branch, arm, or loop) of the bifurcation and the lower branch of the bifurcation, wherein the opening has an upper perimeter which is a phase of a sinusoidal curve, wherein the opening has a lower perimeter which is the opposite phase of a sinusoidal curve, and wherein there are one or more electrodes (e.g. EEG sensors) on one or both of the branches. In an example, eyewear (e.g. eyeglasses) can comprise an undulating (e.g. sinusoidal) loop or wave which extends upward from the eyewear temple, wherein one or more electrodes (e.g. EEG sensors) are on the loop or wave. In an example, eyewear (e.g. eyeglasses) can comprise an arcuate loop or wave which extends upward, inward, and forward (e.g. anteriorly) from the center of the eyewear temple, wherein one or more electrodes (e.g. EEG sensors) are on the loop or wave.

In an example, eyewear (e.g. eyeglasses) can comprise an arcuate loop or wave which extends upward from the eyewear temple, wherein one or more electrodes (e.g. EEG sensors) are on the loop or wave. In an example, eyewear (e.g. eyeglasses) can comprise an arcuate loop or wave which extends upward and forward (e.g. anteriorly) from the center of the eyewear temple, wherein one or more electrodes (e.g. EEG sensors) are on the loop or wave. In an example, an electrode (e.g. EEG sensor) on eyewear (e.g. eyeglasses) worn by a person can part be of a system to predict and/or detect neurological seizures by monitoring and/or recording electromagnetic signals from the person's brain (e.g. brainwaves). In an example, data from electrodes on eyewear worn by a person can be analyzed by machine learning and/or artificial intelligence to identify (e.g. interpret) messages (e.g. words) from the person's (electrical and/or electromagnetic) brain activity.

In an example, data from electrodes on eyewear worn by a person can be analyzed by artificial intelligence and/or machine learning to predict and/or detect a neurological event (e.g. epileptic seizure). In an example, eyewear (e.g. eyeglasses) which is worn by a person can comprise a plurality of electrodes (e.g. EEG sensors) which monitor and/or record the person's brainwaves to predict and/or detect neurological (e.g. epileptic) seizures. In an example, eyewear with electrodes which is worn by a first person who is unable to communicate vocally can serve as a communication device, wherein data from the electrodes concerning the first person's brain activity is analyzed to interpret words and/or messages which are then communicated to a second person. In an example, eyewear with one or more electrodes (e.g. EEG sensors) worn by a person can collect data concerning brain wave activity which is used to predict and/or detect an epileptic seizure.

In an example, a wearable device or system for predicting and detecting neurological seizures can comprise a module with at least one electrode (e.g. EEG sensor) which is removably-attached to eyewear (e.g. eyeglasses). In an example, a wearable device or system for diagnosing, detecting, and/or predicting a health condition or event (e.g. seizure, stroke, or heart attack) can comprise an arcuate module with at least one electrode (e.g. EEG sensor) which monitors and/or records electrical signals from a person's brain, wherein the module is removably-attached to eyewear (e.g. eyeglasses) worn by the person.

In an example, a wearable device or system for diagnosing, detecting, and/or predicting a health condition or event (e.g. seizure, stroke, or heart attack) can comprise an arcuate module with at least one electrode (e.g. EEG sensor) which monitors and/or records electrical signals from a person's brain, wherein the module is removably-attached to eyewear (e.g. eyeglasses) worn by the person, and wherein the module has an oval or elliptical shape. In an example, a reference or ground electrode can curve around the back of a person's auricle. In an example, an electrode (e.g. EEG sensor) can curve around the back of a person's auricle (outer ear). In an example, a reference or ground electrode which is attached to a person's earlobe can be connected to electronics in an eyewear frame via a flexible wire.

In an example, eyewear can hold a reference electrode against the surface of a person's head behind the person's auricle (outer ear). In an example, an electrode can be a bipole electrode. In an example, an electrode can be a monopole electrode. In an example, an electrode can be based on capacitance. In an example, an electrode can record and/or monitor electromagnetic brain activity. In an example, analog data from electrodes can be converted to digital data by (local intra-device) analog-to-digital convertors. In an example, at least part of an electrode can be made from PDMS which has been impregnated, doped, filled, and/or coated with silver, steel, copper, gold, aluminum, and/or carbon. In an example, data from electrodes can be filtered to remove noise.

In an example, electrodes can be in capacitive communication with a person's head. In an example, the pressure between an electrode and the surface of a person's head can be adjusted. In an example, both EEG data and EMG data can be collected and brain activity (EEG) signals can be better isolated by filtering out muscle activity (EMG) signals. In an example, eyewear can comprise AR/VR (augmented reality and/or virtual reality) eyewear. In an example, eyewear can include a power source (e.g. battery). In an example, one or more EEG (electroencephalographic) sensors can be incorporated into eyewear (e.g. eyeglasses). In an example, a first set of electrodes on eyewear can emit electrical energy and a second set of electrodes on the eyewear can receive electrical energy.

In an example, an electrode (e.g. EEG sensor) on eyewear (e.g. eyeglasses) worn by a person can monitor and/or record electromagnetic signals from the person's brain (e.g. brainwaves). In an example, data from electrodes can be processed (including amplification) locally within an eyewear frame. In an example, electrodes which are incorporated into eyewear can be dry electrodes. In an example, eyewear (e.g. eyeglasses) can include one or more electrodes (e.g. EEG sensors) which are located above a person's eyes. In an example, eyewear (e.g. eyeglasses) can include a data transmitter which transmits data from electrodes (e.g. EEG sensors) to a data processor in a separate wearable device (e.g. a smart watch).

In an example, eyewear (e.g. eyeglasses) can include a brow bar, wherein there are one or more electrodes (e.g. EEG sensors) on the brow bar. In an example, eyewear (e.g. eyeglasses) with a plurality of electrodes (e.g. EEG sensors) can comprise a BCI (Brain-to-Computer Interface). In an example, eyewear (e.g. eyeglasses) worn by a person can incorporate one or more electrodes (e.g. EEG sensors) which monitor and/or record electrical signals from the person's brain. In an example, eyewear can hold an electrode at a mastoid point on a person's head.

In an example, eyewear can include an extension (or attachment) to the eyewear front piece which holds one or more electrodes on a person's forehead above the eyewear rims. In an example, eyewear can include two extensions (or attachments) to the eyewear front piece which hold electrodes on a person's forehead above their eyes. In an example, eyewear with electrodes (e.g. EEG sensors) can include speakers which emit binaural beats based on a person's brain waves. In an example, eyewear with electrodes (e.g. EEG sensors) can include a display. In an example, eyewear with electrodes (e.g. EEG sensors) can function as a biofeedback system. In an example, eyewear with electrodes can be used as a BCI (brain-to-computer interface) for shopping.

In an example, eyewear with one or more electrodes can include an augmented reality (AR) display. In an example, eyewear with one or more electrodes can include a spectroscopic sensor. In an example, eyewear with one or more electrodes can include a display screen. In an example, eyewear with one or more electrodes can include a camera. In an example, eyewear with one or more electrodes (e.g. EEG sensors) worn by a person can collect data concerning brain wave activity which is used to evaluate the cognitive function of the person. In an example, eyewear with one or more electrodes (e.g. EEG sensors) worn by a person can collect data concerning brain wave activity which is used to evaluate the person's stress level.

In an example, eyewear with one or more electrodes (e.g. EEG sensors) worn by a person can collect data concerning brain wave activity which is analyzed to enable the person to control devices and/or send communications using their brain waves. In an example, eyewear with one or more electrodes (e.g. EEG sensors) worn by a person can collect data concerning brain wave activity which is used to enable the person to play a game via their brain waves. In an example, one or more electrodes on eyewear (e.g. eyeglasses) can provide neurostimulation. In an example, the amount by which an electrode (e.g. EEG sensor) extends inward from an eyewear frame toward the surface of a person's head can be adjusted by activating and/or moving a magnet between the electrode and the eyewear frame.

In an example, the amount by which an electrode (e.g. EEG sensor) extends inward from an eyewear frame toward the surface of a person's head can be adjusted by rotating a threaded member between the electrode and the eyewear frame. In an example, the pressure exerted by an electrode (e.g. EEG sensor) on the surface of a person's head can be adjusted by moving a solenoid which is between the electrode and the eyewear frame. In an example, there can be at least two electrodes (e.g. EEG sensors) on each side (e.g. right side and left side) of eyewear (e.g. eyeglasses). In an example, eyewear (e.g. eyeglasses) for monitoring and/or recording EEG signals can include a strap (e.g. strap, band, loop, or arm) which spans the middle of a person's forehead, from the right side of the forehead to the left side of the forehead, wherein there are at least two electrodes (e.g. EEG sensors) on the strap.

In an example, eyewear (e.g. eyeglasses) worn by a person can include a loop (e.g. loop, arch, wave, or arm) which is between ½ and 3 inches over (e.g. higher than) the rims of an eyewear front piece, wherein the loop spans from the right-side rim of the front piece to the left-side front piece, and wherein the loop holds at least two electrodes (e.g. EEG sensors) in electrical communication with the person's forehead. In an example, eyewear (e.g. eyeglasses) worn by a person can include a forehead loop (e.g. loop, arch, wave, or arm), wherein one end of the loop connects to the top portion of the right-side rim of an eyewear front piece and the other end of the loop connects to the top portion of the left-side rim of the front piece, and wherein the loop has at least two electrodes (e.g. EEG sensor) which are in electrical communication with the person's forehead.

In an example, eyewear (e.g. eyeglasses) can include a posterior loop which goes around the back of a person's head, wherein there is at least one electrode (e.g. EEG sensor) on the loop. In an example, eyewear (e.g. eyeglasses) worn by a person can include a right-side arch (e.g. arch, wave, arm, or loop) which connects to the top portion of the right-side rim of an eyewear front piece and a left-side arch which connects to the top portion of the left-side rim of the front piece, wherein each arch holds at least one electrode (e.g. EEG sensor) in electrical communication with the person's forehead. In an example, there can an arch (e.g. arch, loop, or arm) over each rim on an eyewear front piece, wherein each arch or loop extends up onto a person's forehead, and wherein there is at least one electrode (e.g. EEG sensor) on each arch.

In an example, an electrode can comprise an elastomeric polymer which has been impregnated, doped, filled, and/or coated with carbon or metal matter. In an example, an electrode can comprise a nonconductive elastomeric polymer that is dipped into conductive material. In an example, an electrode can comprise foam which has been impregnated, doped, filled, and/or coated with electroconductive material. In an example, at least part of an electrode can be made with a compressible, malleable, and/or low-durometer non-conductive material (e.g. a non-conductive elastomeric polymer) which has been coated with a conductive material (e.g. carbon or metal particles).

In an example, at least part of an electrode can be made from an elastomeric polymer which has been impregnated, doped, filled, and/or coated with silver, steel, copper, gold, aluminum, and/or carbon. In an example, at least part of an electrode can be made from a silicone-based polymer which has been impregnated, doped, filled, and/or coated with a metal powder (e.g. silver, copper, gold, steel, or aluminum), graphite, or carbon nanotubes. In an example, an electrode (e.g. EEG sensor) on eyewear can be made from material with a Shore 00 value between 15 and 50.

In an example, an electrode (e.g. EEG sensor) on eyewear (e.g. glasses) can be made with PDMS (polydimethylsiloxane) which has been impregnated, doped, filled, and/or coated with carbon material (e.g. carbon nanotubes). In an example, an electrode (e.g. EEG sensor) on eyewear (e.g. glasses) can be made with an elastomeric polymer which has been impregnated, doped, filled, and/or coated with electroconductive material. In an example, electrodes which are incorporated into eyewear can be dry electrodes which are made from a soft polymer, wherein the soft polymer has been made electroconductive by being impregnated, doped, filled, and/or coated with electroconductive material. In an example, an electrode (or electrode module) can comprise two parallel components, a first component which is closer to the surface of a person's head and a second component which is farther from the surface of the person's head, wherein the first component rotates relative to the second component, or vice versa.

In an example, data from electrodes can be partly processed (including amplification) locally within an electrode module and then further processed after transmission to a remote device. In an example, an electrode (or electrode module) can be attached to an eyewear frame by parts on the electrode (or electrode module) and frame which clip together. In an example, an electrode module can be attached to conventional eyewear in order to turn the conventional eyewear into smart eyewear which can collect data concerning a person's brain activity. In an example, data from electrodes can be partly processed (including amplification) locally within an electrode module which is removably-attached to an eyewear frame and then further processed after transmission to a remote device.

In an example, one or more electrode modules can be selectively and reversibly connected to different locations an eyewear frame, wherein connection provides power from a power source in the eyewear frame to a module. In an example, there can be a helical spring between an electrode (or electrode module) and an eyewear frame. In an example, there can be an inflatable chamber between an electrode (or electrode module) and an eyewear frame. In an example, a modular wearable device or system for monitoring and/or recording signals from a person's brain can include a kidney-bean, crescent, or banana shaped module with an electrode (e.g. EEG sensor), wherein the module is removably-attached to an eyewear (e.g. eyeglasses) frame.

In an example, a wearable device or system for monitoring and/or recording signals from a person's brain can include a cardioid, paint-palette, or lily-pad shaped module with an electrode (e.g. EEG sensor), wherein the module can be removably-attached to an eyewear (e.g. eyeglasses) frame. In an example, a wearable device or system for monitoring and/or recording signals from a person's brain can include an electrode (e.g. EEG sensor) module with a circular, elliptical, or oval shape which is removably-attached to an eyewear frame. In an example, eyewear with one or more electrodes (e.g. EEG sensors) worn by a person can collect data concerning brain wave activity which is used to diagnose a health condition (e.g. a neurological or cardiovascular condition).

In an example, an electrode (e.g. EEG sensor) can be part of (or removably-attached to) the nose bridge of eyewear (e.g. eyeglasses) worn by a person, wherein the electrode monitors and/or records electromagnetic signals from the person's brain (e.g. brainwaves). In an example, there can be one or more electrodes on the nose bridge (and/or nose pads) of eyewear. In an example, electrodes on eyewear which are anterior to an auricle can be substantially flat and electrodes on the eyewear which are posterior to the auricle can have electroconductive protrusions (e.g. protrusions, prongs, teeth, legs, pins, and/or bumps).

In an example, electrodes on eyewear which are anterior to an auricle can be substantially flat and electrodes on the eyewear which are posterior to the auricle can have an orthogonal array of electroconductive protrusions (e.g. protrusions, prongs, teeth, legs, pins, and/or bumps). In an example, a protrusion (e.g. protrusion, prong, tooth, leg, pin, and/or bump) which extends out from an electrode base toward the surface of a person's head can have a central electroconductive core and an outer non-conductive layer. In an example, a protrusion (e.g. protrusion, prong, tooth, leg, pin, and/or bump) which extends out from an electrode base toward the surface of a person's head can comprise a central nonconductive core and an outer electroconductive layer, wherein the core and the outer layer are concentric.

In an example, a protrusion (e.g. protrusion, prong, tooth, leg, pin, and/or bump) which extends out from an electrode base toward the surface of a person's head can comprise a central electroconductive core and an outer non-conductive layer, wherein the outer layer becomes thicker father from the electrode base. In an example, an electrode (e.g. EEG sensor) can comprise a base with a Shore 00 value between 15 and 50 and a plurality of protrusions (e.g. protrusions, prongs, teeth, legs, pins, and/or bumps) with Shore 00 values between 30 and 80. In an example, an electrode (e.g. EEG sensor) can comprise a base and a plurality of electroconductive protrusions (e.g. protrusions, prongs, teeth, legs, pins, and/or bumps) which extend out from the base toward the surface of a person's head, wherein the protrusions are configured in rings on the base.

In an example, an electrode (e.g. EEG sensor) can comprise a base and a plurality of electroconductive protrusions (e.g. protrusions, prongs, teeth, legs, pins, and/or bumps) which extend out from the base toward the surface of a person's head, wherein the diameters and/or cross-sectional perimeters of the protrusions increase with distance from the base. In an example, an electrode (e.g. EEG sensor) can comprise a base and a plurality of electroconductive protrusions (e.g. protrusions, prongs, teeth, legs, pins, and/or bumps) which extend out from the base toward the surface of a person's head, wherein the angles at which the protrusions extend out from the base vary proportionally with distance from the center of the base.

In an example, an electrode (e.g. EEG sensor) can comprise a base and a plurality of electroconductive protrusions (e.g. protrusions, prongs, teeth, legs, pins, and/or bumps) which extend out from the base toward the surface of a person's head, wherein the angles at which the protrusions extend out from the base decrease with their distance from the center of the base. In an example, an electrode (e.g. EEG sensor) can comprise a base and a plurality of protrusions (e.g. protrusions, prongs, teeth, legs, pins, and/or bumps) which extend out from the base, wherein the protrusions are harder (e.g. less flexible and/or compliant) than the base.

In an example, an electrode can comprise one or more electromagnetic actuators which move one or more protrusions (e.g. protrusions, prongs, teeth, legs, pins, and/or bumps) in a direction which is substantially parallel to the surface of a person's head and/or to the surface of the base of the electrode, thereby enabling the protrusions to slide between strands of hair on the person's head. In an example, an electrode can comprise one or more electromagnetic actuators which vibrate and/or oscillate one or more protrusions (e.g. protrusions, prongs, teeth, legs, pins, and/or bumps) in directions which are substantially parallel to the surface of a person's head and/or to the surface of the base of the electrode, thereby enabling the protrusions to slide between strands of hair on the person's head.

In an example, an electrode can comprise one or more electromagnetic actuators which move one or more protrusions (e.g. protrusions, prongs, teeth, legs, pins, and/or bumps) in a direction which is substantially perpendicular to the surface of a person's head and/or to the surface of the base of the electrode. In an example, an electrode can comprise one or more electromagnetic actuators which moves one or more protrusions (e.g. protrusions, prongs, teeth, legs, pins, and/or bumps) which extend out from the electrode. In an example, an electrode can have a base and plurality of protrusions (e.g. protrusions, prongs, teeth, legs, pins, and/or bumps) which extend out from the base, wherein a portion of a protrusion which is farther from the base is softer (more flexible and/or compliant) than a portion of the protrusion which is closer to the base.

In an example, an electrode can include a plurality of spring-loaded protrusions (e.g. protrusions, prongs, teeth, legs, pins, and/or bumps) which extend out from an electrode base at angles which are correlated with the distance of a protrusion from the center of the electrode base. In an example, an electrode can include a plurality of spring-loaded protrusions (e.g. protrusions, prongs, teeth, legs, pins, and/or bumps). In an example, an electrode can include a plurality of protrusions (e.g. protrusions, prongs, teeth, legs, pins, and/or bumps) which extend out from the electrode base and which vibrate and/or oscillate along vectors which are substantially parallel to the electrode base. In an example, an electrode can include a plurality of individually spring-loaded protrusions (e.g. protrusions, prongs, teeth, legs, pins, and/or bumps).

In an example, an electrode with a plurality of protrusions (e.g. protrusions, prongs, teeth, legs, pins, and/or bumps) can be automatically rotationally-oscillated (e.g. rotated back and forth in clockwise and counter-clockwise directions) to enable the protrusions to slide between strands of hair. In an example, an electrode (e.g. EEG sensor) on eyewear can have protrusions (e.g. protrusions, prongs, teeth, legs, pins, and/or bumps) with a Shore 00 value between 30 and 80. In an example, eyewear (e.g. eyeglasses) worn by a person can include a vibrating mechanism which vibrates an electrode (e.g. EEG sensor) with a plurality of electroconductive protrusions (e.g. protrusions, prongs, teeth, legs, pins, and/or bumps) to cause the protrusions to slide between strands of hair and achieve better electroconductive contact between the protrusions and the surface of the person's head.

In an example, eyewear (e.g. eyeglasses) worn by a person can include an electromagnetic actuator which vibrates and/or oscillates an electrode (e.g. EEG sensor) to help protrusions (e.g. protrusions, prongs, teeth, legs, pins, and/or bumps) on the sensor to penetrate between strands of hair and achieve better electroconductive contact with the person's head. In an example, the base of an electrode (e.g. EEG sensor) can be made with material with a Shore 00 value between 30 and 80 and protrusions (e.g. protrusions, prongs, teeth, legs, pins, and/or bumps) extending out from that base can be made with material with a Shore 00 value between 10 and 30. In an example, an electrode (e.g. EEG sensor) on eyewear (e.g. glasses) can have protrusions (e.g. protrusions, prongs, teeth, legs, pins, and/or bumps) which extend inward from the eyewear toward the surface of a person's head and are made from an elastomeric polymer which has been impregnated, doped, filled, and/or coated with electroconductive material.

In an example, an electrode (or electrode module) can comprise two parallel components, a first component with electroconductive protrusions (e.g. protrusions, prongs, teeth, legs, pins, and/or bumps) which is closer to the surface of a person's head and a second component which is farther from the surface of the person's head, wherein the first component rotates relative to the second component. In an example, an electrode can include a plurality of electroconductive protrusions (e.g. protrusions, prongs, teeth, legs, pins, and/or bumps) with spherical, ball-shaped, or hemispherical ends, wherein the protrusions extend out from the electrode base and have spherical ends.

In an example, eyewear (e.g. eyeglasses) can have one or more electrodes (e.g. EEG sensors) with protrusions (e.g. protrusions, prongs, teeth, legs, pins, and/or bumps) on the temples, wherein the temples are configured to bend when the eyewear is put onto a person's head, and wherein this bending motion causes the protrusions to slide relative to the surface of the person's head, thereby causing the protrusions to slide between strands of hair for better electroconductive communication with the person's head. In an example, the anterior longitudinal axis of an eyewear temple can have two upward waves, curves, bumps, loops, and/or protrusions on which two or more electrodes (e.g. EEG sensors) are located.

In an example, the anterior longitudinal axis of an eyewear temple can have an upward wave (e.g. wave, curve, bump, loop, and/or protrusion) on which an electrode (e.g. EEG sensor) is located, wherein the peak of this wave is between ½ and 2 inches above the portion(s) of the anterior longitudinal axis which are not part of the wave. In an example, there can be an upward wave (wave, curve, bump, loop, and/or protrusion) in the anterior longitudinal axis of an eyewear temple and at least one electrode (e.g. EEG sensor) on the wave, wherein the wave has a length between ½ and 3 inches. In an example, there can be an upward wave (wave, curve, bump, loop, and/or protrusion) in the anterior longitudinal axis of an eyewear temple and at least one electrode (e.g. EEG sensor) on the wave, wherein the wave has a height between ½ and 3 inches. In an example, there can be an upward wave (e.g. wave, curve, bump, loop, and/or protrusion) in the central third of the anterior longitudinal axis of an eyewear temple, wherein an electrode (e.g. EEG sensor) is located on the upward wave.

In an example, eyewear (e.g. eyeglasses) can comprise an undulating (e.g. sinusoidal) arm or protrusion which extends upward and inward from the eyewear temple, wherein one or more electrodes (e.g. EEG sensors) are on the arm or protrusion. In an example, the anterior longitudinal axis of an eyewear temple can have an upward wave (e.g. wave, curve, bump, loop, and/or protrusion) on which an electrode (e.g. EEG sensor) is located, wherein the wave has a conic section shape. In an example, a wearable device or system for monitoring and/or recording signals from a person's brain can include an electrode (e.g. EEG sensor) with a circular, elliptical, or oval shape.

In an example, the side of an electrode (e.g. EEG sensor) which faces toward the surface of a person's head can have nested circular electroconductive ridges. In an example, the shape of an eyewear frame can be adjusted (e.g. custom fit to the contour of an individual's head) by inflation of an inflatable chamber on the frame. In an example, eyewear can include an arcuate (e.g. downwardly-concave) extension (or attachment) to the eyewear front piece which holds one or more electrodes on a person's forehead above the eyewear rims. In an example, eyewear can include two arcuate (e.g. downwardly-concave) extensions (or attachments) to the eyewear front piece which hold electrodes on a person's forehead above their eyes.

In an example, eyewear (e.g. eyeglasses) worn by a person can include an eyebrow-shaped right-side arch (e.g. arch, wave, arm, or loop) over (e.g. higher than) the right-side rim of an eyewear front piece and an eyebrow-shaped left-side arch over the left-side rim of the front piece, wherein each arch has at least one electrode (e.g. EEG sensor) which is in electrical communication with the person's forehead. In an example, a wearable device or system for diagnosing, detecting, and/or predicting a health condition or event (e.g. seizure, stroke, or heart attack) can comprise: a right-side module which is slipped over the right-side temple of eyewear (e.g. eyeglasses), wherein the right-side module includes at least one electrode (e.g. EEG sensor); and a left-side module which is slipped over the left-side temple of eyewear, wherein the left-side module includes at least one electrode.

In an example, a wearable device or system for diagnosing, detecting, and/or predicting a health condition or event (e.g. seizure, stroke, or heart attack) can include a module which is removably-attached to an eyewear temple worn by a person, wherein the module includes at least one electrode (e.g. EEG sensor). In an example, a wearable device or system for diagnosing, detecting, and/or predicting a health condition or event (e.g. seizure, stroke, or heart attack) can include a module which is removably-attached by a pin or button to an eyewear temple worn by a person, wherein the module includes at least one electrode (e.g. EEG sensor).

In an example, a wearable device or system for diagnosing, detecting, and/or predicting a health condition or event (e.g. seizure, stroke, or heart attack) can include a module which is removably-attached to eyewear (e.g. glasses) by slipping the module over a temple (e.g. sidepiece) of the eyewear, wherein the module includes at least one electrode (e.g. EEG sensor). In an example, a wearable device or system for predicting and detecting neurological seizures can include a module with at least one electrode (e.g. EEG sensor) which is removably-attached to an eyewear temple at two places along the longitudinal axis of the anterior portion of the temple.

In an example, a wearable device or system for predicting and detecting neurological seizures can comprise an arcuate module with at least two electrodes (e.g. EEG sensors) which monitor and/or record electrical signals from a person's brain, wherein the module is removably-attached to eyewear (e.g. eyeglasses) worn by the person, wherein at least one of the electrodes is anterior to where the module is attached to the temple, and at least one of the electrodes is posterior to where the module is attached to the temple. In an example, a wearable device or system for predicting and detecting neurological seizures can comprise an arcuate module with at least one electrode (e.g. EEG sensor) which monitors and/or records electrical signals from a person's brain, wherein the module is removably-attached to the temple of eyewear (e.g. eyeglasses), wherein the arcuate module has a crescent, kidney-bean, or banana shape, wherein the longitudinal axis of the module is substantially perpendicular to the longitudinal axis of the temple, and wherein at least half of the module extends above the location where the module is attached to the temple.

In an example, a wearable device or system for predicting and detecting neurological seizures can comprise an arcuate module with at least one electrode (e.g. EEG sensor) which monitors and/or records electrical signals from a person's brain, wherein the module is removably-attached to eyewear (e.g. eyeglasses) worn by the person, and wherein at least half of the module is extends above the location where it is attached to the temple. In an example, the central longitudinal axis of the section of a temple (e.g. sidepiece) of an eyewear (e.g. eyeglasses) frame which extends from a person's auricle (outer ear) to the front piece of the eyewear can include an upward wave or curve.

In an example, the section of a temple (e.g. sidepiece) of an eyewear (e.g. eyeglasses) frame which extends from a person's auricle (outer ear) to the front piece of the eyewear can be substantially straight. In an example, the section of a temple (e.g. sidepiece) of an eyewear (e.g. eyeglasses) frame which extends from a person's auricle (outer ear) to the front piece of the eyewear can include both an upwardly-convex wave (or curve) and a downwardly-convex wave (or curve). In an example, the section of a temple (e.g. sidepiece) of an eyewear (e.g. eyeglasses) frame which extends from a person's auricle (outer ear) to the front piece of the eyewear can have a bifurcated sub-section, wherein an upper branch of the bifurcated section has an upwardly-convex wave (or curve) and a lower branch of the bifurcated section has a downwardly-convex wave (or curve).

In an example, a temple (also called a sidepiece, bow, arm, or leg) of eyewear (e.g. eyeglasses) rests on a person's auricle (e.g. outer ear) at a first location which is at a first height (when the person is standing upright), a first electrode (e.g. EEG sensor) is on the temple at a second location which is at a second height, and a second electrode is on the temple at a third location which is at a third height, wherein the second height is between ½ and 3 inches above the first height, and wherein the third height is between ½ and 3 inches above the first height.

In an example, a temple (also called a sidepiece, bow, arm, or leg) of eyewear (e.g. eyeglasses) rests on a person's auricle (e.g. outer ear) at a first location which is at a first height (when the person is standing upright), a first electrode (e.g. EEG sensor) is on the temple at a second location which is at a second height, and a second electrode is on the temple at a third location which is at a third height, wherein the second height is above the first height, wherein the third height is below the first height, wherein the second location is anterior to the first location, and wherein the third location is posterior to the first location.

In an example, the anterior section of an eyewear temple can extend from a person's auricle (outer ear) to the front piece of the eyewear, wherein this anterior section bifurcates into an upper branch and a lower branch, wherein there is at least one electrode (e.g. EEG sensor) on the upper branch. In an example, there can be at least two electrodes (e.g. EEG sensors) on the left-side eyewear temple, wherein at least one of the electrodes is anterior to the person's auricle (outer ear) and at least one of the electrodes is posterior to (e.g. behind or curved around the back of) the person's auricle.

In an example, there can be at least two electrodes (e.g. EEG sensors) on an eyewear temple, wherein at least one of the electrodes is anterior to (e.g. in front of) the person's auricle (outer ear) and at least one of the electrodes is curved around the back of the person's auricle. In an example, there can be at least two electrodes (e.g. EEG sensors) on an eyewear temple, wherein at least one electrode is at least ½ inch higher than the top of the person's auricle (outer ear) and at least one electrode is at least ½ inch below the top of the person's auricle. In an example, there can be at least two electrodes (e.g. EEG sensors) on an eyewear temple, wherein at least one electrode is at least ½ inch higher than the location where the temple rests on the person's auricle (outer ear) and at least one electrode is at least ½ inch lower than this location.

In an example, the central longitudinal axis of the section of a temple (e.g. sidepiece) of an eyewear (e.g. eyeglasses) frame which extends from a person's auricle (outer ear) to the front piece of the eyewear can be arcuate. In an example, the curvature of the posterior portion of an eyewear temple can be adjusted. In an example, the curvature of the posterior portion of an eyewear temple can be adjusted (e.g. custom fit to the contour of an individual's head) by changing the tension of a spring mechanism. In an example, a device or system for monitoring and/or recording EEG signals can include at least one electrode (e.g. EEG sensor) which is part of the anterior portion of an eyewear temple. In an example, an electrode (e.g. EEG sensor) can slide along a longitudinal track (or channel) on an eyewear temple.

In an example, an electrode (e.g. EEG sensor) can be part of (or removably-attached to) the anterior half of an eyewear temple worn by a person, wherein the electrode monitors and/or records electromagnetic signals from the person's brain (e.g. brainwaves). In an example, an electrode (e.g. EEG sensor) can be part of (or removably-attached to) an eyewear temple worn by a person, wherein the electrode monitors and/or records electromagnetic signals from the person's brain (e.g. brainwaves). In an example, an electrode (e.g. EEG sensor) can be attached to an eyewear temple by two or more springs, wherein one spring is closer to the front of the eyewear than the other. In an example, an electrode (e.g. EEG sensor) can be attached to an eyewear temple by two or more springs with different inter-coil distances.

In an example, an electrode (e.g. EEG sensor) can be attached to an eyewear temple by two or more springs which intersect (e.g. at connected to) the electrode at different angles. In an example, an electrode (e.g. EEG sensor) can be attached to an eyewear temple by both a spring and compressible foam. In an example, an electrode (or movable component holding an electrode) can have a first configuration in which it is aligned with the temple of eyewear and a second configuration in which it is not aligned with the temple, wherein the electrode (or component) is moved from its first configuration to its second configuration by being pivoted, rotated, unfolded, or bent.

In an example, an eyewear frame can include a pivoting and/or rotating arm with one or more electrodes on it, wherein the arm has a first configuration in which it is aligned with an eyewear temple and a second configuration in which it is not aligned with the temple. In an example, an eyewear frame can include a pivoting and/or rotating arm with one or more electrodes on it, wherein the arm has a first configuration in which it is parallel with the longitudinal axis of an eyewear temple and a second configuration in which (a virtual extension of) the longitudinal axis of the arm intersects the longitudinal axis at an acute angle.

In an example, an eyewear temple can have a (central) wave (e.g. wave, arch, and/or curve) which curves upward from the rest of the temple and forward onto a person's forehead, wherein there are one or more electrodes (e.g. EEG sensors) on the central wave. In an example, an eyewear temple can comprise of a plurality of interdigitating components, wherein the components can be connected (e.g. connected, linked, attached, inserted, or snapped) together in different configurations, sequences, or orders, and wherein one or more of the components includes one or more electrodes (e.g. EEG sensors) for measuring brain activity.

In an example, an eyewear temple can include a track (e.g. track, channel, slot, or groove) along which an electrode (e.g. EEG sensor) can be slid back and forth, or locked at a selected location on the temple. In an example, eyewear (e.g. eyeglasses) can have temples with electrodes (e.g. EEG sensors) on them, wherein the temples are connected to a front piece by spring-loaded hinges which press (or pull) the temples inward toward the surface of the person's head, thereby pressing the electrodes onto the surface of the person's head. In an example, eyewear (e.g. eyeglasses) can comprise: a front piece; and right and left side temples; wherein a temple is connected to the front piece by a hinge, wherein there is at least one electrode (e.g. EEG sensor) on the temple, and wherein the amount of force exerted by the electrode on the surface of the person's head is adjusted by adjusting the tension of a spring (or other tensile mechanism) attached to the hinge and/or temple.

In an example, one or more electrodes (or arms with one or more electrodes) can have a first configuration in which they are recessed onto or within an eyewear temple and a second configuration in which they extend out from the temple in order to contact the surface of a person's head, wherein the electrodes are changed from their first configuration to their second configuration (or vice versa) by one or more electromagnetic actuators. In an example, one or more electrodes (or arms with one or more electrodes) can have a first configuration in which they lay flat against the temple of eyewear and a second configuration in which they extend out from the temple at an angle in order to contact the surface of a person's head.

In an example, the central third of the anterior portion of the temple of eyewear can be wider (in a vertical plane) than the anterior and posterior thirds of the anterior portion in order to allow placement of one or more electrodes at locations which are higher than the anterior and posterior thirds of the anterior portion. In an example, the central third of the anterior portion of the temple of eyewear can be thicker (in a horizontal plane) than the anterior and posterior thirds of the anterior portion in order to allow placement of one or more electrodes at locations which are closer to the person's head than the anterior and posterior thirds of the anterior portion. In an example, the posterior end of an eyewear temple can bifurcate, wherein there is at least one electrode (e.g. EEG sensor) on an upper branch of the bifurcation and at least one electrode (e.g. EEG sensor) on a lower branch of the bifurcation.

In an example, there can be a sequence (e.g. sequence, series, and/or linear array) of electrodes (e.g. EEG sensors) along the longitudinal axis of an eyewear temple. In an example, there can be at least two electrodes (e.g. EEG sensors) on a right-side eyewear temple and at least two electrodes on a left-side eyewear temple. In an example, a strap (e.g. strap, band, loop, or arm) which loops around the back of a person's head can be attached to the posterior ends of the right-side and left-side temples of eyewear (e.g. eyeglasses), wherein there is at least one electrode (e.g. EEG sensor) on the strap.

In an example, a strap (e.g. strap, band, loop, or arm) which loops around the back of a person's head can be attached by (tension-adjustable) spring mechanisms to the posterior ends of the right-side and left-side temples of eyewear (e.g. eyeglasses), wherein there is at least one electrode (e.g. EEG sensor) on the strap. In an example, an eyewear temple can bifurcate in a horizontal plane, wherein an inner branch (e.g. branch, arm, or loop) of the temple is closer to the person's head, wherein an outer branch of the temple is farther from the person's head, and wherein there are one or more electrodes (e.g. EEG sensors) on the inner branch. In an example, an upper band (e.g. band, strap, or arm) which loops over the top (e.g. the upper third) of a person's head can be attached to the posterior-longitudinal-third of a right-side eyewear temple and to the posterior-longitudinal-third of a left-side eyewear temple, wherein there is at least one electrode (e.g. EEG sensor) on the band.

In an example, an upper band (e.g. band, strap, or arm) which loops over the top (e.g. the upper third) of a person's head can be attached to the right-side temple and to the left-side temple of eyewear (e.g. eyeglasses), wherein there is at least one electrode (e.g. EEG sensor) on the band. In an example, eyewear (e.g. eyeglasses) for monitoring and/or recording EEG signals can include a strap (e.g. strap, band, loop, or arm) which spans the middle of a person's forehead, from the right side of the forehead to the left side of the forehead, wherein there are at least two electrodes (e.g. EEG sensors) on the strap, and wherein the strap is connected to (the anterior portions of) the right-side and left-side temples of the eyewear. In an example, eyewear (e.g. eyeglasses) can include a strap (e.g. strap, band, loop, or arm) which loops over the upper portion (e.g. the upper third) of a person's head, between the right-side and left-side temples of the eyewear, wherein there is at least one electrode (e.g. EEG sensor) on the strap.

In an example, eyewear can comprise a flexible band (e.g. band, arm, strap, or strip), wherein the band includes one or more electrodes (e.g. EEG sensors), wherein the band has a first configuration in which it is retracted (e.g. coiled) onto or within an eyewear temple and a second configuration in which it is extended (e.g. uncoiled) from the temple. In an example, eyewear can comprise an elastic band (e.g. band, arm, strap, or strip) which spans a person's forehead from one temple of the eyewear to the other, wherein there are two or more electrodes (e.g. EEG sensors) on the band. In an example, a device or system for monitoring and/or recording EEG signals can include a module with at least one electrode (e.g. EEG sensor), whereon the module is removably-attached to the posterior portion of an eyewear temple.

In an example, a device or system for monitoring and/or recording EEG signals can include a module with at least one electrode (e.g. EEG sensor), whereon the module is removably-attached to the anterior portion of an eyewear temple by a (tension-adjustable) spring mechanism. In an example, a system or device for monitoring and/or recording brain activity can comprise two or more modules, wherein each module has at least one electrode (e.g. EEG sensor), and wherein each module is plugged (e.g. plugged, inserted, or snapped) into one of a plurality of different slots (e.g. slots, receptacles, or openings) along the longitudinal axis of a temple (e.g. sidepiece) of eyewear.

In an example, a wearable device or system for monitoring and/or recording signals from a person's brain can include a module with at least one electrode (e.g. EEG sensor), wherein the module is removably-attached to an eyewear temple, and wherein the module spans between 15% and 25% of the anterior portion of the temple. In an example, a wearable device or system for monitoring and/or recording signals from a person's brain can include a module with at least one electrode (e.g. EEG sensor), wherein the module is removably-attached to an eyewear temple, and wherein the module (e.g. the electrode on the module) is pressed against the surface of the person's head by compressible foam between the module and the temple.

In an example, a wearable device or system for monitoring and/or recording signals from a person's brain can include a module with at least one electrode (e.g. EEG sensor), wherein the module is removably-attached to an eyewear temple, and wherein the electrode is pressed against the surface of the person's head by a (tension-adjustable) spring between the electrode and the module. In an example, a wearable device or system for monitoring and/or recording signals from a person's brain can include a module with at least one electrode (e.g. EEG sensor), wherein the module is removably-attached to an eyewear temple, and wherein the electrode is pressed against the surface of the person's head by a length-adjustable solenoid between the electrode and the module.

In an example, a wearable device or system for monitoring and/or recording signals from a person's brain can include a module with at least one electrode (e.g. EEG sensor) which is removably-attached to an eyewear temple, wherein the module has an upper edge (or side) which is higher than (where it attaches to) the temple and a lower edge (or side) which is lower than (where it attaches to) the temple, and wherein the upper edge (or side) is at least 25% greater than the lower edge (or side). In an example, a wearable device or system for monitoring and/or recording signals from a person's brain can include a module with at least one electrode (e.g. EEG sensor) which is removably-attached to an eyewear temple, wherein the module has an anterior edge (or side) and a posterior edge (or side), and wherein the posterior edge (or side) is at least 25% greater (e.g. wider) than the anterior edge (or side).

In an example, a wearable device or system for monitoring and/or recording signals from a person's brain can include a module with at least one electrode (e.g. EEG sensor) which is removably-attached to an eyewear temple by a first attachment mechanism (e.g. clip, clasp, clamp, snap, or hook) and a second attachment mechanism (e.g. clip, clasp, clamp, snap, or hook), wherein the first attachment mechanism is a first distance from the front piece, the second attachment mechanism is a second distance from the front piece, and the second distance is at least ½ inch greater than the first distance. In an example, an electrode (or electrode module) can include one or more rings which slide onto (or over) an eyewear temple.

In an example, an electrode (or electrode module) can have a clip (e.g. clip, clasp, clamp, or hook) which is moveably-attached to an eyewear temple, whereby the electrode (or electrode module) can be attached to each of several different locations on the longitudinal axis of the temple, thereby enabling adjustment of the location of the electrode (or electrode module). In an example, an electrode (or electrode module) can have a sleeve (e.g. sleeve, channel, track or slot) into which an eyewear temple is inserted, whereby the electrode (or electrode module) can slide to each of several different locations on the longitudinal axis of the temple, thereby enabling adjustment of the location of the electrode (or electrode module).

In an example, an electrode (or electrode module) can be attached to an eyewear temple by two or more springs of different sizes. In an example, an electrode (or electrode module) can be attached to an eyewear temple by one or more tension-adjustable springs. In an example, an electrode (e.g. EEG sensor) or electrode module can be moved backward or forward (e.g. slid in a posterior direction or in anterior direction) along the longitudinal axis an eyewear temple and also locked (e.g. snapped, clipped, or clamped) into place at a selected location on the temple, thereby enabling adjustment of the location where the electrode contacts the surface of a person's head.

In an example, an eyewear temple can have a plurality of receptacles (e.g. receptacles, ports, slots, openings, holes) into which one or more electrodes (or electrode modules) can be selectively inserted (e.g. inserted or plugged), thereby enabling customization (e.g. varying and selective placement) of the locations of one or more electrodes along the temple. In an example, an eyewear temple can comprise of a series of at least modular components which can be connected (e.g. connected, attached, inserted, snapped, or clipped) together in different configurations, sequences, or orders, wherein one or more of the components include one or more electrodes (e.g. EEG sensors) for measuring brain activity. In an example, an eyewear temple can comprise a plurality of modular components which can connect to each other in different longitudinal configurations, sequences, and/or orders, wherein one or more of the components include one or more electrodes (e.g. EEG sensors) for measuring brain activity.

In an example, one or more electrode modules can be selectively and reversibly connected to different locations on a temple of an eyewear frame, wherein each module contains a power source and data processing unit as well as an electrode. In an example, there can be a plurality of slots (e.g. slots, receptacles, ports, and/or openings) on an eyewear temple into which one or more electrodes (or electrode modules) can be inserted. In an example, a (modular) EEG monitoring system can include a strap (e.g. strap, band, loop, or arm) which loops over the top (e.g. the upper third) of a person's head, wherein the strap is removably-attached to the right-side and left-side temples of eyewear (e.g. eyeglasses), and wherein there is at least one electrode (e.g. EEG sensor) on the strap.

In an example, a (modular) EEG monitoring system can include a flexible (e.g. flexible and elastic) strap (e.g. strap, band, loop, or arm) which loops over the top (e.g. the upper third) of a person's head, wherein the strap is removably-attached to the right-side and left-side temples of eyewear (e.g. eyeglasses), and wherein there is at least one electrode (e.g. EEG sensor) on the strap. In an example, a module with one or more electrodes can comprise an anterior connector (e.g. clip, clasp, clamp, hook, loop, strap, magnet, or hook-and-loop fabric) which attaches the module to an eyewear temple at a first location and a posterior connector (e.g. clip, clasp, clamp, hook, loop, strap, magnet, or hook-and-loop fabric) which attaches the module to the temple at a second location, wherein the anterior connector is at least ½ inch closer to the front piece of the eyewear than the posterior connector.

In an example, a wearable device or system for monitoring and/or recording signals from a person's brain can include a module with at least one electrode (e.g. EEG sensor) which is removably-attached to an eyewear temple by two hook and loop pieces (e.g. bands), wherein the two hook and loop pieces (e.g. bands) are at least ½ inch apart from each other. In an example, a wearable device or system for monitoring and/or recording signals from a person's brain can include a kidney-bean, crescent, or banana shaped module with an electrode (e.g. EEG sensor), wherein the module is removably-attached to an eyewear (e.g. eyeglasses) frame, and wherein the longitudinal axis of the module is substantially perpendicular to the longitudinal axis of an eyewear temple when attached.

In an example, a wearable device or system for monitoring and/or recording signals from a person's brain can include a circular, elliptical, or oval module with an electrode (e.g. EEG sensor), wherein the module can be removably-attached to an eyewear (e.g. eyeglasses) frame, and wherein the longitudinal axis of the module is substantially perpendicular to the longitudinal axis of an eyewear temple when attached. In an example, a wearable device or system for monitoring and/or recording signals from a person's brain can include an electrode (e.g. EEG sensor) module with a circular, elliptical, or oval shape which is removably-attached to the temple of an eyewear frame. In an example, an electrode module with one or more electrodes (e.g. EEG sensors) which is removably-attached to an eyewear temple can have a saddle shape.

In an example, an electrode module with one or more electrodes (e.g. EEG sensors) which is removably-attached to an eyewear temple can have a dumbbell, dog-bone, or figure eight shape. In an example, eyewear (e.g. eyeglasses) can comprise six electrodes (e.g. EEG sensors), two on each temple of the eyewear frame and two on the front piece (e.g. on the nose pads) of the eyewear frame. In an example, an eyewear temple can have a (longitudinal axis with a) shape comprising one phase of a sinusoidal curve. In an example, an eyewear temple can have a (longitudinal axis with a) shape comprising a segment of a sinusoidal curve which is less than one phase of a sinusoidal curve.

In an example, a foam piece between the temple of eyewear and an electrode can be custom-shaped based on 3D imaging of (the size and shape of) an individual's head. In an example, eyewear (e.g. eyeglasses) can comprise an arcuate (e.g. quarter-circle) arm which extends upward, inward, and forward (e.g. anteriorly) from the eyewear temple, wherein one or more electrodes (e.g. EEG sensors) are on the arm. In an example, eyewear (e.g. eyeglasses) can comprise an arcuate (e.g. quarter-circle) arm which extends upward, inward, and forward (e.g. anteriorly) from the anterior third of the eyewear temple, wherein one or more electrodes (e.g. EEG sensors) are on the arm.

In an example, eyewear (e.g. eyeglasses) can comprise an arcuate (e.g. quarter-circle) arm which extends upward and forward (e.g. anteriorly) from the eyewear temple, wherein one or more electrodes (e.g. EEG sensors) are on the arm. In an example, eyewear (e.g. eyeglasses) can comprise an arcuate (e.g. quarter-circle) arm which extends upward and forward (e.g. anteriorly) from anterior third of the eyewear temple, wherein one or more electrodes (e.g. EEG sensors) are on the arm. In an example, an eyewear temple can bifurcate, wherein there is a kidney-bean, crescent, or banana shaped opening (e.g. opening, hole, or gap) between the upper branch (e.g. branch, arm, or loop) of the bifurcation and the lower branch of the bifurcation, and wherein there are one or more electrodes (e.g. EEG sensors) on one or both of the branches.

In an example, eyewear (e.g. eyeglasses) can comprise an undulating (e.g. sinusoidal) loop or wave which extends upward and inward from the eyewear temple, wherein one or more electrodes (e.g. EEG sensors) are on the loop or wave. In an example, eyewear (e.g. eyeglasses) can comprise an arcuate loop or wave which extends upward, inward, and forward (e.g. anteriorly) from the (longitudinally) central one-third of the eyewear temple, wherein one or more electrodes (e.g. EEG sensors) are on the loop or wave. In an example, eyewear (e.g. eyeglasses) can comprise an arcuate loop or wave which extends upward and inward from the eyewear temple, wherein one or more electrodes (e.g. EEG sensors) are on the loop or wave. In an example, eyewear (e.g. eyeglasses) can comprise an arcuate loop or wave which extends upward and forward (e.g. anteriorly) from (longitudinally) central one-third of the eyewear temple, wherein one or more electrodes (e.g. EEG sensors) are on the loop or wave.

In an example, eyewear (e.g. eyeglasses) with electrodes (e.g. EEG sensors) can collect brain activity data (e.g. electroencephalographic data) which is used to predict and/or detect health events (e.g. seizure, stroke, or heart attack) and/or function as a BCI (Brain-to-Computer Interface) for communication. In an example, this eyewear with electrodes can comprise: a front piece; two temples (e.g. sidepieces); at least one an anterior electrode (e.g. EEG sensor); and at least one a posterior electrode (e.g. EEG sensor), wherein a temple is conceptually divided into an anterior portion which is anterior to where the temple rests on a person's auricle and a posterior portion which is posterior to where the temple rests on the person's auricle, wherein anterior electrode is on the anterior portion of a temple, and wherein the posterior electrode is on the posterior portion of the temple.

In an example, an anterior portion of a temple can have an upward wave, wherein there is at least one electrode on this wave. In an example, an anterior portion of a temple can have an inward (toward a person's head) wave, wherein there is at least one electrode on this wave. In an example, eyewear can further comprise an arm which extends out from the anterior portion of a temple, wherein there is at least one electrode on this arm. In an example, this arm can curve upward and forward. In an example, eyewear can further comprise a forehead band which spans a person's forehead from a left-side temple to a right-side temple, wherein there is at least one electrode on this band. In an example, eyewear can further comprise an arm which extends out from the posterior portion of a temple, wherein there is at least one electrode on this arm. In an example, this arm can be the upper branch of a bifurcation of the posterior portion of the temple. In an example, an anterior portion of a temple can bifurcate, wherein the upper branch of this bifurcation is an upper wave, and wherein there is at least one electrode on this wave.

In an example, a front piece of eyewear can further comprise a concave (e.g. arch-shaped) arm above each rim, wherein there is at least one electrode on each arm. In an example, eyewear can further comprise a posterior band which spans the back of a person's head from the left-side temple to the right-side temple, wherein there is at least one electrode on this band. In an example, eyewear can further comprise an upper band which loops over the top (e.g. the upper one-third) of a person's head from a left-side temple to a right-side temple, wherein there is at least one electrode on this band. In an example, a front piece of eyewear can further comprise a brow bow (also called a top bow) which spans part of a person's forehead from a left-side rim to a right-side rim, wherein there is at least one electrode on this bow.

This disclosure now transitions from the preceding introductory section to discussion of specific embodiments shown in FIGS. 1-44. Of these, FIGS. 1-36 focus primarily on overall designs for eyewear (e.g. eyeglasses) with electrodes (e.g. EEG sensors). FIGS. 37-44 then provide some detailed examples of how electrodes can be configured and/or held onto the eyewear frames. The details for electrode configuration and attachment provided in FIGS. 37-44 can be applied to any of the eyewear designs shown in FIGS. 1-36. More generally, relevant variations discussed in the preceding introductory section of this disclosure, or in priority-linked disclosures, can also be applied to the examples shown in these figures.

Figure 2:
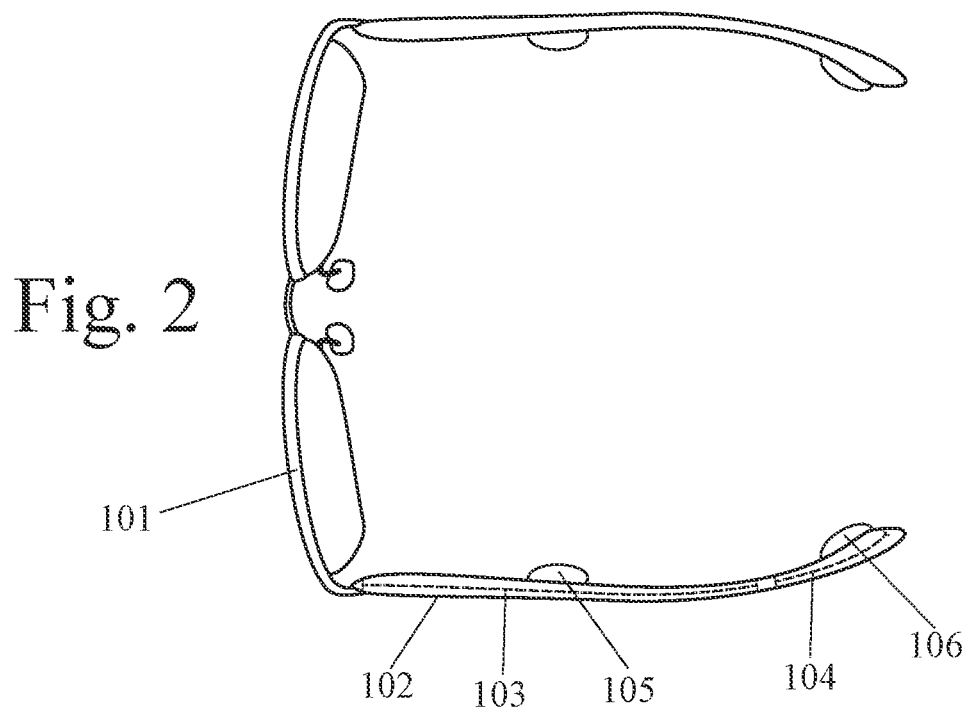
Figure 3:
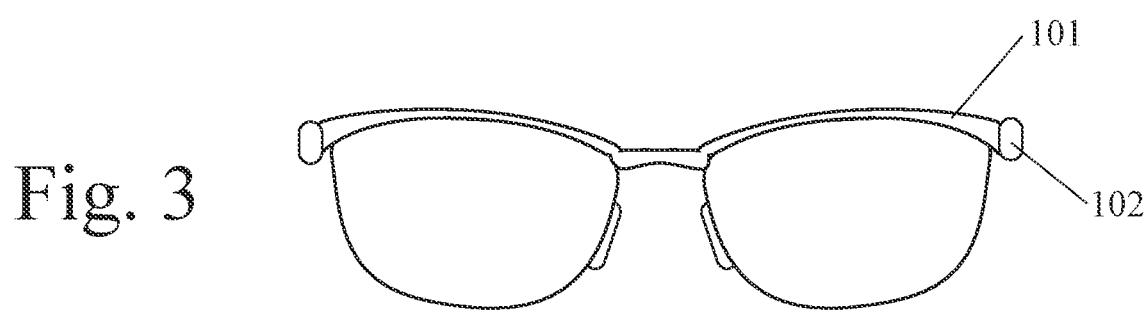

FIGS. 1-3 show three different views of an example of eyewear (e.g. eyeglasses) with electrodes (e.g. EEG sensors) which can collect brain activity data (e.g. electroencephalographic data) which can be used to predict and/or detect health events (e.g. seizure, stroke, or heart attack) or function as a BCI (Brain-to-Computer Interface) for communication. FIG. 1 shows a side view of the left-side temple (e.g. sidepiece) and the front piece of the eyewear. FIG. 2 shows a top-down view of both the left-side and right-side temples and the front piece of the eyewear. FIG. 3 shows a frontal view of the front piece of the eyewear and the front ends of the temples.

With respect to specific components, the eyewear shown in FIGS. 1-3 comprises: a front piece 101; a temple (e.g. sidepiece) 102; an anterior electrode (e.g. EEG sensor) 105 on an anterior portion of the temple; and a posterior electrode (e.g. EEG sensor) 106 on a posterior portion of the temple. FIGS. 1-3 shows the temple being conceptually divided into an anterior portion 103 (which is anterior to where the temple rests on a person's auricle) and a posterior portion 104 (which is posterior to where the temple rests on the person's auricle). In an example, the side of an anterior electrode which faces toward a person's head can be substantially flat and the side of a posterior electrode which faces toward the person's head can have a plurality of electroconductive protrusions (e.g. protrusions, prongs, teeth, legs, pins, and/or bumps) which contact the surface of the person's head. In these figures, only left-side components are labeled, but right-side components which are symmetric to those on the left side can be assumed. Specification details and variations discussed in the introductory section of this disclosure or in priority-linked disclosures can be applied to this example where relevant.

Figure 4:
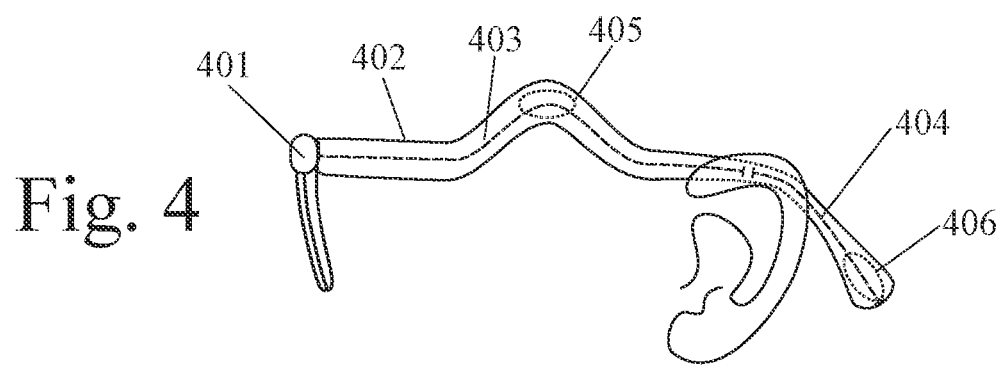
FIGS. 4-6 show three views of eyewear with a temple with an upward wave, an anterior electrode on the wave, and a posterior electrode.
Figure 5:
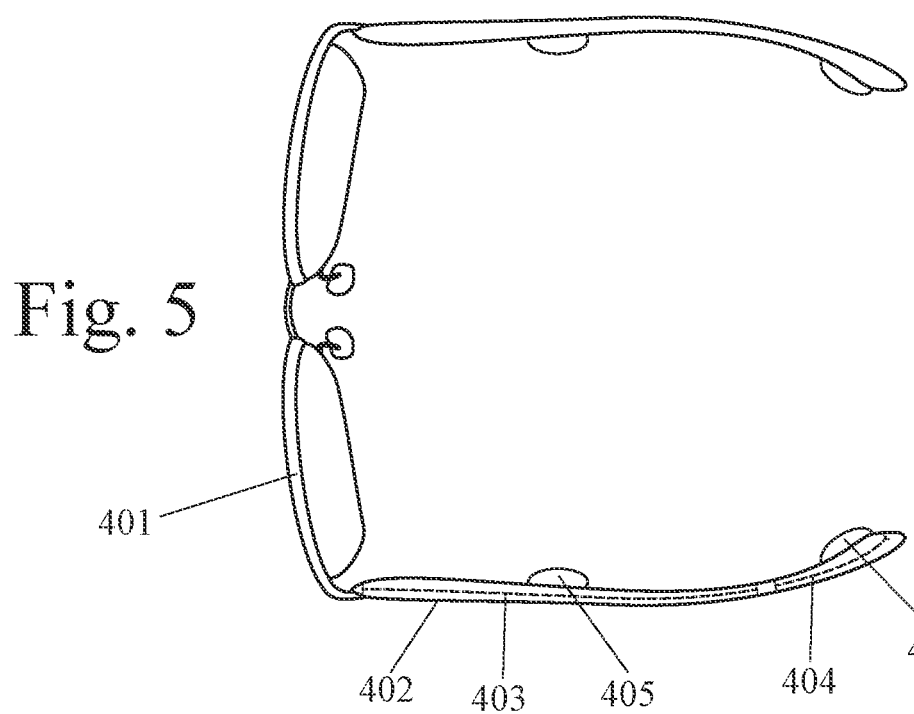
Figure 6:
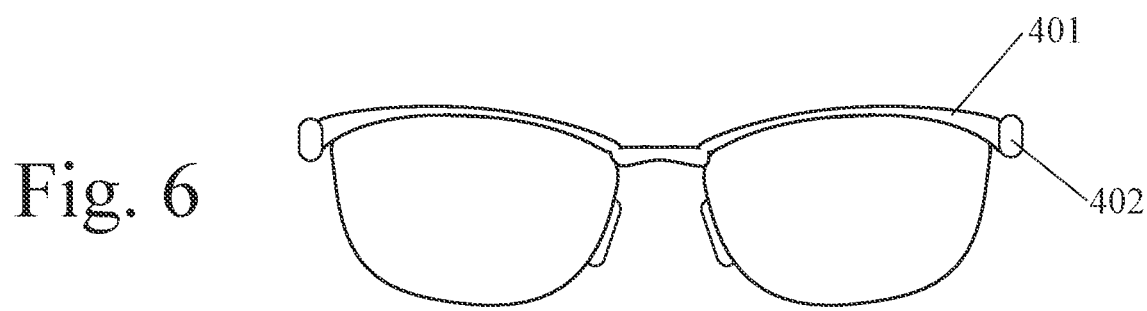

FIGS. 4-6 show three different views of an example of eyewear (e.g. eyeglasses) with electrodes (e.g. EEG sensors) which can collect brain activity data (e.g. electroencephalographic data) which can be used to predict and/or detect health events (e.g. seizure, stroke, or heart attack) or function as a BCI (Brain-to-Computer Interface) for communication. FIG. 4 shows a side view of the left-side temple (e.g. sidepiece) and the front piece of the eyewear. FIG. 5 shows a top-down view of both the left-side and right-side temples and the front piece of the eyewear. FIG. 6 shows a frontal view of the front piece of the eyewear and the front ends of the temples.

With respect to specific components, the eyewear shown in FIGS. 4-6 comprises: a front piece 401; a temple (e.g. sidepiece) 402; an anterior electrode (e.g. EEG sensor) 405 on an upward wave of an anterior portion of the temple; and a posterior electrode (e.g. EEG sensor) 406 on a posterior portion of the temple. FIGS. 4-6 show the temple being conceptually divided into an anterior portion 403 (which is anterior to where the temple rests on a person's auricle) and a posterior portion 404 (which is posterior to where the temple rests on the person's auricle). In an example, the side of an anterior electrode which faces toward a person's head can be substantially flat and the side of a posterior electrode which faces toward the person's head can have a plurality of electroconductive protrusions (e.g. protrusions, prongs, teeth, legs, pins, and/or bumps) which contact the surface of the person's head. In these figures, only left-side components are labeled, but right-side components which are symmetric to those on the left side can be assumed. Specification details and variations discussed in the introductory section of this disclosure or in priority-linked disclosures can be applied to this example where relevant.

Figure 7:
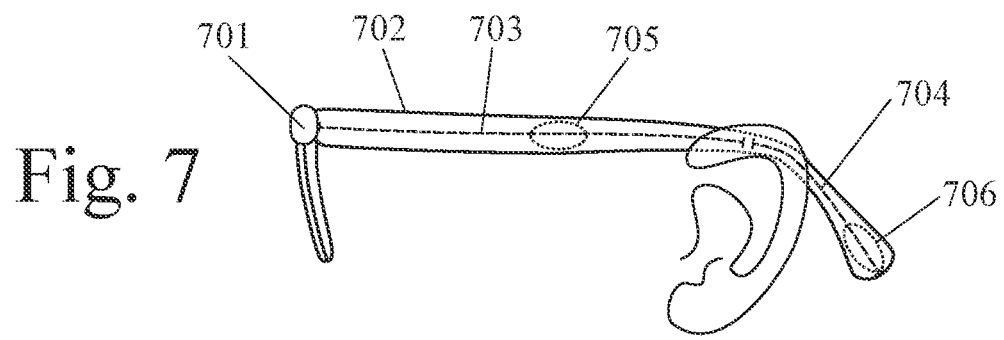
FIGS. 7-9 show three views of eyewear with a temple with an inward wave, an anterior electrode on the wave, and a posterior electrode.
Figure 8:
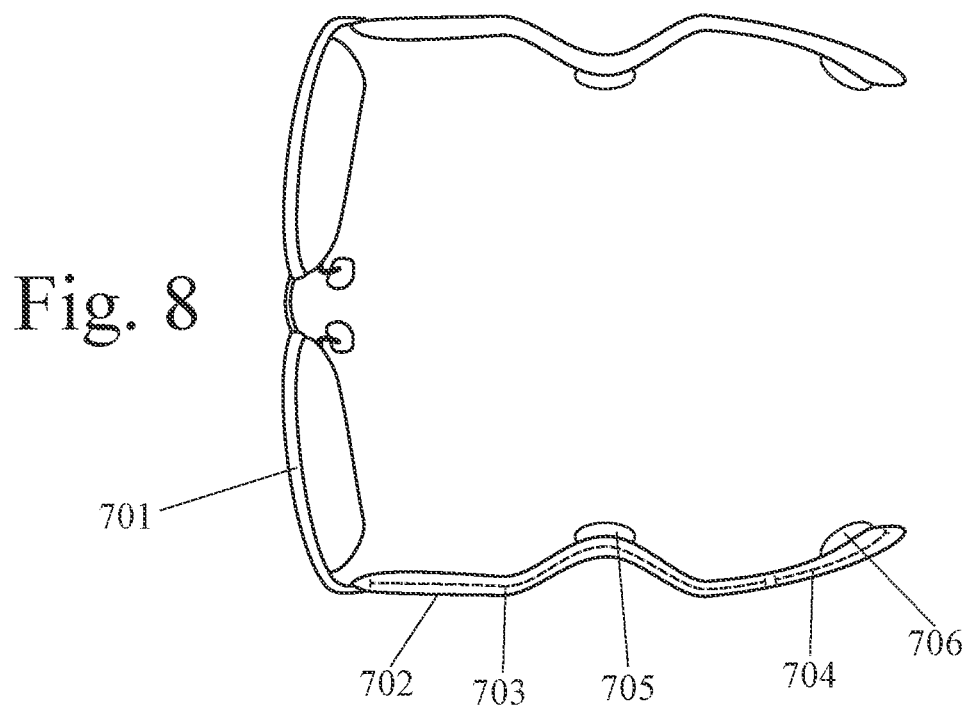
Figure 9:
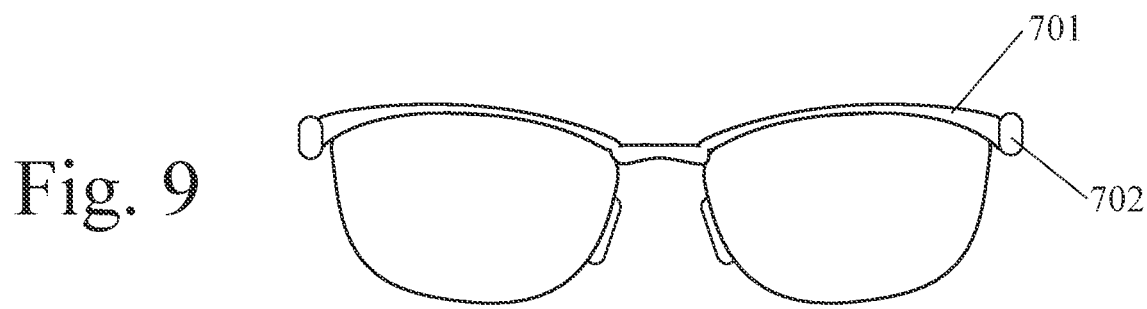

FIGS. 7-9 show three different views of an example of eyewear (e.g. eyeglasses) with electrodes (e.g. EEG sensors) which can collect brain activity data (e.g. electroencephalographic data) which can be used to predict and/or detect health events (e.g. seizure, stroke, or heart attack) or function as a BCI (Brain-to-Computer Interface) for communication. FIG. 7 shows a side view of the left-side temple (e.g. sidepiece) and the front piece of the eyewear. FIG. 8 shows a top-down view of the left-side and right-side temples and the front piece of the eyewear. FIG. 9 shows a frontal view of the front piece of the eyewear and the front ends of the temples.

With respect to specific components, the eyewear shown in FIGS. 7-9 comprises: a front piece 701; a temple (e.g. sidepiece) 702; an anterior electrode (e.g. EEG sensor) 705 on an inward (toward the person's head) wave in the anterior portion of the temple; and a posterior electrode (e.g. EEG sensor) 706 on the posterior portion of the temple. FIGS. 7-9 show the temple being conceptually divided into an anterior portion 703 (which is anterior to where the temple rests on a person's auricle) and a posterior portion 704 (which is posterior to where the temple rests on the person's auricle). In an example, the side of an anterior electrode which faces toward a person's head can be substantially flat and the side of a posterior electrode which faces toward the person's head can have a plurality of electroconductive protrusions (e.g. protrusions, prongs, teeth, legs, pins, and/or bumps) which contact the surface of the person's head. In these figures, only left-side components are labeled, but right-side components which are symmetric to those on the left side can be assumed. Specification details and variations discussed in the introductory section of this disclosure or in priority-linked disclosures can be applied to this example where relevant.

Figure 10:
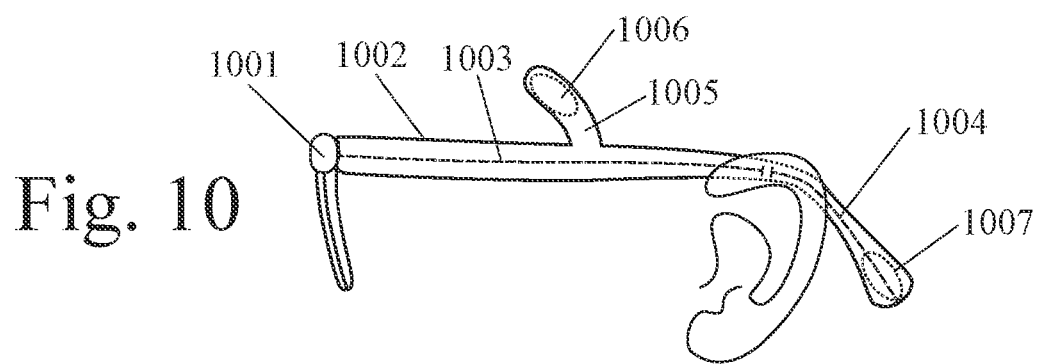
FIGS. 10-12 show three views of eyewear with a temple with an anterior extended arm, an electrode on the arm, and a posterior electrode.
Figure 11:
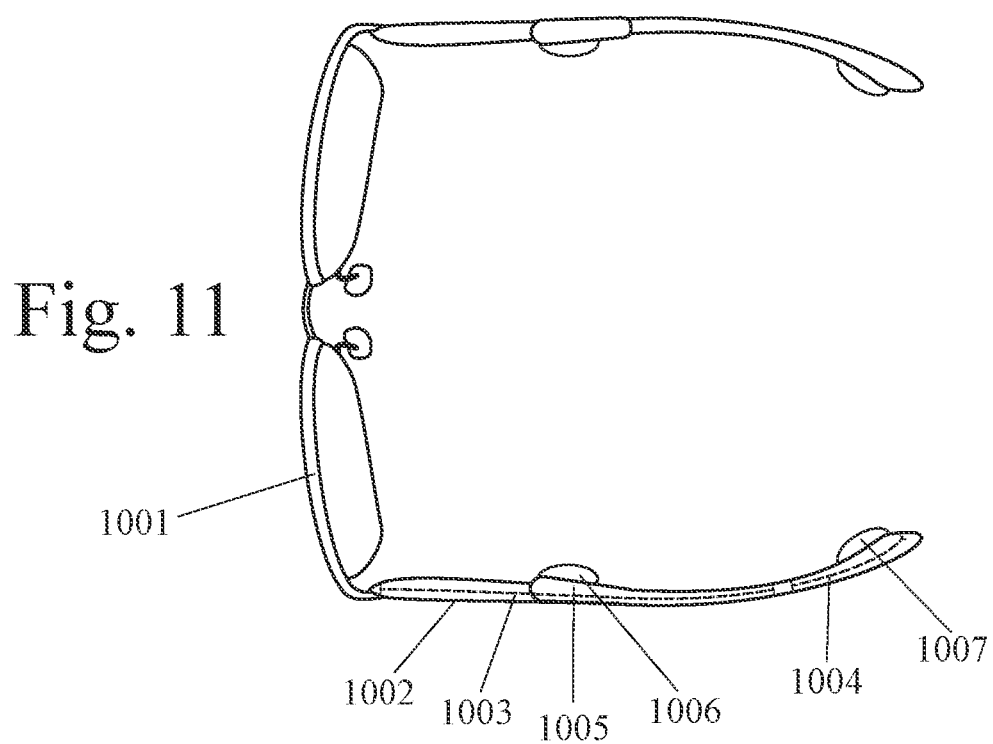
Figure 12:
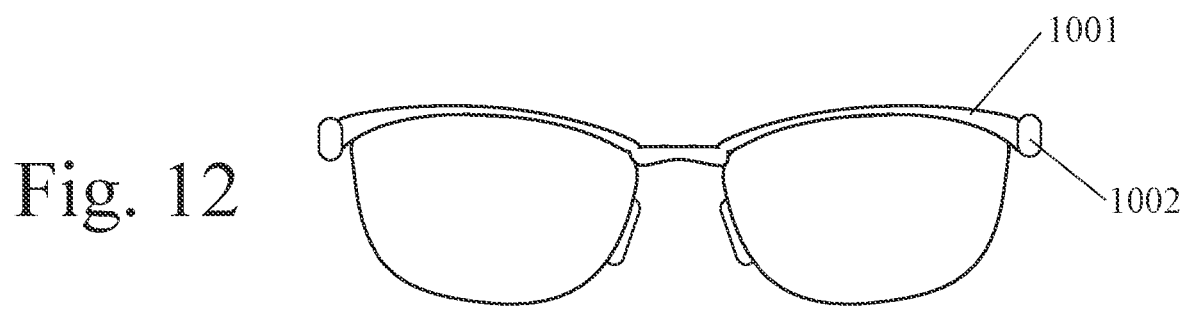

FIGS. 10-12 show three different views of an example of eyewear (e.g. eyeglasses) with electrodes (e.g. EEG sensors) which can collect brain activity data (e.g. electroencephalographic data) which can be used to predict and/or detect health events (e.g. seizure, stroke, or heart attack) or function as a BCI (Brain-to-Computer Interface) for communication. FIG. 10 shows a side view of the left-side temple (e.g. sidepiece) and the front piece of the eyewear. FIG. 11 shows a top-down view of both the left-side and right-side temples and the front piece of the eyewear. FIG. 12 shows a frontal view of the front piece of the eyewear and the front ends of the temples.

With respect to specific components, the eyewear shown in FIGS. 10-12 comprises: a front piece 1001; a temple (e.g. sidepiece) 1002; an anterior electrode (e.g. EEG sensor) 1006 on an arm 1005 which extends out from an anterior portion of the temple; and a posterior electrode (e.g. EEG sensor) 1007 on the posterior portion of the temple. FIGS. 10-12 show the temple being conceptually divided into an anterior portion 1003 (which is anterior to where the temple rests on a person's auricle) and a posterior portion 1004 (which is posterior to where the temple rests on the person's auricle). In an example, the side of an anterior electrode which faces toward a person's head can be substantially flat and the side of a posterior electrode which faces toward the person's head can have a plurality of electroconductive protrusions (e.g. protrusions, prongs, teeth, legs, pins, and/or bumps) which contact the surface of the person's head. In these figures, only left-side components are labeled, but right-side components which are symmetric to those on the left side can be assumed. Specification details and variations discussed in the introductory section of this disclosure or in priority-linked disclosures can be applied to this example where relevant.

Figure 13:
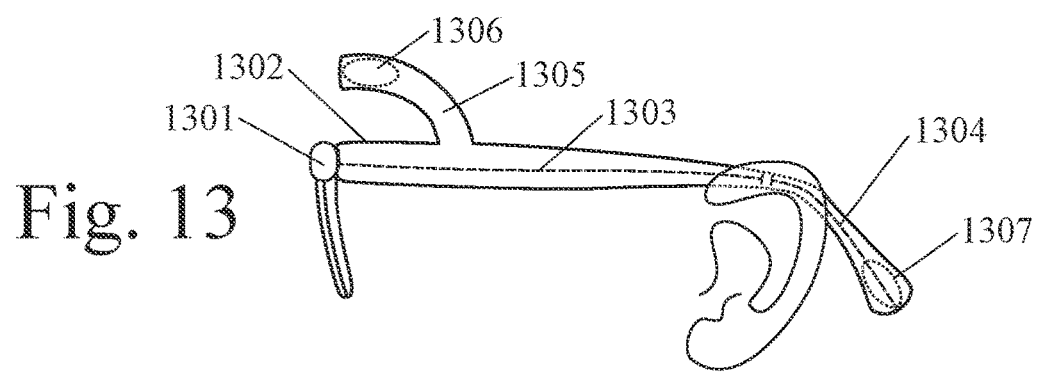
FIGS. 13-15 show three views of eyewear with an electrode on a temple and an electrode on a forehead band.
Figure 14:
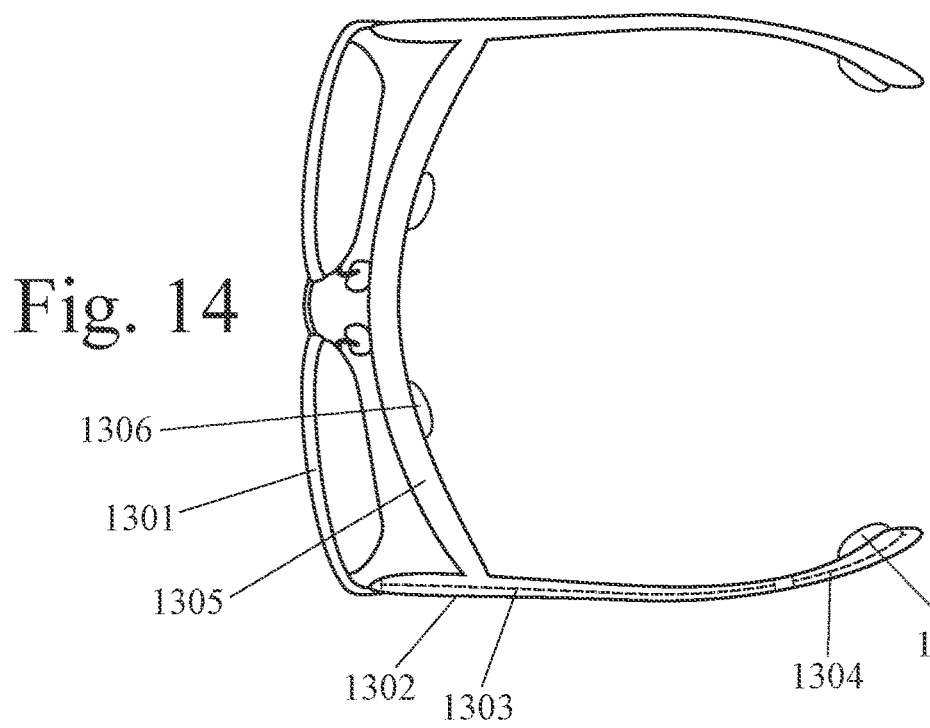
Figure 15:
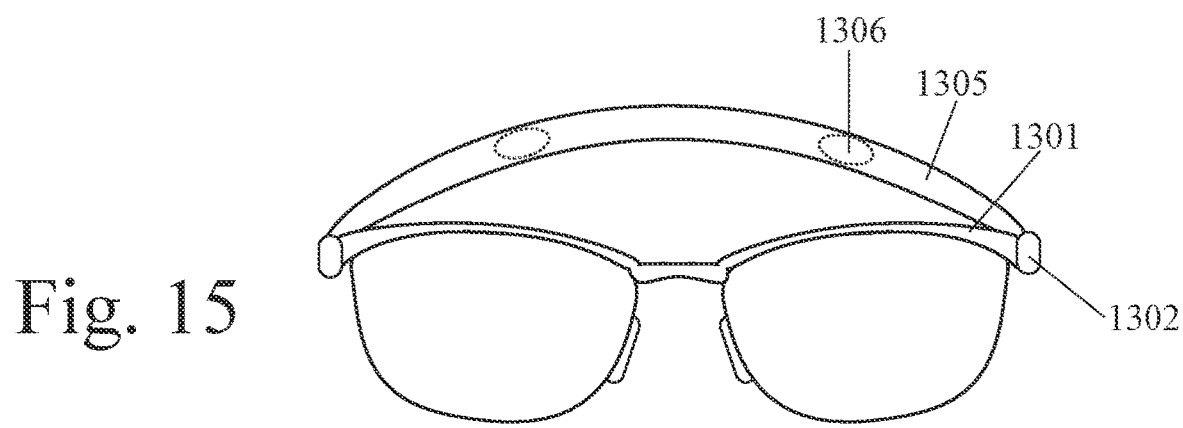

FIGS. 13-15 show three different views of an example of eyewear (e.g. eyeglasses) with electrodes (e.g. EEG sensors) which can collect brain activity data (e.g. electroencephalographic data) which can be used to predict and/or detect health events (e.g. seizure, stroke, or heart attack) or function as a BCI (Brain-to-Computer Interface) for communication. FIG. 13 shows a side view of the left-side temple (e.g. sidepiece) of the eyewear, a forehead band (or strap) which spans a person's forehead from the left-side temple to the right-side temple, and the front piece of the eyewear. FIG. 14 shows a top-down view of the left-side and right-side temples, the forehead band (or strap), and the front piece of the eyewear. FIG. 15 shows a frontal view of the front piece of the eyewear, the forehead band (or strap), and the front ends of the temples.

With respect to specific components, the eyewear shown in FIGS. 13-15 comprises: a front piece 1301; a temple (e.g. sidepiece) 1302; an anterior electrode (e.g. EEG sensor) 1306 on a forehead band (or strap) 1305 which spans a person's forehead from the left-side temple to the right-side temple; and a posterior electrode (e.g. EEG sensor) 1307 on the posterior portion of the temple. FIGS. 13-15 show the temple being conceptually divided into an anterior portion 1303 (which is anterior to where the temple rests on a person's auricle) and a posterior portion 1304 (which is posterior to where the temple rests on the person's auricle). In an example, the side of an anterior electrode which faces toward a person's head can be substantially flat and the side of a posterior electrode which faces toward the person's head can have a plurality of electroconductive protrusions (e.g. protrusions, prongs, teeth, legs, pins, and/or bumps) which contact the surface of the person's head. In these figures, only left-side components are labeled, but right-side components which are symmetric to those on the left side can be assumed. Specification details and variations discussed in the introductory section of this disclosure or in priority-linked disclosures can be applied to this example where relevant.

Figure 16:
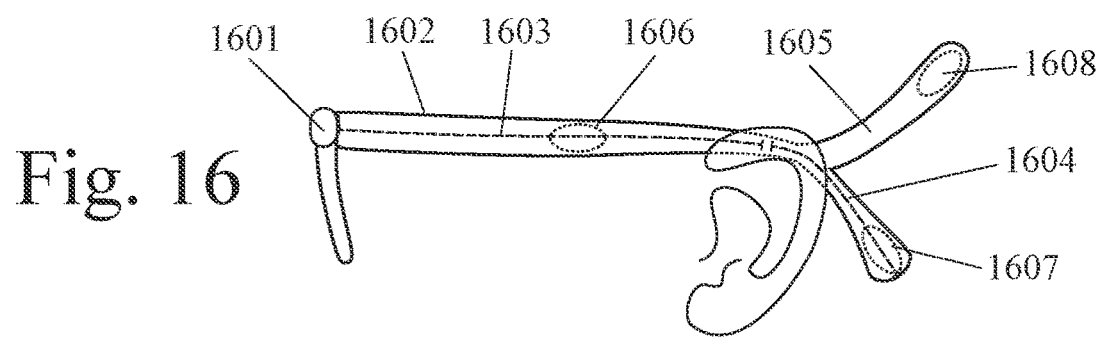
FIGS. 16-18 show three views of eyewear with a temple with a posterior extended arm, an electrode on the arm, and an electrode on the anterior of the temple.
Figure 17:
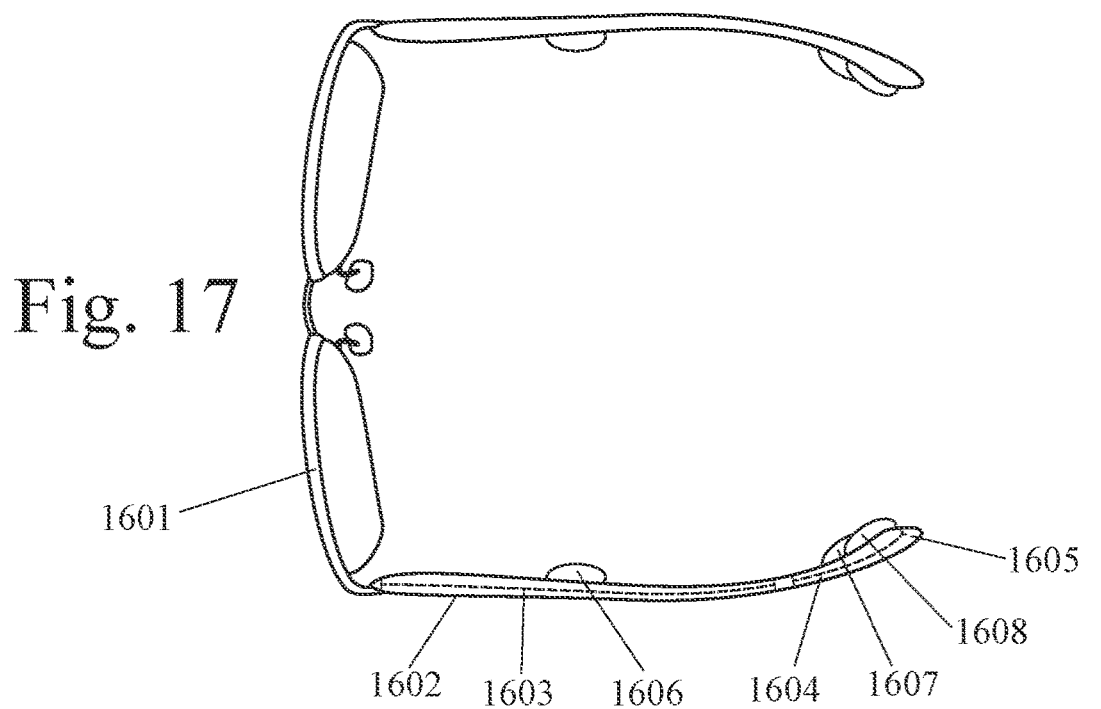
Figure 18:
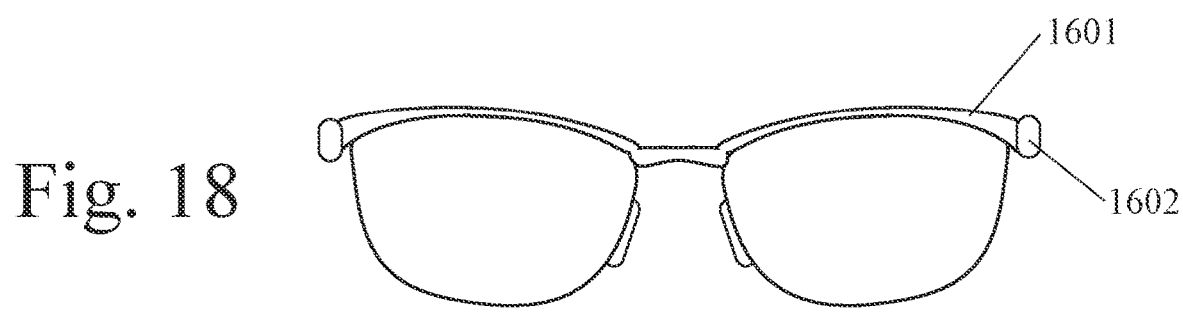

FIGS. 16-18 show three different views of an example of eyewear (e.g. eyeglasses) with electrodes (e.g. EEG sensors) which can collect brain activity data (e.g. electroencephalographic data) which can be used to predict and/or detect health events (e.g. seizure, stroke, or heart attack) or function as a BCI (Brain-to-Computer Interface) for communication. FIG. 16 shows a side view of the left-side temple (e.g. sidepiece) of the eyewear and the front piece of the eyewear. FIG. 17 shows a top-down view of the left-side and right-side temples and the front piece of the eyewear. FIG. 18 shows a frontal view of the front piece of the eyewear and the front ends of the temples.

With respect to specific components, the eyewear shown in FIGS. 16-18 comprises: a front piece 1601; a temple (e.g. sidepiece) 1602; an anterior electrode (e.g. EEG sensor) 1606 on the anterior portion of the temple; and two posterior electrodes (e.g. EEG sensors), 1607 and 1608, wherein one of the two posterior electrodes is on an arm 1605 which extends out from the posterior portion of the temple. FIGS. 16-18 show the temple being conceptually divided into an anterior portion 1603 (which is anterior to where the temple rests on a person's auricle) and a posterior portion 1604 (which is posterior to where the temple rests on the person's auricle). In an example, the side of an anterior electrode which faces toward a person's head can be substantially flat and the side of a posterior electrode which faces toward the person's head can have a plurality of electroconductive protrusions (e.g. protrusions, prongs, teeth, legs, pins, and/or bumps) which contact the surface of the person's head. In these figures, only left-side components are labeled, but right-side components which are symmetric to those on the left side can be assumed. Specification details and variations discussed in the introductory section of this disclosure or in priority-linked disclosures can be applied to this example where relevant.

Figure 19:
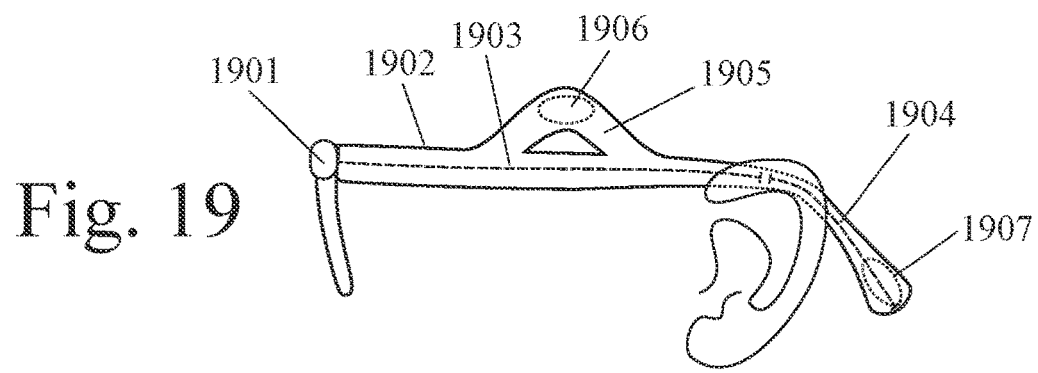
FIGS. 19-21 show three views of eyewear with a temple with an anterior bifurcation, an anterior electrode on the bifurcation, and a posterior electrode.
Figure 20:
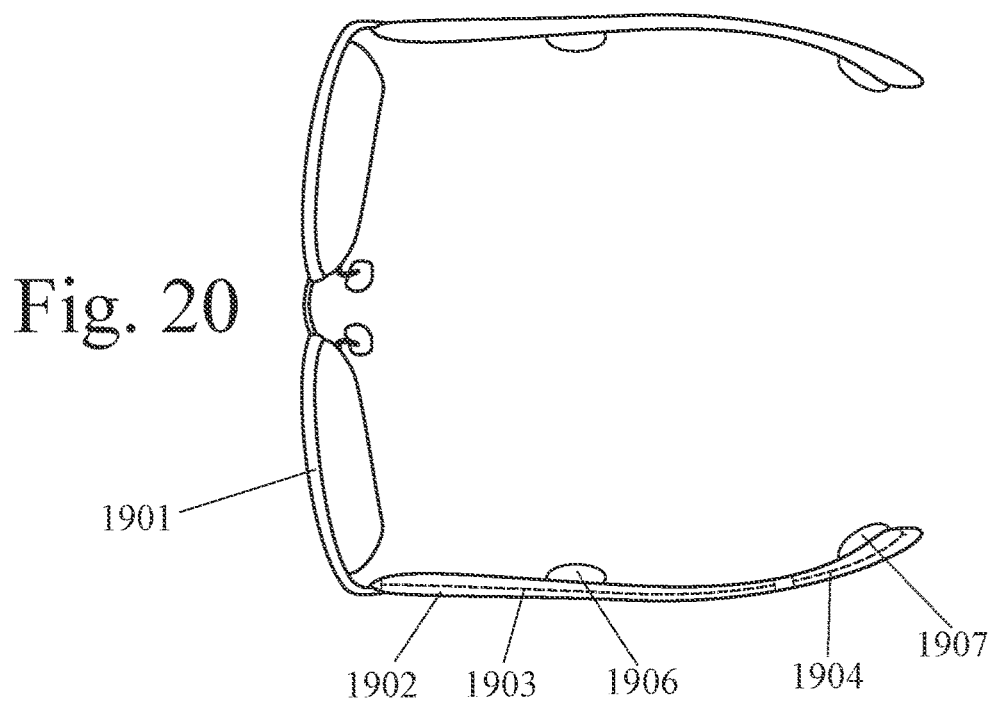
Figure 21:
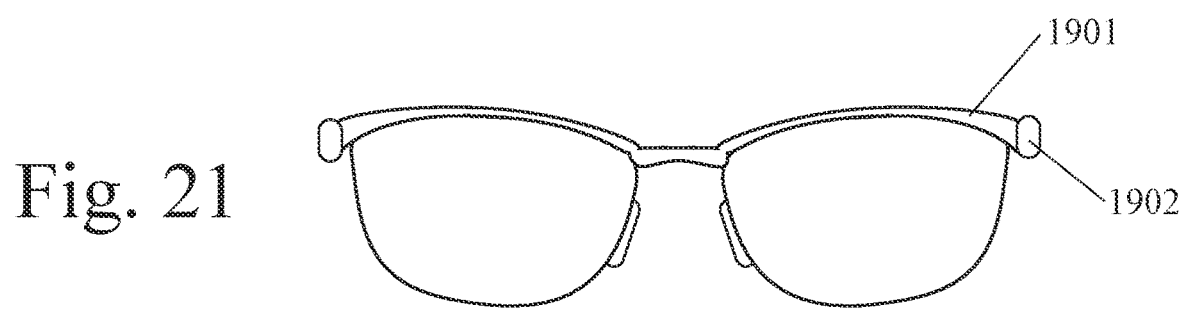

FIGS. 19-21 show three different views of an example of eyewear (e.g. eyeglasses) with electrodes (e.g. EEG sensors) which can collect brain activity data (e.g. electroencephalographic data) which can be used to predict and/or detect health events (e.g. seizure, stroke, or heart attack) or function as a BCI (Brain-to-Computer Interface) for communication. FIG. 19 shows a side view of the left-side temple (e.g. sidepiece) of the eyewear and the front piece of the eyewear. FIG. 20 shows a top-down view the left-side and right-side temples and the front piece of the eyewear. FIG. 21 shows a frontal view of the front piece of the eyewear and the front ends of the temples.

With respect to specific components, the eyewear shown in FIGS. 19-21 comprises: a front piece 1901; a temple (e.g. sidepiece) 1902 with an anterior portion which bifurcates; an anterior electrode (e.g. EEG sensor) 1906 on an upper branch 1905 of the bifurcation; and a posterior electrode (e.g. EEG sensor) 1907 on a posterior portion of the temple. FIGS. 19-21 show the temple being conceptually divided into an anterior portion 1903 (which is anterior to where the temple rests on a person's auricle) and a posterior portion 1904 (which is posterior to where the temple rests on the person's auricle). In an example, the side of an anterior electrode which faces toward a person's head can be substantially flat and the side of a posterior electrode which faces toward the person's head can have a plurality of electroconductive protrusions (e.g. protrusions, prongs, teeth, legs, pins, and/or bumps) which contact the surface of the person's head. In these figures, only left-side components are labeled, but right-side components which are symmetric to those on the left side can be assumed. Specification details and variations discussed in the introductory section of this disclosure or in priority-linked disclosures can be applied to this example where relevant.

Figure 22:
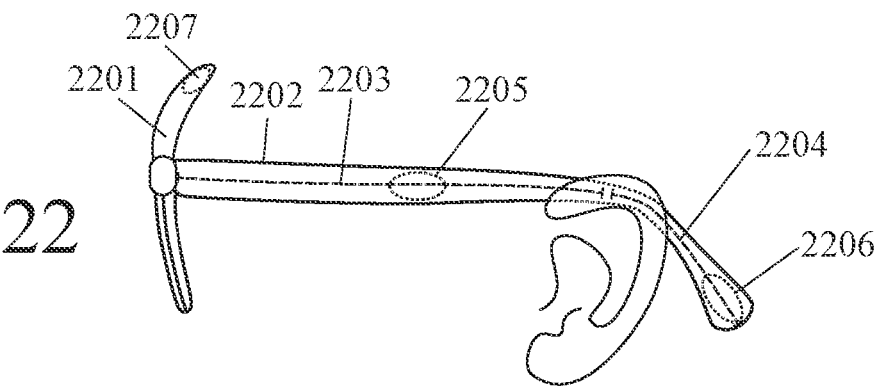
FIGS. 22-24 show three views of eyewear with anterior and posterior electrodes on a temple, arches above front rims, and an electrode on an arch.
Figure 23:
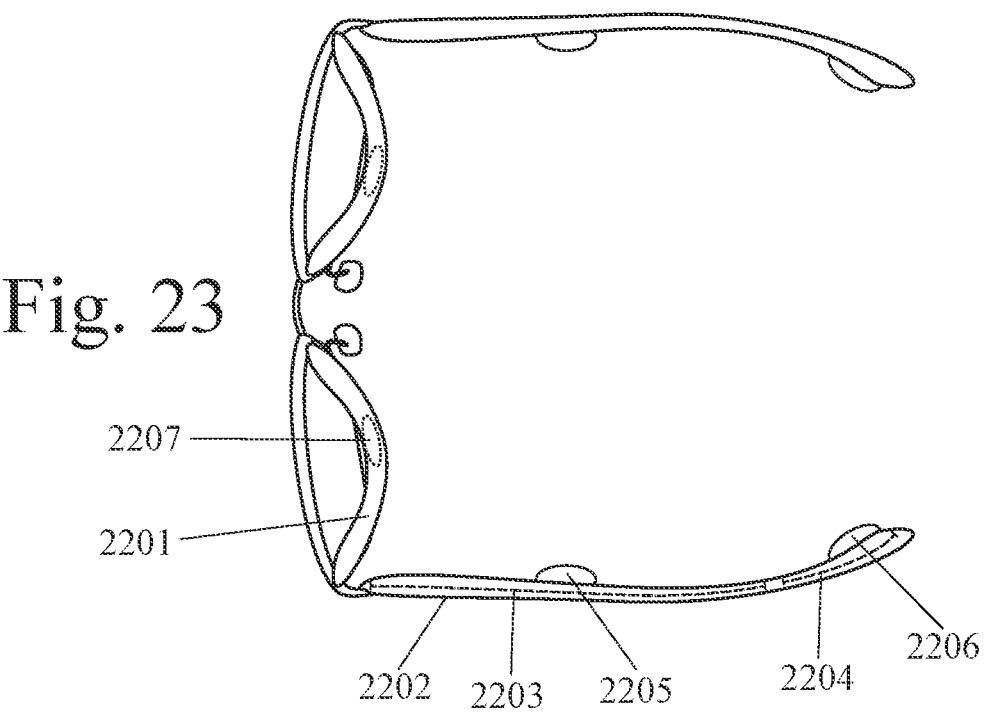
Figure 24:
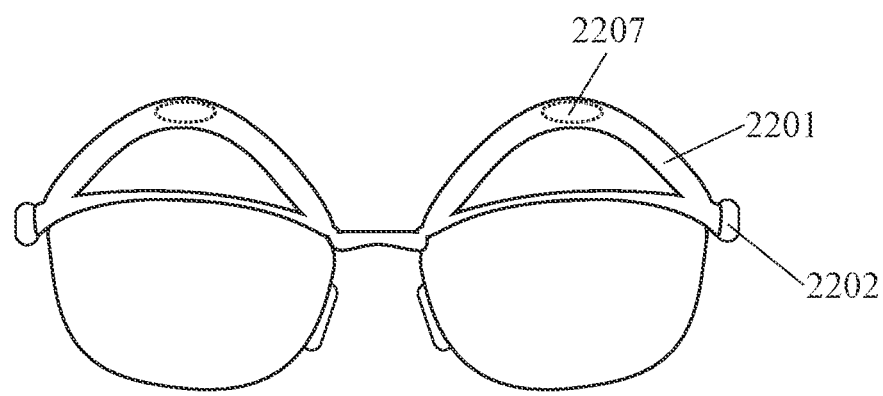

FIGS. 22-24 show three different views of an example of eyewear (e.g. eyeglasses) with electrodes (e.g. EEG sensors) which can collect brain activity data (e.g. electroencephalographic data) which can be used to predict and/or detect health events (e.g. seizure, stroke, or heart attack) or function as a BCI (Brain-to-Computer Interface) for communication. FIG. 22 shows a side view of the left-side temple (e.g. sidepiece) of the eyewear and the front piece of the eyewear, including an arch above a rim. FIG. 23 shows a top-down view of the left-side and right-side temples and the front piece of the eyewear, including arches above the rims. FIG. 24 shows a frontal view of the front piece of the eyewear and the front ends of the temples.

With respect to specific components, the eyewear shown in FIGS. 22-24 comprises: a front piece 2201 including an arch above a rim; a temple (e.g. sidepiece) 2202; a first anterior electrode (e.g. EEG sensor) 2205 on the anterior portion of the temple; a second anterior electrode 2207 on an arch above a front piece rim; and a posterior electrode (e.g. EEG sensor) 2206 on the posterior portion of the temple. FIGS. 22-24 show the temple being conceptually divided into an anterior portion 2203 (which is anterior to where the temple rests on a person's auricle) and a posterior portion 2204 (which is posterior to where the temple rests on the person's auricle). In an example, the side of an anterior electrode which faces toward a person's head can be substantially flat and the side of a posterior electrode which faces toward the person's head can have a plurality of electroconductive protrusions (e.g. protrusions, prongs, teeth, legs, pins, and/or bumps) which contact the surface of the person's head. In these figures, only left-side components are labeled, but right-side components which are symmetric to those on the left side can be assumed. Specification details and variations discussed in the introductory section of this disclosure or in priority-linked disclosures can be applied to this example where relevant.

Figure 25:
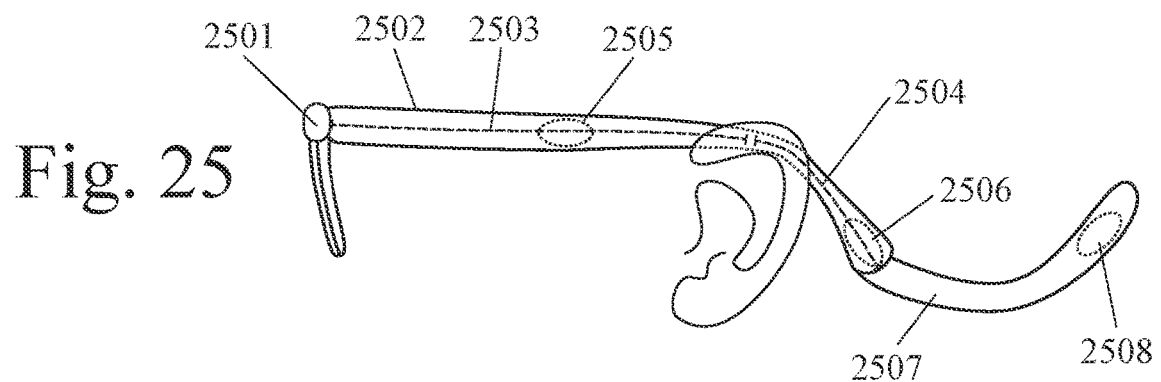
FIGS. 25-27 show three views of eyewear with anterior and posterior electrodes on a temple, a rear band, and an electrode on the rear band.
Figure 26:
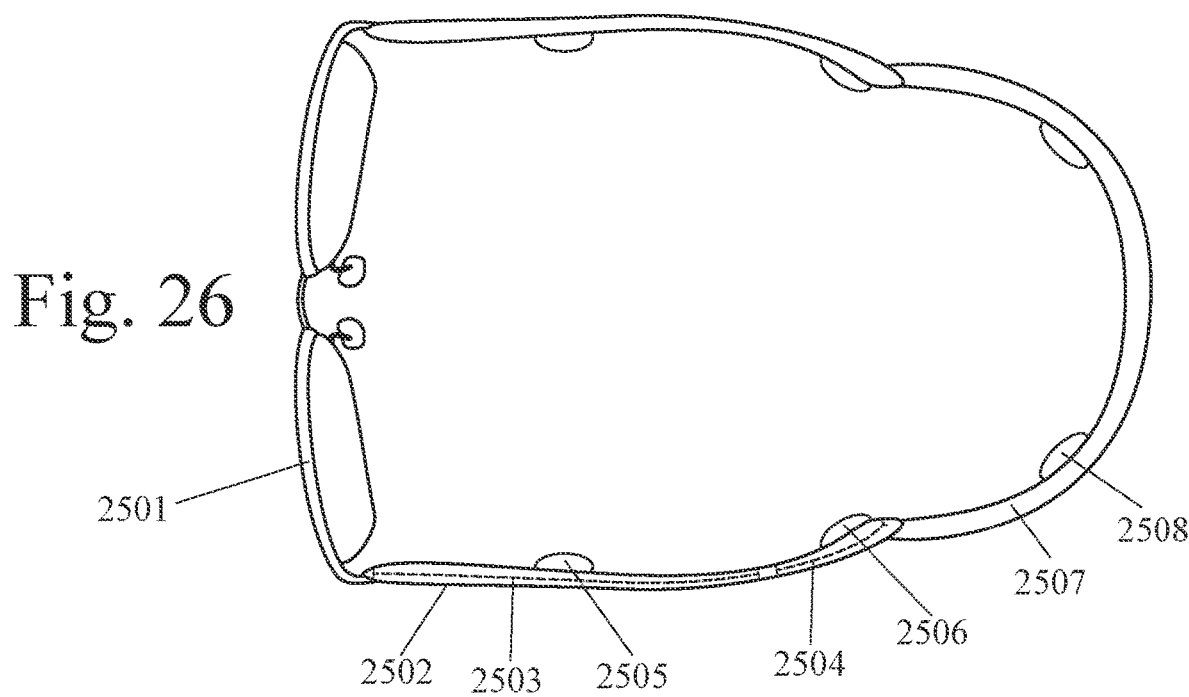
Figure 27:
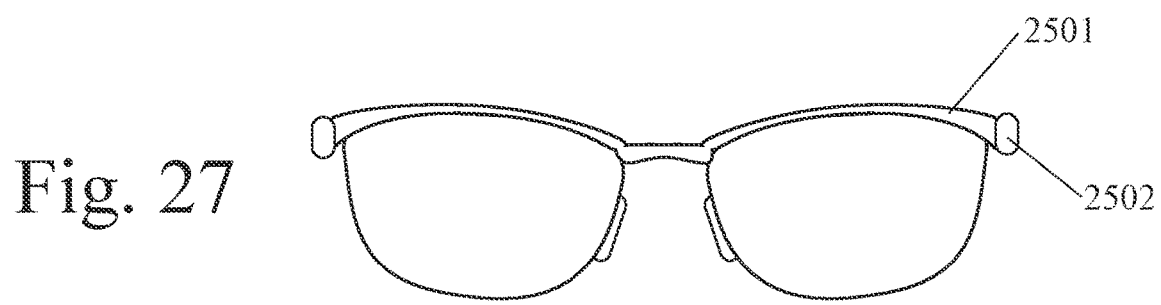

FIGS. 25-27 show three different views of an example of eyewear (e.g. eyeglasses) with electrodes (e.g. EEG sensors) which can collect brain activity data (e.g. electroencephalographic data) which can be used to predict and/or detect health events (e.g. seizure, stroke, or heart attack) or function as a BCI (Brain-to-Computer Interface) for communication. FIG. 25 shows a side view of the left-side temple (e.g. sidepiece) of the eyewear, a rear band (or strap) which curves around the back (e.g. rear one-third) of the person's head from the left-side temple to the right-side temple, and the front piece of the eyewear. FIG. 26 shows a top-down view of the left-side and right-side temples, the rear band (or strap), and the front piece of the eyewear. FIG. 27 shows a frontal view of the front piece of the eyewear and the front ends of the temples.

With respect to specific components, the eyewear shown in FIGS. 25-27 comprises: a front piece 2501; a temple (e.g. sidepiece) 2502; an anterior electrode (e.g. EEG sensor) 2505 on the anterior portion of the temple; a first posterior electrode (e.g. EEG sensor) 2506 on the posterior portion of the temple; a rear band (or strap) 2507 which curves around the back (e.g. rear one-third) of the person's head from the left-side temple to the right-side temple; and at least one second posterior electrode 2508 on the rear band (or strap). FIGS. 25-27 show the temple being conceptually divided into an anterior portion 2503 (which is anterior to where the temple rests on a person's auricle) and a posterior portion 2504 (which is posterior to where the temple rests on the person's auricle). In an example, the side of an anterior electrode which faces toward a person's head can be substantially flat and the side of a posterior electrode which faces toward the person's head can have a plurality of electroconductive protrusions (e.g. protrusions, prongs, teeth, legs, pins, and/or bumps) which contact the surface of the person's head. In these figures, only left-side components are labeled, but right-side components which are symmetric to those on the left side can be assumed. Specification details and variations discussed in the introductory section of this disclosure or in priority-linked disclosures can be applied to this example where relevant.

Figure 28:
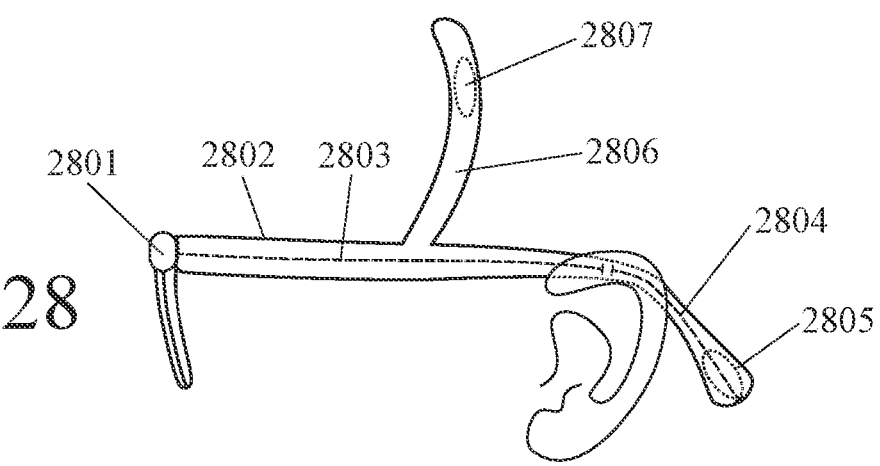
FIGS. 28-30 show three views of eyewear with a posterior electrode on a temple and an anterior electrode on an upper band.
Figure 29:
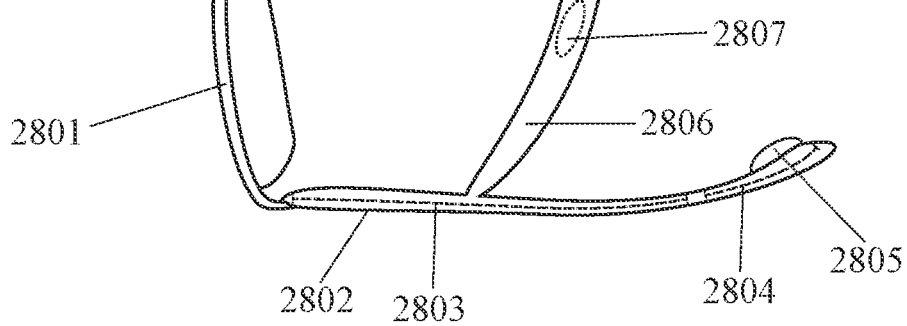
Figure 30:
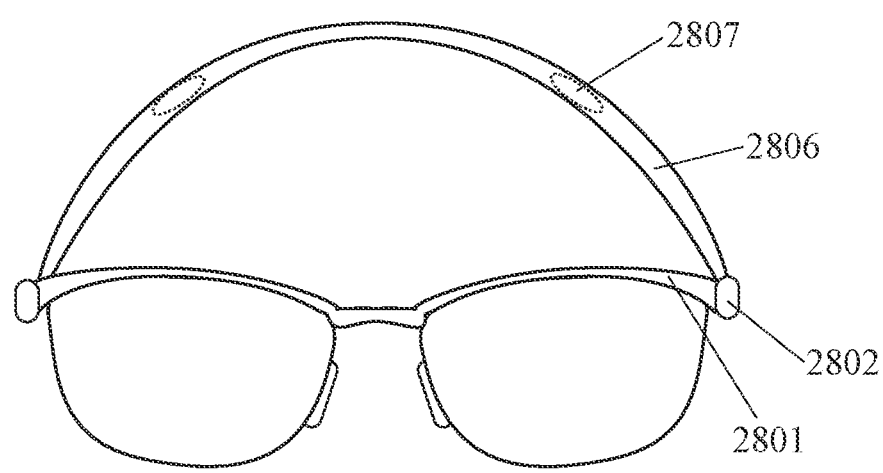

FIGS. 28-30 show three different views of an example of eyewear (e.g. eyeglasses) with electrodes (e.g. EEG sensors) which can collect brain activity data (e.g. electroencephalographic data) which can be used to predict and/or detect health events (e.g. seizure, stroke, or heart attack) or function as a BCI (Brain-to-Computer Interface) for communication. FIG. 28 shows a side view of the left-side temple (e.g. sidepiece) of the eyewear, an upper band (or strap) which loops over the top (e.g. upper one-third) of the person's head from the left-side temple to the right-side temple, and the front piece of the eyewear. FIG. 29 shows a top-down view of the left-side and right-side temples, the upper band (or strap), and the front piece of the eyewear. FIG. 30 shows a frontal view of the front piece of the eyewear, the upper band (or strap), and the front ends of the temples.

With respect to specific components, the eyewear shown in FIGS. 28-30 comprises: a front piece 2801; a temple (e.g. sidepiece) 2802; an anterior electrode (e.g. EEG sensor) 2807 on an upper band (or strap) 2806 which loops over the top (e.g. upper one-third) of the person's head from the left-side temple to the right-side temple; and a posterior electrode (e.g. EEG sensor) 2805 on a posterior portion of the temple. FIGS. 28-30 show the temple being conceptually divided into an anterior portion 2803 (which is anterior to where the temple rests on a person's auricle) and a posterior portion 2804 (which is posterior to where the temple rests on the person's auricle). In an example, the side of an anterior electrode which faces toward a person's head can be substantially flat and the side of a posterior electrode which faces toward the person's head can have a plurality of electroconductive protrusions (e.g. protrusions, prongs, teeth, legs, pins, and/or bumps) which contact the surface of the person's head. In these figures, only left-side components are labeled, but right-side components which are symmetric to those on the left side can be assumed. Specification details and variations discussed in the introductory section of this disclosure or in priority-linked disclosures can be applied to this example where relevant.

Figure 31:
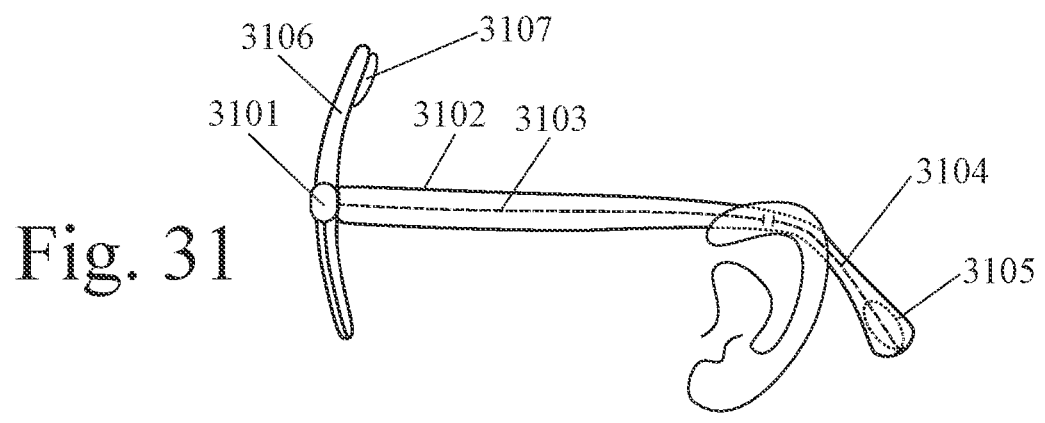
FIGS. 31-33 show three views of eyewear with an electrode on a temple and an electrode on a brow bar.
Figure 32:
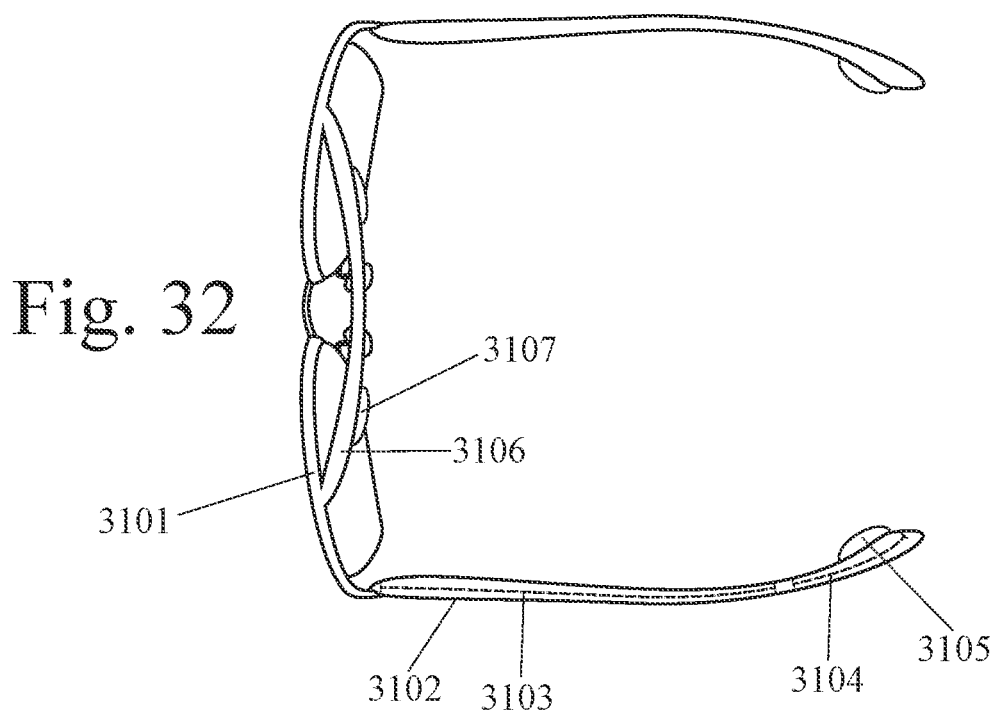
Figure 33:
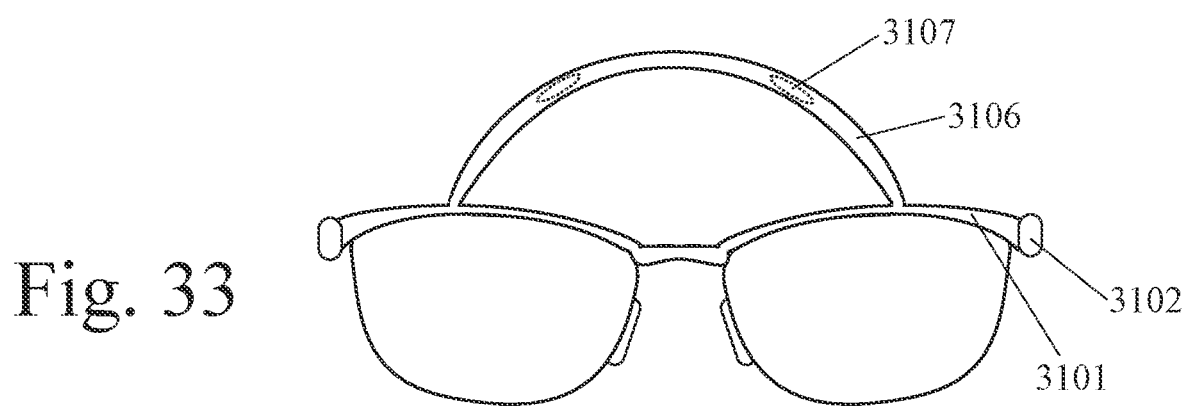

FIGS. 31-33 show three different views of an example of eyewear (e.g. eyeglasses) with electrodes (e.g. EEG sensors) which can collect brain activity data (e.g. electroencephalographic data) which can be used to predict and/or detect health events (e.g. seizure, stroke, or heart attack) or function as a BCI (Brain-to-Computer Interface) for communication. FIG. 31 shows a side view of the left-side temple (e.g. sidepiece) of the eyewear and the front piece of the eyewear, including a brow bar between the rims of the front piece. FIG. 32 shows a top-down view of the left-side and right-side temples and the front piece of the eyewear, including the brow bar. FIG. 33 shows a frontal view of the front piece of the eyewear and the front ends of the temples.

With respect to specific components, the eyewear shown in FIGS. 31-33 comprises: a front piece 3101 including a brow bar 3106 between the rims of the front piece; a temple (e.g. sidepiece) 3102; at least one anterior electrode (e.g. EEG sensor) 3107 on the brow bar; and a posterior electrode (e.g. EEG sensor) 3105 on a posterior portion of the temple. FIGS. 31-33 show the temple being conceptually divided into an anterior portion 3103 (which is anterior to where the temple rests on a person's auricle) and a posterior portion 3104 (which is posterior to where the temple rests on the person's auricle). In an example, the side of an anterior electrode which faces toward a person's head can be substantially flat and the side of a posterior electrode which faces toward the person's head can have a plurality of electroconductive protrusions (e.g. protrusions, prongs, teeth, legs, pins, and/or bumps) which contact the surface of the person's head. In these figures, only left-side components are labeled, but right-side components which are symmetric to those on the left side can be assumed. Specification details and variations discussed in the introductory section of this disclosure or in priority-linked disclosures can be applied to this example where relevant.

Figure 34:
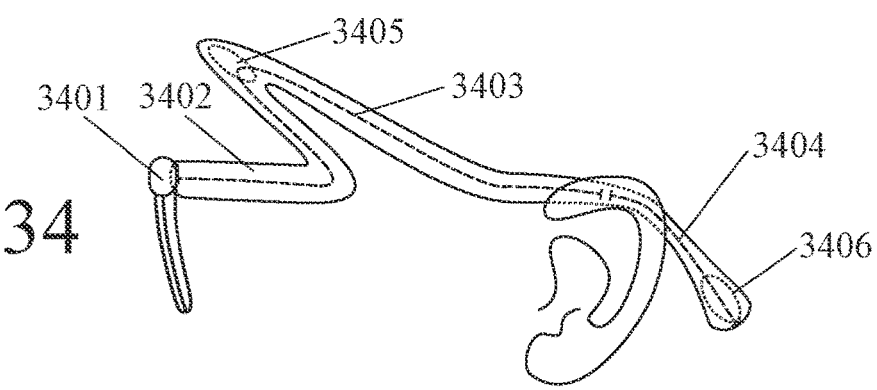
FIGS. 34-36 show three views of eyewear with a temple with a forward and inward wave, an anterior electrode on the wave, and a posterior electrode.
Figure 35:
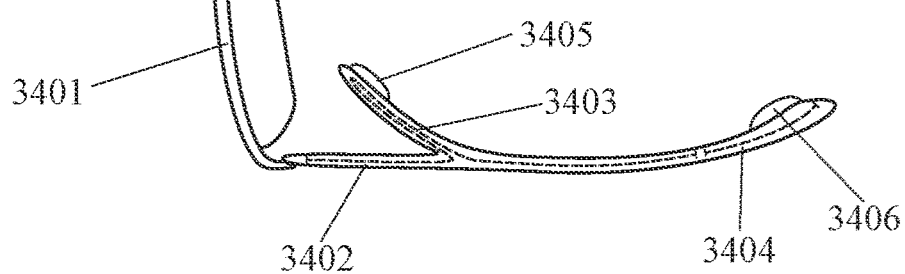
Figure 36:
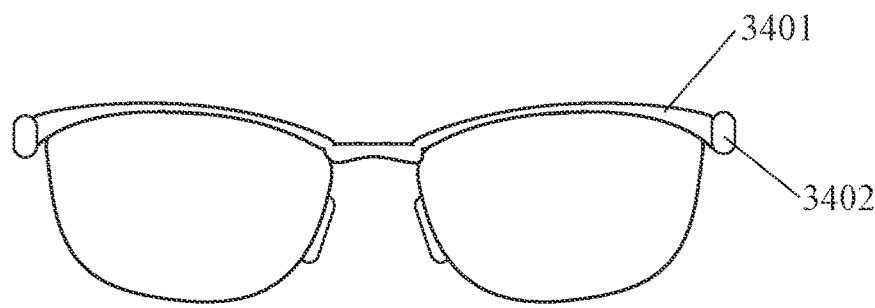

FIGS. 34-36 show three different views of an example of eyewear (e.g. eyeglasses) with electrodes (e.g. EEG sensors) which can collect brain activity data (e.g. electroencephalographic data) which can be used to predict and/or detect health events (e.g. seizure, stroke, or heart attack) or function as a BCI (Brain-to-Computer Interface) for communication. FIG. 34 shows a side view of the left-side temple (e.g. sidepiece) of the eyewear and the front piece of the eyewear. FIG. 35 shows a top-down view of the left-side and right-side temples and the front piece of the eyewear. FIG. 36 shows a frontal view of the front piece of the eyewear and the front ends of the temples.

With respect to specific components, the eyewear shown in FIGS. 34-36 comprises: a front piece 3401; a temple (e.g. sidepiece) 3402 with a forward and inward curving wave (e.g. wave, loop, or arm) on the anterior portion of the temple; an anterior electrode (e.g. EEG sensor) 3405 on the wave; and a posterior electrode (e.g. EEG sensor) 3406 on a posterior portion of the temple. FIGS. 34-36 show the temple being conceptually divided into an anterior portion 3403 (which is anterior to where the temple rests on a person's auricle) and a posterior portion 3404 (which is posterior to where the temple rests on the person's auricle).

In an example, the side of an anterior electrode which faces toward a person's head can be substantially flat and the side of a posterior electrode which faces toward the person's head can have a plurality of electroconductive protrusions (e.g. protrusions, prongs, teeth, legs, pins, and/or bumps) which contact the surface of the person's head. In these figures, only left-side components are labeled, but right-side components which are symmetric to those on the left side can be assumed. Specification details and variations discussed in the introductory section of this disclosure or in priority-linked disclosures can be applied to this example where relevant.

Figure 37:
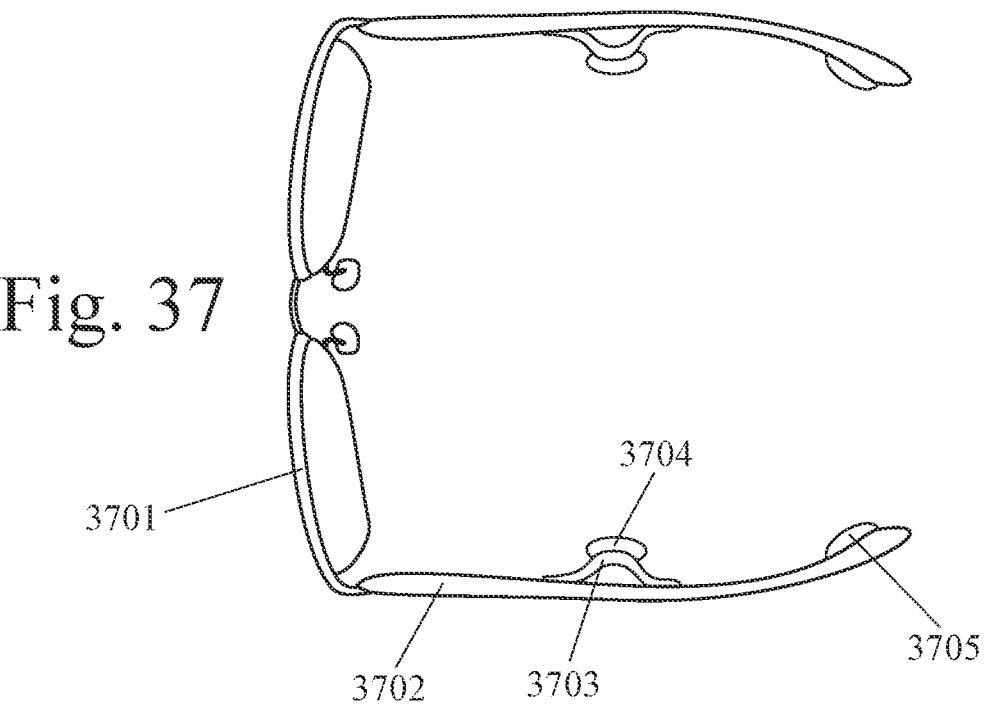
FIG. 37 shows a top-down view of eyewear with a concave spring between an electrode and a temple.

FIG. 37 shows a top-down view of eyewear (e.g. eyeglasses) which illustrates details for one way that electrodes (e.g. EEG sensors) on eyewear can be configured and/or held onto a person's head. These details can be applied to any of the eyewear designs which are shown in FIGS. 1-36. FIG. 37 shows a flexible protrusion between an electrode (e.g. EEG sensor) and an eyewear temple (e.g. sidepiece). This protrusion pushes an electrode out from the temple and holds the electrode against a person's head. In this example, the protrusion is a concave spring (or tensile strip), wherein the concavity faces toward the temple. In this example, the anterior and posterior ends of the protrusion (e.g. spring) are attached to the temple, but the middle of the protrusion is not attached to the temple. In this example, the protrusion has a wave and/or partial-sinusoidal shape. In another example, the protrusion can have a semi-circular or arch shape.

In an example, the extent to which a protrusion (e.g. spring) extends out from a temple and/or the pressure with which the protrusion (e.g. spring) holds the electrode against a person's head can be adjusted. In an example, the extension and/or pressure of the protrusion can be increased by moving the anterior and posterior ends of the protrusion closer together. When the ends of the protrusion are moved closer together, this causes the middle of the protrusion to bulge out farther toward the person's head. In an example, the extension and/or pressure of the protrusion can be decreased by moving the anterior and posterior ends of the protrusion farther apart. In an example, the anterior and posterior ends of the protrusion can be moved by moving (e.g. sliding) a knob, button, pin, or clip. In an example, a knob, button, pin, or clip can slide along a track (or channel) on the temple.

With respect to specific components, FIG. 37 shows eyewear (e.g. eyeglasses) with electrodes comprising: a front piece 3701; a temple 3702; an anterior electrode (e.g. EEG sensor) 3704; a flexible protrusion 3703 between the temple and the anterior electrode, wherein the protrusion is a concave spring (or tensile strip) whose anterior and posterior ends are attached to the temple but whose middle is not attached to the temple; and a posterior electrode 3705.

In an example, the side of an anterior electrode which faces toward a person's head can be substantially flat and the side of a posterior electrode which faces toward the person's head can have a plurality of electroconductive protrusions (e.g. protrusions, prongs, teeth, legs, pins, and/or bumps) which contact the surface of the person's head. In these figures, only left-side components are labeled, but right-side components which are symmetric to those on the left side can be assumed. Specification details and variations discussed in the introductory section of this disclosure or in priority-linked disclosures can be applied to this example where relevant.

Figure 38:
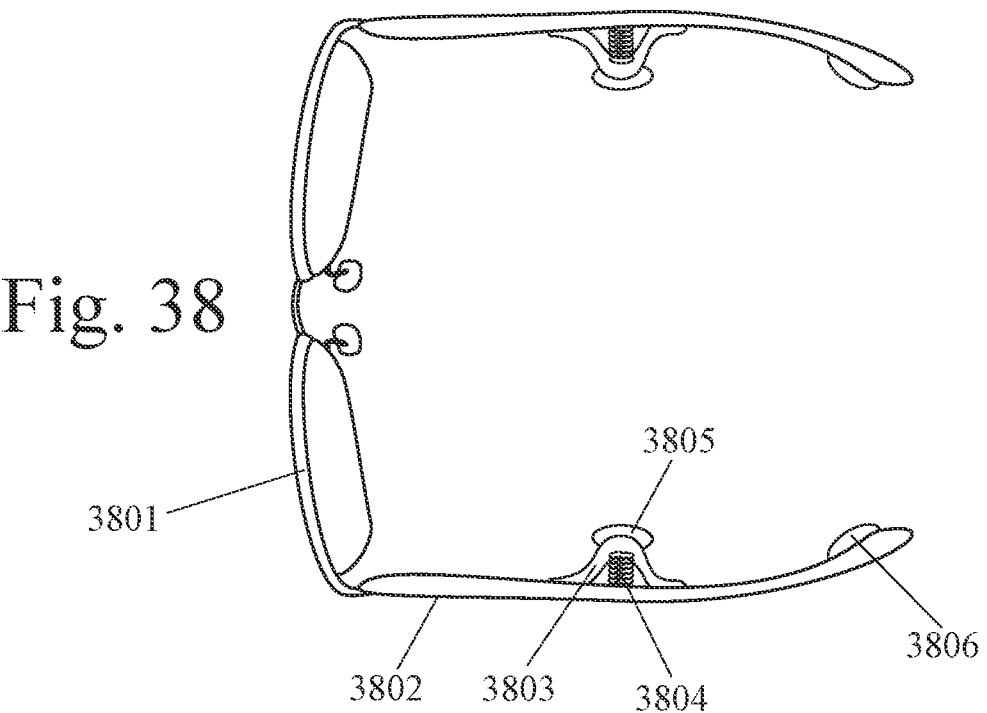
FIG. 38 shows a top-down view of eyewear with concave and helical springs between an electrode and a temple.

FIG. 38 shows a top-down view of eyewear (e.g. eyeglasses) which illustrates details for one way that electrodes (e.g. EEG sensors) on eyewear can be configured and/or held onto a person's head. These details can be applied to any of the eyewear designs which are shown in FIGS. 1-36. FIG. 38 shows a flexible protrusion between an electrode (e.g. EEG sensor) and an eyewear temple (e.g. sidepiece). This protrusion pushes an electrode out from the temple and holds the electrode against a person's head. In this example, the protrusion is a concave spring (or tensile strip) wherein the concavity faces toward the temple. In this example, the anterior and posterior ends of the protrusion (e.g. spring) are attached to the temple and there is also a helical spring between the protrusion and the temple. In this example, the protrusion has a wave and/or partial-sinusoidal shape. In another example, the protrusion can have a semi-circular or arch shape.

In an example, the extent to which a protrusion (e.g. spring) extends out from a temple and/or the pressure with which the protrusion (e.g. spring) holds the electrode against a person's head can be adjusted. In an example, the extension and/or pressure of the protrusion can be increased by moving the anterior and posterior ends of the protrusion closer together. When the ends of the protrusion are moved closer together, this causes the middle of the protrusion to bulge out farther toward the person's head. In an example, the extension and/or pressure of the protrusion can be decreased by moving the anterior and posterior ends of the protrusion farther apart. In an example, the anterior and posterior ends of the protrusion can be moved by moving (e.g. sliding) a knob, button, pin, or clip. In an example, a knob, button, pin, or clip can slide along a track (or channel) on the temple.

With respect to specific components, FIG. 38 shows eyewear (e.g. eyeglasses) with electrodes comprising: a front piece 3801; a temple 3802; an anterior electrode (e.g. EEG sensor) 3805; a flexible protrusion 3803 between the temple and the anterior electrode, wherein the protrusion is a concave spring (or tensile strip) whose anterior and posterior ends are attached to the temple; a helical spring 3804 between the flexible protrusion and the temple; and a posterior electrode 3806.

In an example, the side of an anterior electrode which faces toward a person's head can be substantially flat and the side of a posterior electrode which faces toward the person's head can have a plurality of electroconductive protrusions (e.g. protrusions, prongs, teeth, legs, pins, and/or bumps) which contact the surface of the person's head. In these figures, only left-side components are labeled, but right-side components which are symmetric to those on the left side can be assumed. Specification details and variations discussed in the introductory section of this disclosure or in priority-linked disclosures can be applied to this example where relevant.

Figure 39:
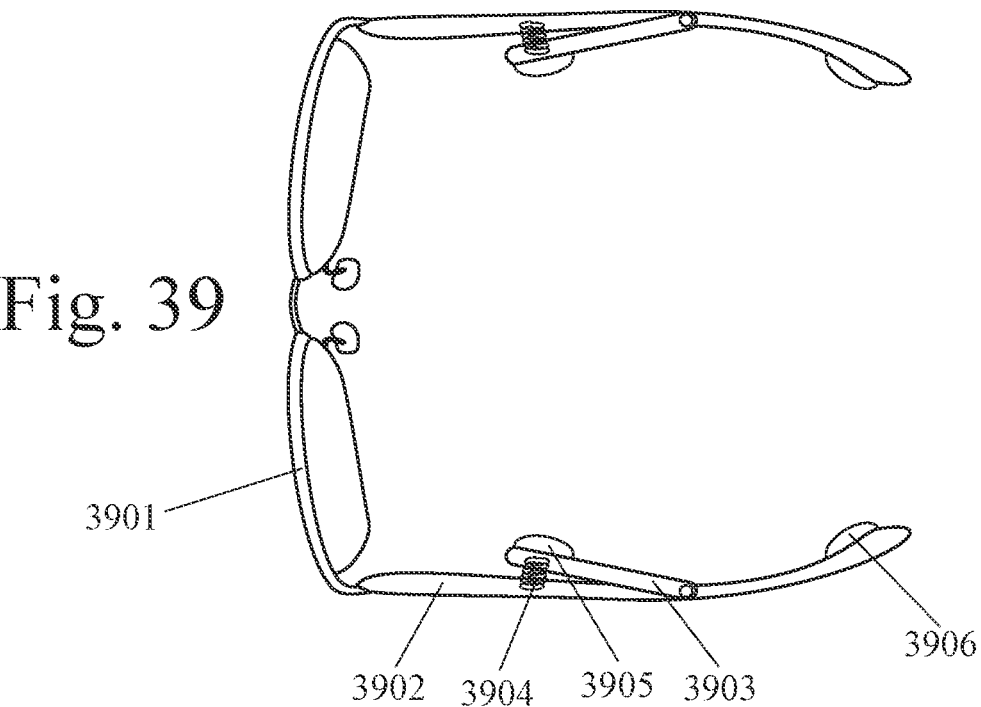
FIG. 39 shows a top-down view of eyewear with a pivoting arm and a spring between an electrode and a temple.

FIG. 39 shows a top-down view of eyewear (e.g. eyeglasses) which illustrates details for one way that electrodes (e.g. EEG sensors) on eyewear can be configured and/or held onto a person's head. These details can be applied to any of the eyewear designs which are shown in FIGS. 1-36. FIG. 39 shows a flexible protrusion between an electrode (e.g. EEG sensor) and an eyewear temple (e.g. sidepiece). This protrusion pushes an electrode out from the temple and holds the electrode against a person's head. In this example, the protrusion is a pivoting arm, wherein one end of the arm is attached via a movable joint to the temple. In this example, there is also a helical spring between the arm and the temple.

With respect to specific components, FIG. 39 shows eyewear (e.g. eyeglasses) with electrodes comprising: a front piece 3901; a temple 3902; an anterior electrode (e.g. EEG sensor) 3905; a pivoting arm 3903 between the anterior electrode and the temple; a helical spring 3904 between the pivoting arm and the temple; and a posterior electrode 3906.

In an example, the side of an anterior electrode which faces toward a person's head can be substantially flat and the side of a posterior electrode which faces toward the person's head can have a plurality of electroconductive protrusions (e.g. protrusions, prongs, teeth, legs, pins, and/or bumps) which contact the surface of the person's head. In these figures, only left-side components are labeled, but right-side components which are symmetric to those on the left side can be assumed. Specification details and variations discussed in the introductory section of this disclosure or in priority-linked disclosures can be applied to this example where relevant.

Figure 40:
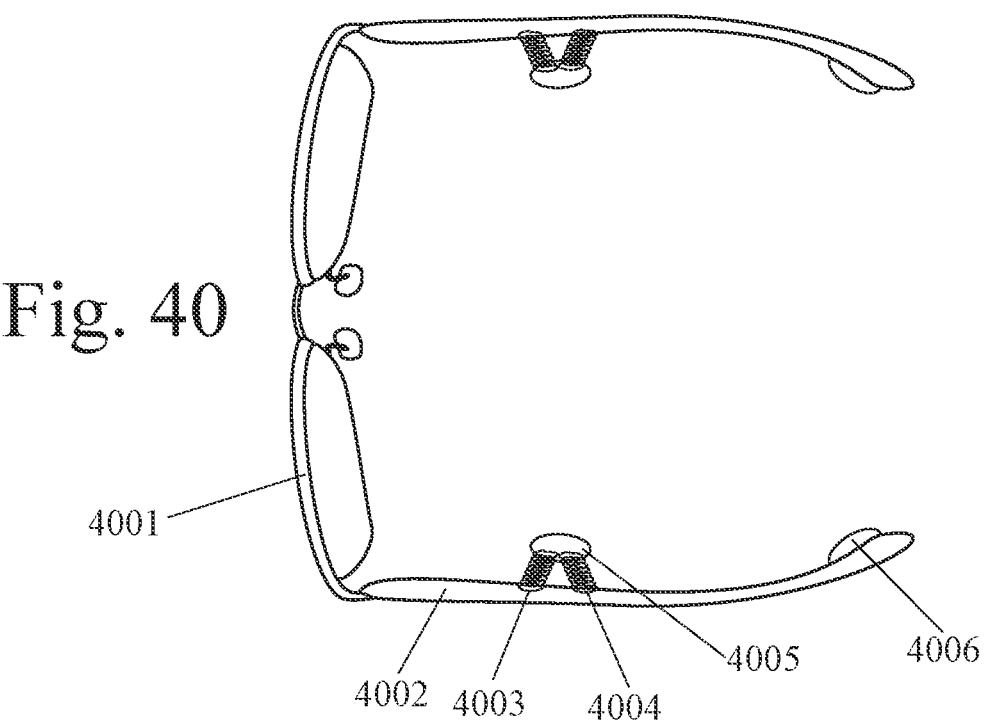
FIG. 40 shows a top-down view of eyewear with two springs between an electrode and a temple.

FIG. 40 shows a top-down view of eyewear (e.g. eyeglasses) which illustrates details for one way that electrodes (e.g. EEG sensors) on eyewear can be configured and/or held onto a person's head. These details can be applied to any of the eyewear designs which are shown in FIGS. 1-36. FIG. 40 shows two helical springs between an electrode (e.g. EEG sensor) and an eyewear temple (e.g. sidepiece). The two springs push an electrode out from the temple and hold the electrode against a person's head. These two springs together hold the electrode in a more-stable manner and a more-consistent position than just one spring. In this example, there is an anterior spring and a posterior spring.

With respect to specific components, FIG. 40 shows eyewear (e.g. eyeglasses) with electrodes comprising: a front piece 4001; a temple 4002; an anterior electrode (e.g. EEG sensor) 4005; an anterior spring 4003 and a posterior spring 4004 between the anterior electrode and the temple; and a posterior electrode 4006.

In an example, the side of an anterior electrode which faces toward a person's head can be substantially flat and the side of a posterior electrode which faces toward the person's head can have a plurality of electroconductive protrusions (e.g. protrusions, prongs, teeth, legs, pins, and/or bumps) which contact the surface of the person's head. In these figures, only left-side components are labeled, but right-side components which are symmetric to those on the left side can be assumed. Specification details and variations discussed in the introductory section of this disclosure or in priority-linked disclosures can be applied to this example where relevant.

Figure 41:
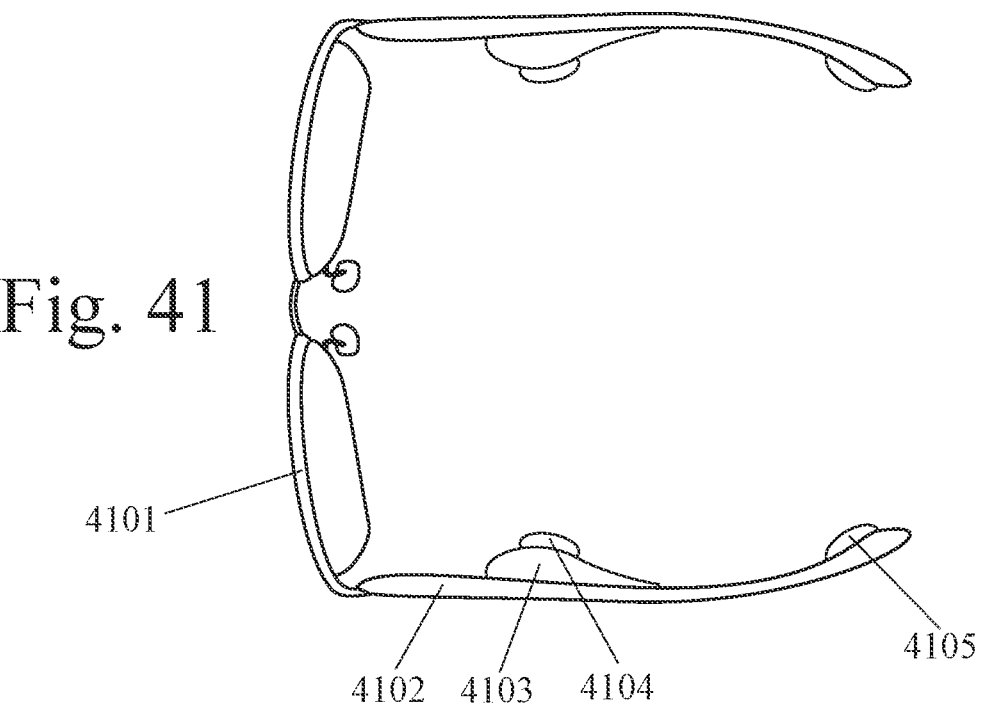
FIG. 41 shows a top-down view of eyewear with a piece of foam or gel between an electrode and a temple.

FIG. 41 shows a top-down view of eyewear (e.g. eyeglasses) which illustrates details for one way that electrodes (e.g. EEG sensors) on eyewear can be configured and/or held onto a person's head. These details can be applied to any of the eyewear designs which are shown in FIGS. 1-36. FIG. 41 shows a flexible protrusion between an electrode (e.g. EEG sensor) and an eyewear temple (e.g. sidepiece). This protrusion pushes an electrode out from the temple and holds the electrode against a person's head. In this example, the protrusion is a piece of compressible foam or gel.

With respect to specific components, FIG. 41 shows eyewear (e.g. eyeglasses) with electrodes comprising: a front piece 4101; a temple 4102; an anterior electrode (e.g. EEG sensor) 4104; a piece of compressible foam or gel 4103 between the anterior electrode and the temple; and a posterior electrode 4105.

In an example, the side of an anterior electrode which faces toward a person's head can be substantially flat and the side of a posterior electrode which faces toward the person's head can have a plurality of electroconductive protrusions (e.g. protrusions, prongs, teeth, legs, pins, and/or bumps) which contact the surface of the person's head. In these figures, only left-side components are labeled, but right-side components which are symmetric to those on the left side can be assumed. Specification details and variations discussed in the introductory section of this disclosure or in priority-linked disclosures can be applied to this example where relevant.

Figure 42:
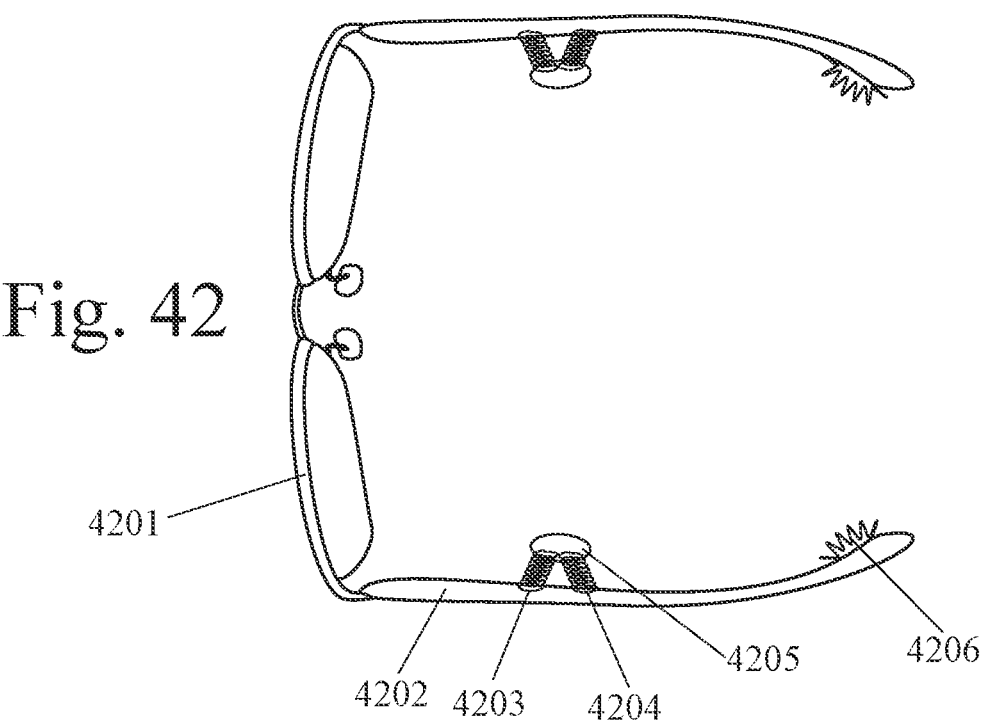
FIG. 42 shows a top-down view of eyewear with an anterior electrode with a flat surface and a posterior electrode with protrusions.

FIG. 42 shows a top-down view of eyewear (e.g. eyeglasses) which illustrates details for one way that electrodes (e.g. EEG sensors) on eyewear can be configured and/or held onto a person's head. These details can be applied to any of the eyewear designs which are shown in FIGS. 1-36. FIG. 42 shows two helical springs between an electrode (e.g. EEG sensor) and an eyewear temple (e.g. sidepiece). The two springs push an electrode out from the temple and hold the electrode against a person's head. These two springs together hold the electrode in a more-stable manner and a more-consistent position than just one spring. In this example, there is an anterior spring and a posterior spring. FIG. 42 also shows an example wherein the surface of a posterior electrode which faces toward the person's head has a plurality of electroconductive protrusions.

With respect to specific components, FIG. 42 shows eyewear (e.g. eyeglasses) with electrodes comprising: a front piece 4201; a temple 4202; an anterior electrode (e.g. EEG sensor) 4205; an anterior spring 4203 and a posterior spring 4204 between the anterior electrode and the temple; and a posterior electrode 4206 with a plurality of electroconductive protrusions.

In this example, the side of an anterior electrode which faces toward a person's head is substantially flat and the side of the posterior electrode which faces toward the person's head has a plurality of electroconductive protrusions (e.g. protrusions, prongs, teeth, legs, pins, and/or bumps) which contact the surface of the person's head. In these figures, only left-side components are labeled, but right-side components which are symmetric to those on the left side can be assumed. Specification details and variations discussed in the introductory section of this disclosure or in priority-linked disclosures can be applied to this example where relevant.

Figure 43:
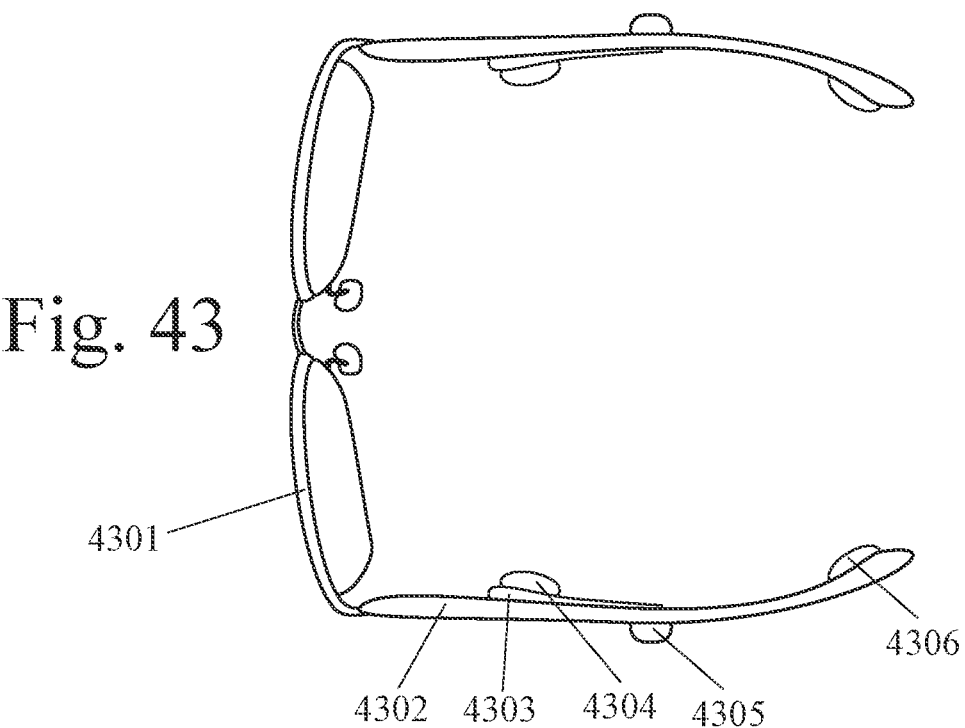
FIGS. 43-44 show sequential top-down views of eyewear with an expandable chamber between an electrode and a temple.
Figure 44:
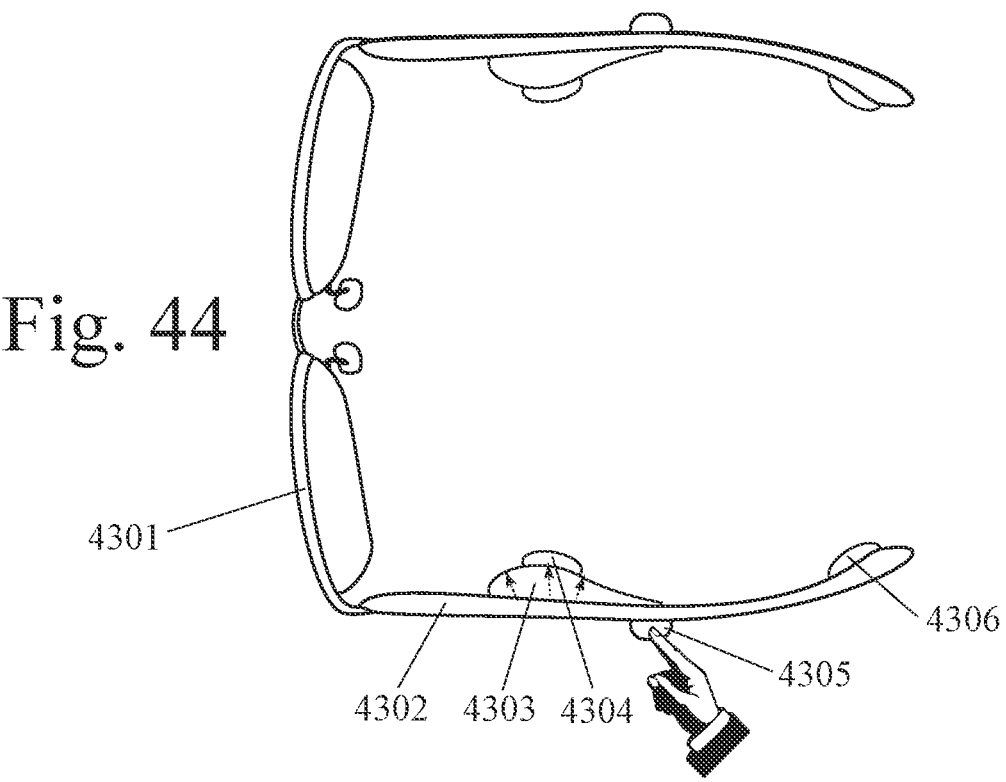

FIGS. 43-44 show two top-down views, at two different times, of eyewear (e.g. eyeglasses) which illustrates details for one way that electrodes (e.g. EEG sensors) on eyewear can be configured and/or held onto a person's head. These details can be applied to any of the eyewear designs which are shown in FIGS. 1-36. FIG. 43 shows an expandable (e.g. inflatable, pneumatic, and/or hydraulic) chamber between an electrode (e.g. EEG sensor) and an eyewear temple (e.g.

sidepiece). This expandable chamber protrusion pushes an electrode out from the temple and holds the electrode against a person's head. In this example, the expandable chamber is an inflatable chamber. FIG. 43 shows this chamber at a first time before it is inflated. FIG. 44 shows this chamber at a second time after it has been inflated.

With respect to specific components, FIG. 43 shows eyewear (e.g. eyeglasses) with electrodes comprising: a front piece 4301; a temple 4302; an anterior electrode (e.g. EEG sensor) 4304; an expandable (e.g. inflatable, pneumatic, and/or hydraulic) chamber 4303 between the anterior electrode and the temple; a pump 4305 which expands the chamber; and a posterior electrode 4306. In this example, the pump is manually pressed to force air into the expandable chamber. In another example, the pump can be automated. In another example, fluid instead of air can be forced into the chamber in order to expand it.

In an example, the side of an anterior electrode which faces toward a person's head can be substantially flat and the side of a posterior electrode which faces toward the person's head can have a plurality of electroconductive protrusions (e.g. protrusions, prongs, teeth, legs, pins, and/or bumps) which contact the surface of the person's head. In these figures, only left-side components are labeled, but right-side components which are symmetric to those on the left side can be assumed. Specification details and variations discussed in the introductory section of this disclosure or in priority-linked disclosures can be applied to this example where relevant.

I claim:

1. Eyewear with electrodes comprising:
an eyewear front piece;
two eyewear temples, wherein each eyewear temple is divided into an anterior portion which is anterior to where the eyewear temple is configured to rest on a person's auricle and a posterior portion which is posterior to where each eyewear temple is configured to rest on the person's auricle, and wherein the anterior portion further comprises a wave and/or loop which spans upward, forward, and inward to a location over the person's forehead and then spans downward, backward, and outward;
at least one anterior electrode on the wave and/or loop of each eyewear temple;
at least one posterior electrode on the posterior portion of each eyewear temple; and wherein the at least one anterior electrode and at least one posterior electrode are configured to detect electroencephalograph signals.

* * * * *